(12) United States Patent
Letellier et al.

(10) Patent No.: US 11,834,717 B2
(45) Date of Patent: Dec. 5, 2023

(54) BIOMARKERS FOR CANCER DIAGNOSIS, PREDICTION OR STAGING

(71) Applicant: Universite du Luxembourg, Esch-sur-Alzette (LU)

(72) Inventors: Elisabeth Letellier, Luxembourg (LU); Martine Schmitz, Luxembourg (LU); Aurelien Ginolhac, Esch-sur-Alzette (LU); Serge Haan, Mondercange (LU)

(73) Assignee: Universite du Luxembourg, Esch-sur-Alzette (LU)

( * ) Notice: Subject to any disclaimer, the term of this patent is extended or adjusted under 35 U.S.C. 154(b) by 39 days.

(21) Appl. No.: 16/638,482

(22) PCT Filed: Aug. 10, 2018

(86) PCT No.: PCT/EP2018/071734
§ 371 (c)(1),
(2) Date: Feb. 12, 2020

(87) PCT Pub. No.: WO2019/034549
PCT Pub. Date: Feb. 21, 2019

(65) Prior Publication Data
US 2020/0362417 A1 Nov. 19, 2020

(30) Foreign Application Priority Data

Aug. 14, 2017 (EP) .................................... 17186112
Aug. 14, 2017 (LU) .................................. LU100371

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01)

(58) Field of Classification Search
CPC .................................................. C12Q 1/6886
See application file for complete search history.

(56) References Cited

U.S. PATENT DOCUMENTS

2010/0284915 A1* 11/2010 Dai ...................... C12Q 1/6886
424/9.1
2016/0208333 A1* 7/2016 Schell .................. C12Q 1/6886

FOREIGN PATENT DOCUMENTS

| EP | 3009842 A2 | 4/2016 |
| WO | 2012149609 A1 | 11/2012 |
| WO | 2015017537 A2 | 2/2015 |

OTHER PUBLICATIONS

Palmer et al. BMC Genomics. 2006. 7:115. (Year: 2006).*
Saito-Hisaminato et al. DNA Research. 2002. 9:35-45. (Year: 2002).*
Whitehead et al. Genome Biology. 2005. 6:R13. (Year: 2005).*
Chan. G & P Magazine. 2006. 6(3):20-26. (Year: 2006).*
Chen et al. Molecular & Cellular Proteomics. 2002. 1:304-313. (Year: 2002).*
Greenbaum et al. Genome Biology. 2003. 4:117. (Year: 2003).*
Kendrick. "A gene's mRNA level does not usually predict its protein level". Kendrick Labs, Inc. Sep. 25, 2014. (Year: 2014).*
Maier et al. FEBS Letters. 2009. 583:3966-3973. (Year: 2009).*
Pascal et al. BMC Genomics. 2008. 9:246. (Year: 2008).*
Canani et al. Nat Rev Gastroenterol Hepatol. 2015. 12(5): 293-302. (Year: 2015).*
Garcia. "Myosin VB in intestinal pathogenesis". Jun. 2017. Doctoral Thesis. Vall d'Hebron Research Institute. (Year: 2017).*
Kravtsov et al. Am J Physiol Gastrointest Liver Physiol. 2014. 307: G992-G1001. (Year: 2014).*
Szperl et al. Pediatr Gastroenterol Nutr. 2011. 52(3): 307-313. (Year: 2011).*
Ouderkirk et al. Cytoskeleton. 2014. 71:447-463. (Year: 2014).*
Letellier et al., "Loss of myosin Vb in colorectal cancer is a strong prognostic factor for disease recurrence", British Journal of Cancer, Oct. 12, 2017, 117:11, 1689-1701.
International Search Report and Written Opinion for Application No. PCT/EP2018/071734, dated Nov. 26, 2018, 13 pages.
Roland, et al., "Rab GTPase-Myo5B complexes control membrane recycling and epithelial polarization", PNAS, Feb. 15, 2011, vol. 108, No. 7, pp. 2789-2794, www.pnas.org/cgi/doi/10.1073/pnas.1010754108, XP55520288A.
European Patent Office Communication pursuant to Article 94(3) EPC for App. No. EP18759052.6, dated Mar. 26, 2021, 12 pages.
Gopal Krishnan Priya D. et al: "Rab GTPases: Emerging Oncogenes and Tumor Suppressive Regulators for the Editing of Survival Pathways in Cancer", Cancers, vol. 12, No. 2, Jan. 21, 2020 (Jan. 21, 2020), p. 259, XP055787732, DOI: 10.3390/cancers12020259 Retrieved from the Internet: URL:https://www.ncbi.nlm.nih.gov/pmc/articles/PMC7072214/pdf/ cancers-12-00259.pdf.

* cited by examiner

*Primary Examiner* — Joseph G. Dauner
(74) *Attorney, Agent, or Firm* — Riverside Law LLP

(57) ABSTRACT

The present invention relates to a method for predicting clinical outcome for a subject diagnosed with colorectal cancer, skin cancer, head and neck cancer or lung cancer. It also relates to a method for predicting whether a subject has a predisposition to develop such cancers as well as to a method for aiding the staging of such cancers in a subject. The methods of the present invention apply to the biomarkers MYO5B and/or RAB8A and optionally in addition to RAB9A, RAB10, RAB11A, RAB25, CDC42, RAC and/or RhoA.

11 Claims, 22 Drawing Sheets
Specification includes a Sequence Listing.

B

B

BIOMARKERS FOR CANCER DIAGNOSIS, PREDICTION OR STAGING

This application contains a Sequence Listing in computer readable form, which is incorporated herein by reference.

TECHNICAL FIELD OF THE INVENTION

The present invention relates to a method for predicting clinical outcome for a subject diagnosed with colorectal cancer, skin cancer, head and neck cancer or lung cancer. It also relates to a method for predicting whether a subject has a predisposition to develop such cancers as well as to a method for aiding the staging of such cancers in a subject. The methods of the present invention apply to the biomarkers MYO5B and/or RAB8A and optionally in addition to RAB9A, RAB10, RAB11A. RAB25, CDC42, RAC and/or RhoA.

BACKGROUND ART

Cancer is a group of diseases involving abnormal cell growth with the potential to invade or spread to other parts of the body. Over 100 types of cancers affect humans. In 2015 about 90.5 million people had cancer. The risk of cancer increases significantly with age and many cancers occur more commonly in developed countries.

Colorectal cancer (CRC) is one of the most frequent and deadly cancers in the western world with more than 1.2 million yearly diagnoses and approximately 600,000 deaths each year (Torre et al, 2015). Patient survival is largely dependent on early diagnosis and intervention. Accordingly, there is an urgent need for novel diagnostic parameters as well as molecular determinants of clinical outcome, which would allow for the targeted treatment of patients at risk of relapse. Especially in stage II patients, the identification of biomarkers predicting the recurrence of the disease is an unmet clinical need.

Skin cancer is the most common form of cancer, globally accounting for at least 40% of cases. The most common type is nonmelanoma skin cancer, which occurs in at least 2-3 million people per year. Of nonmelanoma skin cancers, about 80% are basal-cell cancers and 20% squamous-cell skin cancers. Basal-cell and squamous-cell skin cancers rarely result in death. In the United States they were the cause of less than 0.1% of all cancer deaths. Globally in 2012 melanoma occurred in 232,000 people, and resulted in 55,000 deaths. Australia and New Zealand have the highest rates of melanoma in the world. The three main types of skin cancer have become more common in the last 20 to 40 years, especially in those areas which are mostly Caucasian.

Head and neck cancer is a group of cancers that starts within the mouth, nose, throat, larynx, sinuses, or salivary glands. Symptoms may include a lump or sore that does not heal, a sore throat that does not go away, trouble swallowing, or a change in the voice. There may also be unusual bleeding, facial swelling, or trouble breathing. About 80% of head and neck cancer is due to the use of alcohol or tobacco. Other risk factors include *betel* quid, certain types of human papillomavirus, radiation exposure, certain workplace exposures, and Epstein-Barr virus. Head and neck cancers are most commonly of the squamous cell carcinoma type. In 2015 head and neck cancers globally affected more than 5.5 million people (mouth 2.4 million, throat 1.7 million, larynx 1.4 million) and resulted in more than 379,000 deaths (mouth 146,000, throat 127,400, larynx 105,900).

Lung cancer, also known as lung carcinoma, is a malignant lung tumor characterized by uncontrolled cell growth in tissues of the lung. The two main types are small-cell lung carcinoma (SCLC) and non-small-cell lung carcinoma (NSCLC). The vast majority (85%) of cases of lung cancer are due to long-term tobacco smoking. About 10-15% of cases occur in people who have never smoked. These cases are often caused by a combination of genetic factors and exposure to radon gas, asbestos, second-hand smoke, or other forms of air pollution. Treatment and long-term outcomes depend on the type of cancer, the stage, and the person's overall health. Most cases are not curable. Worldwide in 2012, lung cancer occurred in 1.8 million people and resulted in 1.6 million deaths.

Biomarkers are often used for cancer diagnosis, prognosis and epidemiology. Cancer biomarkers usually refer to a substance or process that is indicative of the presence of cancer in the body. A biomarker may be a molecule secreted by a tumor or a specific response of the body to the presence of cancer. Ideally, such biomarkers can be assayed in non-invasively collected bio fluids like blood or serum. While numerous challenges exist in translating biomarker research into the clinical space: a number of gene and protein based biomarkers have already been used at some point in patient care.

However, there still is a lack of reliable prognostic biomarkers in the current treatment of CRC, skin cancer, head and neck cancer or lung cancer. Up to now, the prognosis of these cancer patients depends highly on tumor staging that is defined by the degree of tumor penetration and the presence of distant metastasis. Nevertheless, patients with an identical TNM (tumor size/lymph node metastasis/distant metastasis staging system) stage often differ in terms of treatment response and survival outcome. Consequently, a better classification of the patients is needed to advise clinicians in choosing the best treatment options ultimately leading to increased patient survival. Accordingly, the technical problem underlying the present application is to comply with this need.

SUMMARY OF THE INVENTION

The inventors found two biomarkers, MYO5B and RAB8A, which can be used alone or in combination, with a high predictive and prognostic value in various cancers selected from the group consisting of colorectal cancer, skin cancer, head and neck cancer and lung cancer. This enables the physicians to choose the best treatment options in treating colorectal cancer, skin cancer, head and neck cancer or lung cancer in a subject using the biomarkers MYO5B and/or RAB8A and optionally in addition RAB9A, RAB10, RAB1A, RAB25, CDC42, RAC and/or RhoA.

Therefore, the present invention relates to a method for predicting clinical outcome for a subject diagnosed with colorectal cancer, skin cancer, head and neck cancer or lung cancer, comprising: (a) determining a normalized expression level of an RNA transcript of MYO5B and/or RAB8A, or an expression product thereof, in a biological sample comprising colorectal, skin, head and neck or lung cancer cells obtained from said subject; and (b) predicting the likelihood of a positive clinical outcome for said subject based on said normalized expression level, wherein an increased normalized expression of an RNA transcript of MYO5B and/or RAB8A, or an expression product thereof, is positively correlated with an increased likelihood of a positive outcome.

In a preferred embodiment, the method for predicting clinical outcome for a subject diagnosed with colorectal cancer, skin cancer, head and neck cancer or lung cancer further comprises (c) determining a normalized expression level of an RNA transcript of RAB9A, RAB10, RAB1A, RAB25, CDC42, RAC and/or RhoA or an expression product thereof, in a biological sample comprising colorectal, skin, head and neck or lung cancer cells obtained from said subject; and (d) predicting the likelihood of a positive clinical outcome for said subject based on said normalized expression level, wherein an increased normalized expression of an RNA transcript of RAB9A, RAB10, RAB11A, RAB25, CDC42, RAC and/or RhoA, or an expression product thereof, is positively correlated with an increased likelihood of a positive outcome.

In a preferred embodiment of the method for predicting clinical outcome for a subject diagnosed with colorectal cancer, skin cancer, head and neck cancer or lung cancer the clinical outcome is recurrence-free interval (RFI), overall survival (OS), disease-free survival (DFS), distant recurrence-free interval (DRFI), likelihood of occurrence of recrudescence, metastasis development or disease progression.

In a preferred embodiment of the method for predicting clinical outcome for a subject diagnosed with colorectal cancer, skin cancer, head and neck cancer or lung cancer the clinical outcome is benefit of said subject from therapy, such as chemotherapy, adjuvant chemotherapy, radiation therapy, targeted therapy or immunotherapy.

Preferably, the therapy is for a subject having stage I or II colorectal cancer, skin cancer, head and neck cancer or lung cancer.

The invention further relates to a method for predicting whether a subject has a predisposition to develop colorectal cancer, skin cancer, head and neck cancer or lung cancer, comprising: (a) determining a normalized expression level of an RNA transcript of MYO5B and/or RAB8A, or an expression product thereof, in a biological sample comprising colorectal, skin, head and neck or lung cells obtained from said subject; and (b) predicting the likelihood of a predisposition for said subject based on said normalized expression level, wherein an increased normalized expression of an RNA transcript of MYO5B and/or RAB8A, or an expression product thereof, is positively correlated with a decreased likelihood of a predisposition to develop colorectal, skin, head and neck or lung cancer.

In a preferred embodiment, the method for predicting whether a subject has a predisposition to develop colorectal cancer, skin cancer, head and neck cancer or lung cancer comprises further (c) determining a normalized expression level of an RNA transcript of RAB9A, RAB0, RAB1A, RAB25, CDC42, RAC and/or RhoA, or an expression product thereof, in a biological sample comprising colorectal, skin, head and neck or lung cells obtained from said subject; and (d) predicting the likelihood of a predisposition for said subject based on said normalized expression level, wherein an increased normalized expression of an RNA transcript of RAB9A, RAB10, RAB11A, RAB25, CDC42, RAC and/or RhoA, or an expression product thereof, is positively correlated with a decreased likelihood of a predisposition to develop colorectal, skin, head and neck or lung cancer.

The invention also relates to a method for aiding in the staging of colorectal cancer, skin cancer, head and neck cancer or lung cancer of a subject, comprising (a) determining a normalized expression level of an RNA transcript of MYO5B and/or RAB8A, or an expression product thereof, in a biological sample comprising colorectal, skin, head and neck or lung cancer cells obtained from said subject; and (b) predicting the cancer stage for said subject based on said normalized expression level, wherein a decreased normalized expression of an RNA transcript of MYO5B and/or RAB8A, or an expression product thereof, is positively correlated with a more advanced colorectal, skin, head and neck or lung cancer stage.

In a preferred embodiment, the method for aiding in the staging of colorectal cancer, skin cancer, head and neck cancer or lung cancer of a subject comprises further: (c) determining a normalized expression level of an RNA transcript of RAB9A, RAB10, RAB1A, RAB25, CDC42, RAC and/or RhoA, or an expression product thereof, in a biological sample comprising colorectal cancer cells obtained from said subject; and (d) predicting the cancer stage for said subject based on said normalized expression level, wherein a decreased normalized expression of an RNA transcript of RAB9A, RAB10, RAB1A, RAB25, CDC42, RAC and/or RhoA, or an expression product thereof, is positively correlated with a more advanced colorectal, skin, head and neck or lung cancer stage.

Preferably in the methods of the present invention, the normalized expression level of an RNA transcript of MYO5B and/or RAB8A or an expression product thereof, is determined using a nucleic acid amplification-based method, such as PCR, or a method for quantifying expression products, such as antibody-based methods, e.g. histochemistry, ELISA or mass spectrometry. Similarly it is preferred that the normalized expression level of an RNA transcript of RAB9A, RAB10, RAB11A, RAB25, CDC42, RAC and/or RhoA or an expression product thereof is determined using a nucleic acid amplification-based method, such as PCR, or a method for quantifying expression products, such as antibody-based methods, e.g. histochemistry, ELISA or mass spectrometry.

It is preferred that the normalized expression level of an RNA transcript of MYO5B and/or RAB8A is normalized relative to the expression level of an RNA transcript of at least one reference gene. Similarly it is preferred that the normalized expression level of an RNA transcript of RAB9A, RAB10, RAB11A, RAB25, CDC42, RAC and/or RhoA is normalized relative to the expression level of an RNA transcript of at least one reference gene.

It is preferred that the normalized expression level of an expression product of an RNA transcript of MYO5B and/or RAB8A is normalized relative to the expression level of an expression product of an RNA transcript of at least one reference gene. Similarly it is preferred that the normalized expression level of an expression product of an RNA transcript of RAB9A, RAB10, RAB11A, RAB25, CDC42, RAC and/or RhoA is normalized relative to the expression level of an expression product of an RNA transcript of at least one reference gene.

It is preferred that the normalized expression level is compared to gene expression data obtained from corresponding cancer reference samples in the method for predicting clinical outcome for a subject diagnosed with colorectal cancer, skin cancer, head and neck cancer or lung cancer or in the method for aiding in the staging of colorectal cancer, skin cancer, head and neck cancer or lung cancer of a subject.

It is preferred that the normalized expression level is compared to gene expression data obtained from healthy reference samples in the method for predicting whether a subject has a predisposition to develop colorectal cancer, skin cancer, head and neck cancer or lung cancer.

It is preferred that the subject referred to in the methods of the present invention is human.

It is preferred that the biological sample as referred to in the methods of the present invention is a fresh or frozen tissue sample, blood sample, laser-microdissected sample, paraffin-embedded and fixed sample.

The invention further relates to a method of determining whether a subject diagnosed with colorectal cancer, skin cancer, head and neck cancer or lung cancer should be subjected to further therapy following surgical resection of the cancer, comprising carrying out the method for predicting clinical outcome for a subject diagnosed with colorectal cancer, skin cancer, head and neck cancer or lung cancer or the method for aiding in the staging of colorectal cancer, skin cancer, head and neck cancer or lung cancer of a subject, wherein if the likelihood of positive clinical outcome of cancer is decreased, the patient is recommended further therapy following surgical resection.

Preferably, the further therapy is chemotherapy, adjuvant chemotherapy, radiation therapy, targeted therapy or immunotherapy.

The invention further relates to a kit for carrying out any of the methods of the invention, comprising means for determining a normalized expression level of an RNA transcript or an expression product thereof of MYO5B and, optionally at least one of RAB8A, RAB9A, RAB10, RAB11A, RAB25, CDC42, RAC or RhoA.

The invention further relates to a method for predicting clinical outcome for a subject diagnosed with colorectal cancer, skin cancer, head and neck cancer or lung cancer, comprising: (a) determining a normalized expression level of an RNA transcript of MYO5B and RAB8A, or an expression product thereof, in a biological sample comprising colorectal, skin, head and neck or lung cancer cells obtained from said subject; and (b) predicting the likelihood of a positive clinical outcome for said subject based on said normalized expression level, wherein an increased normalized expression of an RNA transcript of MYO5B and RAB8A, or an expression product thereof, is positively correlated with an increased likelihood of a positive outcome.

In one embodiment, the normalized expression level of an RNA transcript of only MYO5B and/or RAB8A, or an expression product thereof, is determined. In a further related embodiment, the normalized expression level of an RNA transcript of only MYO5B and RAB8A, or an expression product thereof, is determined.

DETAILED DESCRIPTION OF THE INVENTION

The following description includes information that may be useful in understanding the present invention. It is not an admission that any of the information provided herein is prior art or relevant to the presently claimed inventions, or that any publication specifically or implicitly referenced is prior art.

Described herein are methods for predicting clinical outcome for a subject diagnosed with colorectal cancer, skin cancer, head and neck cancer or lung cancer. Also described are methods for predicting whether a subject has a predisposition to develop such cancers as well as methods for aiding the staging of such cancers in a subject. In addition, a kit for carrying out these methods is described as well. These methods rely on the expression of MYO5B and/or RAB8A in a biological sample. The inventors have surprisingly found that MYO5B and/or RAB8A are good biomarkers for these methods. By analyzing further additional biomarkers like RAB9A, RAB10, RAB11A, RAB25, CDC42, RAC and/or RhoA the predictive value may be even more increased.

WO 2015/017537 discloses to 5, 10 or even more biomarkers, among them being MYO5B, for the diagnosis of colorectal cancer. WO 2012/149609 discloses a method for screening a subject for the onset, predisposition to the onset and/or progression of a colorectal neoplasm by screening for the expression of 79 biomarkers, amongst them MYO5B. EP 3009842 also discloses a panel of 55 biomarkers including MYO5B for risk assessment of colorectal cancer recurrence. WO 2009/075799 allegedly discloses MYO5B, but only among dozens of other biomarkers.

Figure 1:
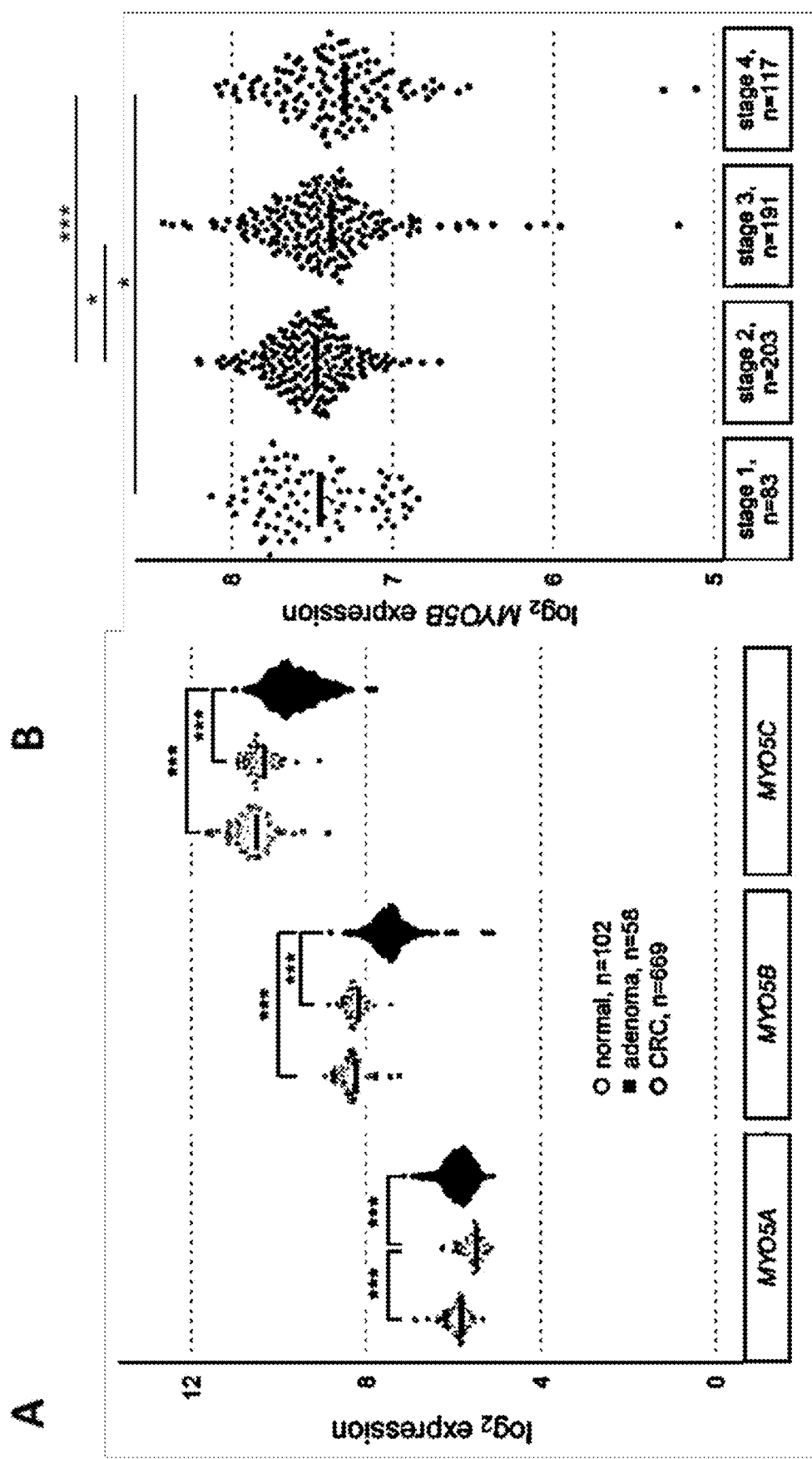
FIG. 1: Bioinformatic analysis reveals the potential use of MYO5B as a diagnostic biomarker for CRC. A. Dot plot showing the $\log_2$ FC values of the Myosin V family genes in adenoma and CRC samples compared to healthy colorectal mucosa samples in a meta-analysis of different CRC datasets including 829 patients. Bar represents the mean expression intensity (***$p<0.001$, t-test corrected for multiple testing). B. MYO5B expression according to the different TNM stages in the meta-analysis. Bar represents the mean expression intensity (*$p<0.05$, ***$p<0.001$ t-test corrected for multiple testing). C. ROC curves with corresponding AUC values for MYO5A, MYO5B, and MYO5C when comparing CRC and healthy samples in the meta-analysis. Distribution of gene expression values for healthy and CRC samples are shown in the insets.
Figure 1:
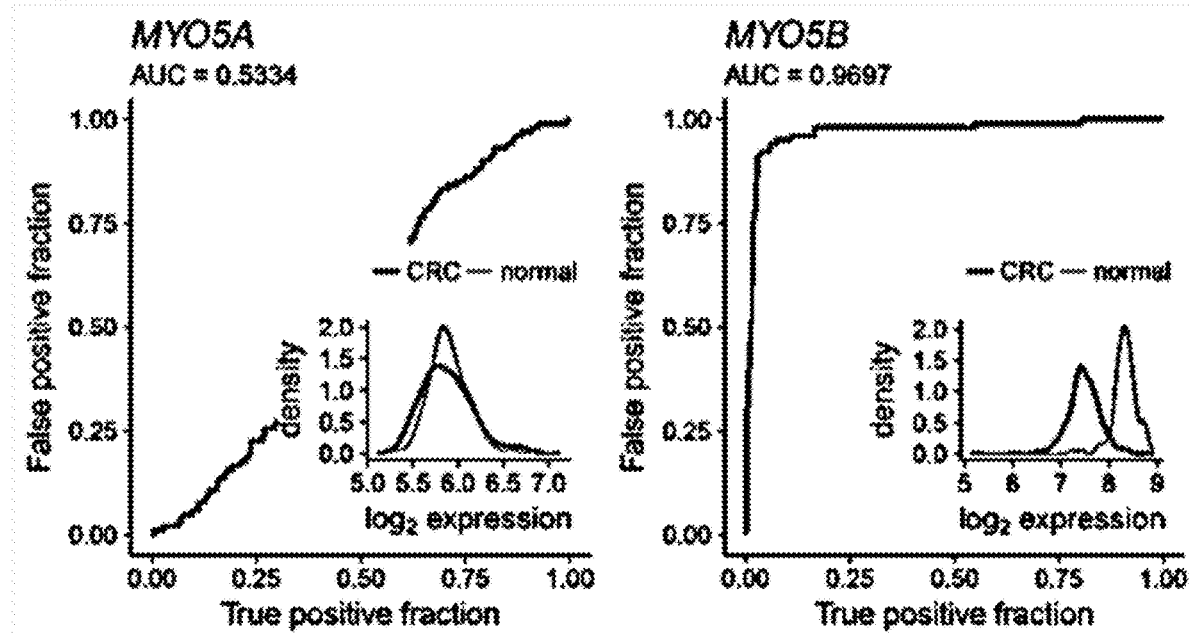
Figure 1:
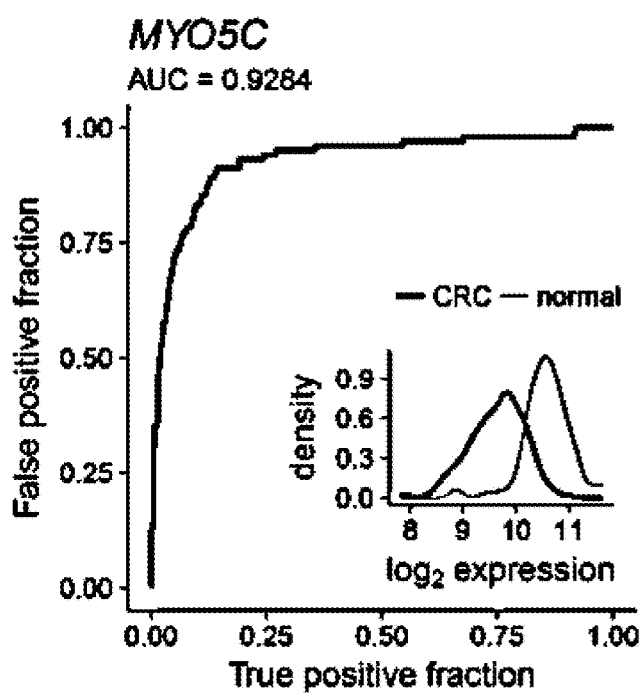
Figure 2:
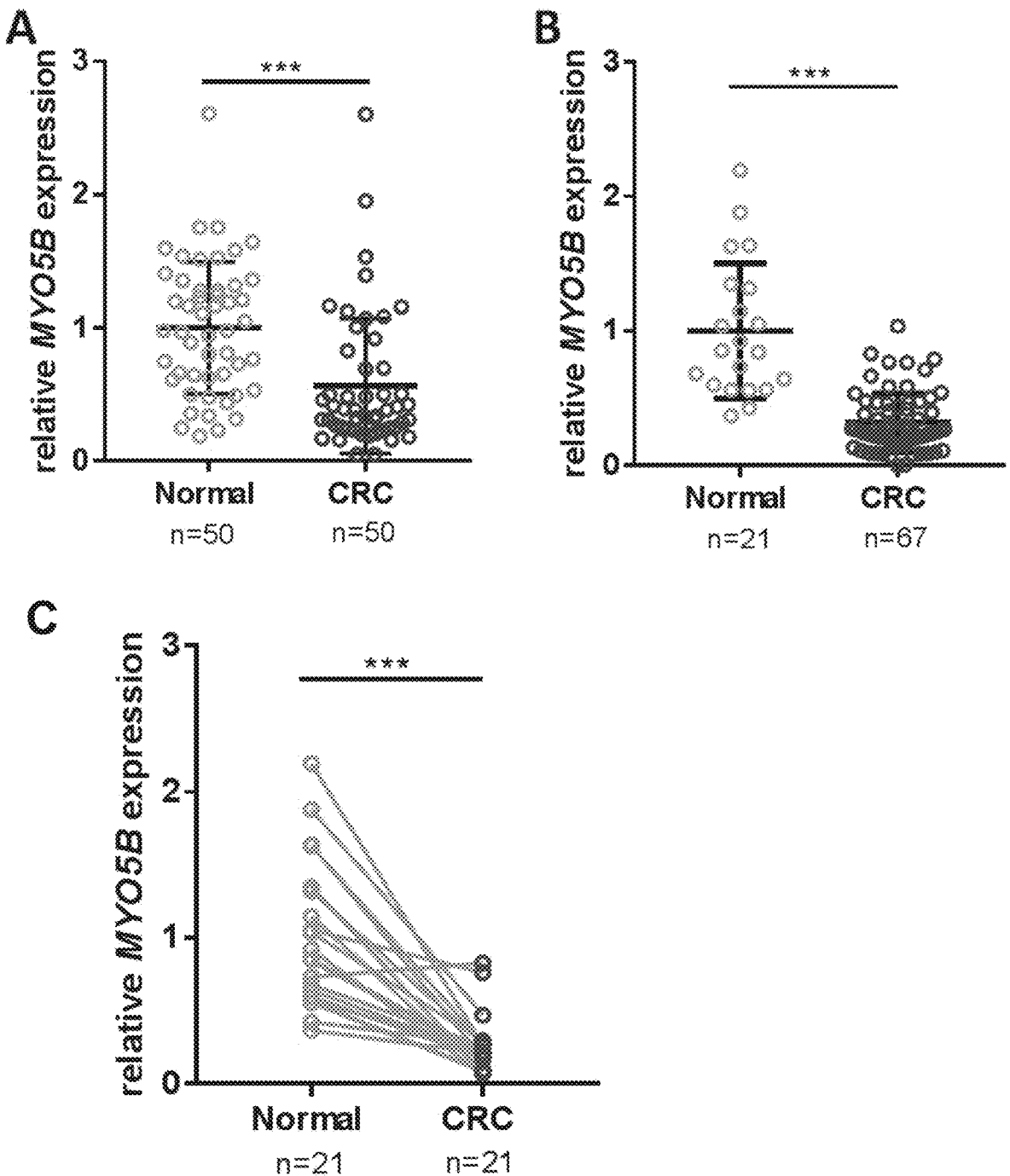
FIG. 2: Down-regulation of Myo5B on mRNA and protein levels in human CRC. A. MYO5B mRNA levels in bulk tissue of matched tumor (CRC, n=50) and non-tumor (Normal, n=50) samples from CRC patients. Data is presented as mean±SD (*$p<0.001$, paired t-test). B. MYO5B mRNA levels in laser-microdissected tumor (CRC, n=67) and non-tumor (Normal, n=21) samples. Data is presented as mean±SD (*$p<0.001$, unpaired t-test). C. In 20 out of 21 paired microdissected tumor samples, MYO5B mRNA levels were higher in non-tumor tissue compared to the matched tumor sample (*$p<0.001$, paired t-test). D. Immunohistochemical staining of 56 paired TMA's of CRC patients. Left panel: Representative image of MYO5B immunostaining on a section that contains normal (bottom) and cancerous tissue (top). Staining was mainly cytoplasmic and showed the expected accumulation of MYO5B at the apical brush border of normal enterocytes, as well as in tumor cells in which differentiation was still preserved. Scale bar corresponds to 200 μm. Right panel: Quantification of MYO5B staining of matched tumor (CRC; n=56) and non-tumor (Normal; n=56) samples scored according to the staining intensity of MYO5B-positive cells (0=no signal, 1=mild signal, 2=moderate signal and 3=strong signal). Two sections of cancerous as well as normal counterpart tissue were scored per patient and the mean value was considered. Data is presented as mean SD (*$p<0.001$, paired t-test). E. Representative pictures (left panel) and quantification (right panel) of immunohistochemical staining of MYO5B in patient samples of different TNM stages. Data is presented as mean t SD ($p<0.01$, *$p<0.001$, unpaired t-test). Scale bar corresponds to 200 μm F. MYO5B scoring of TMA samples after classification according to their histological grade. Data is presented as mean±SD; unpaired t-test *$p<0.05$, $p<0.01$ and *$p<0.001$.
Figure 2:
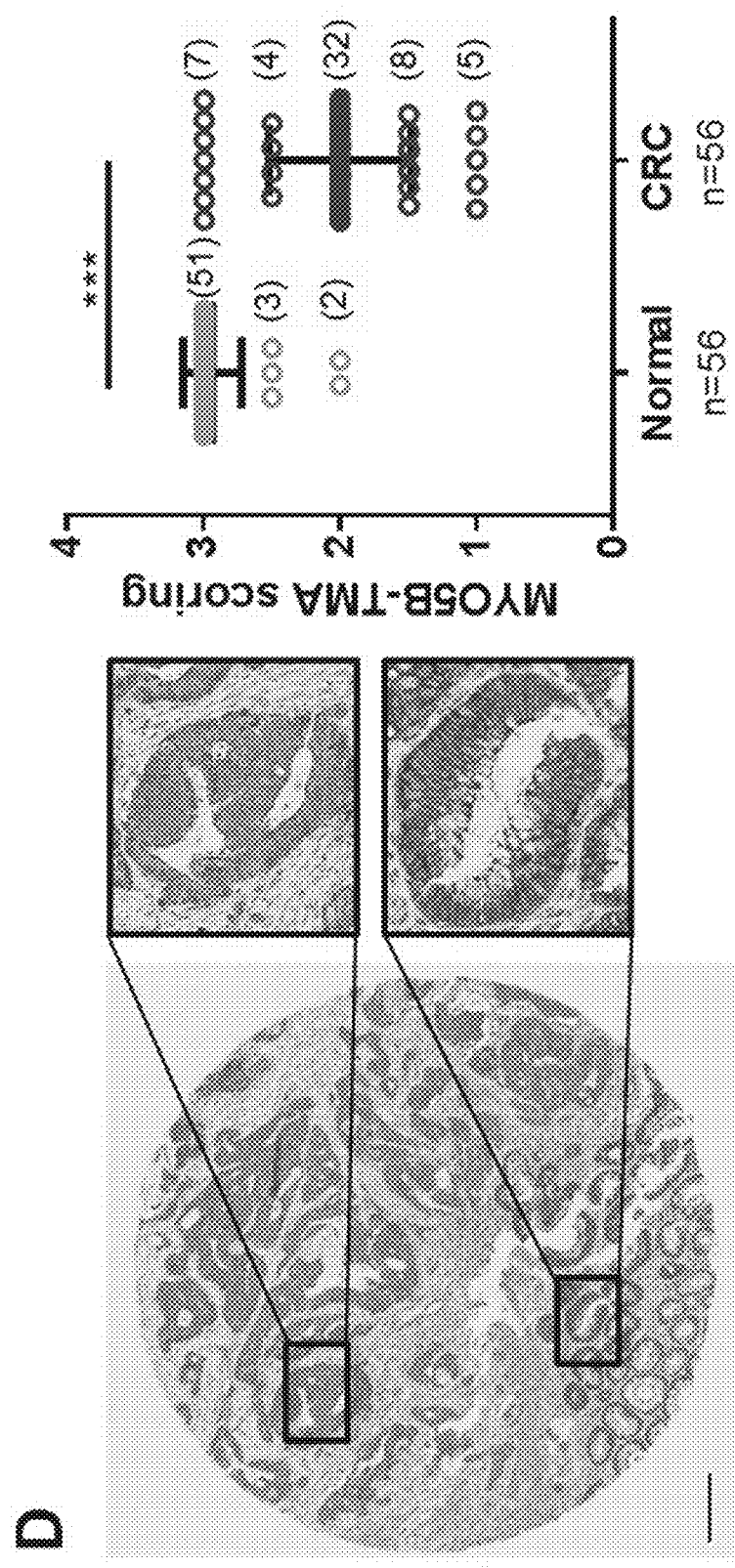
Figure 2:
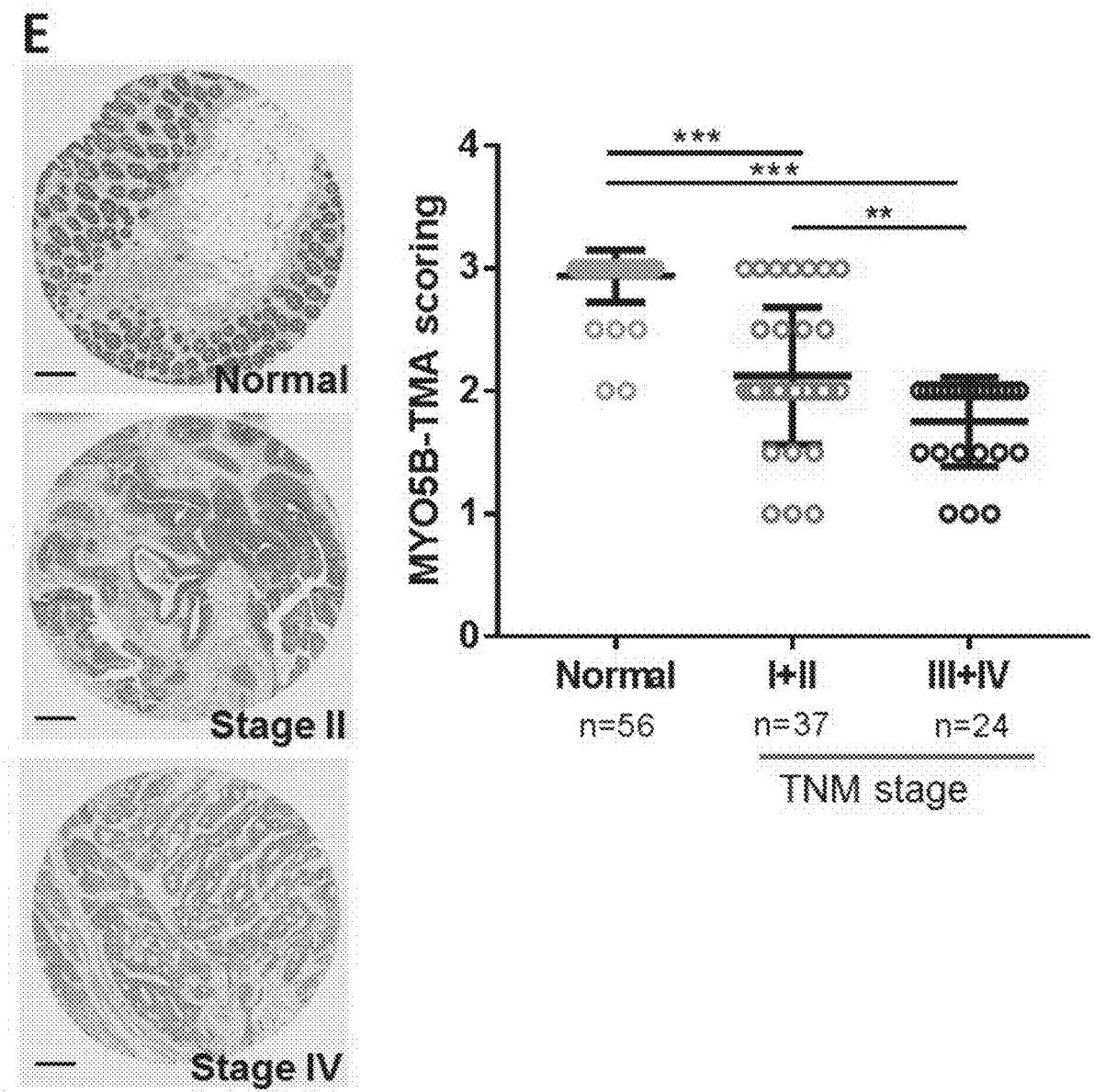
Figure 2:
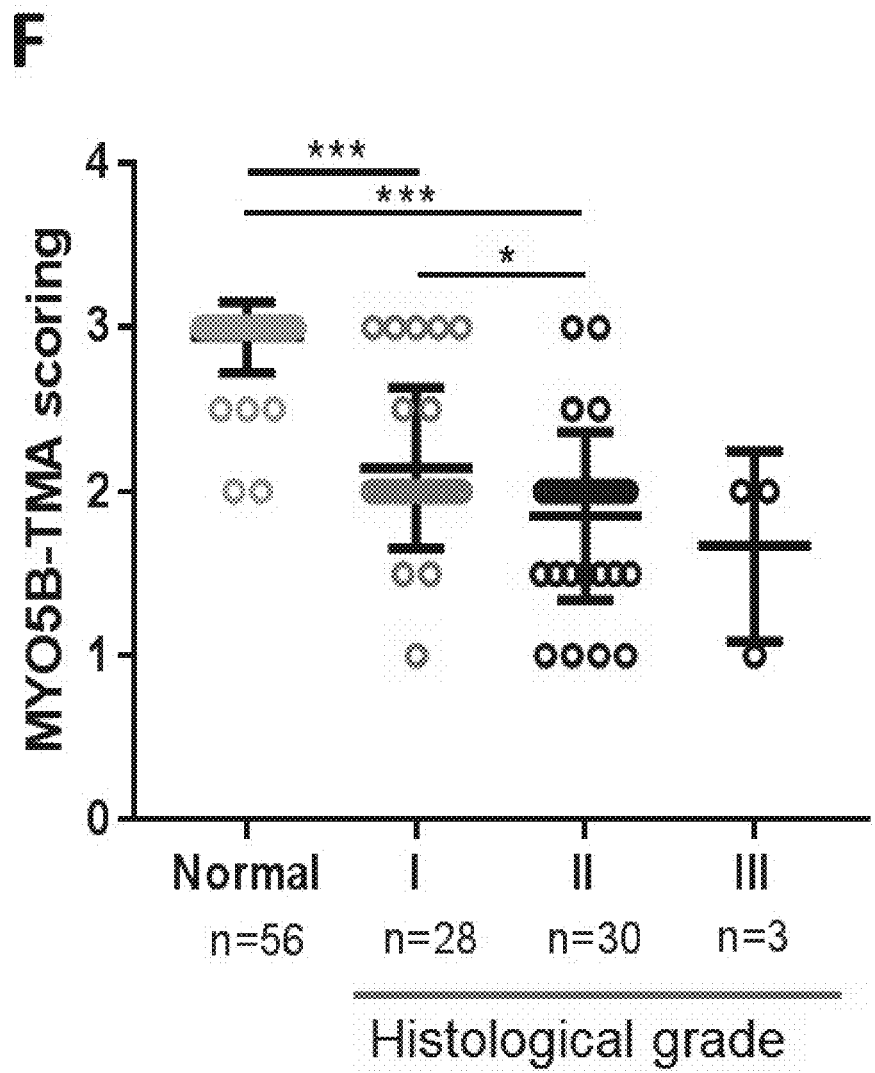
Figure 3:
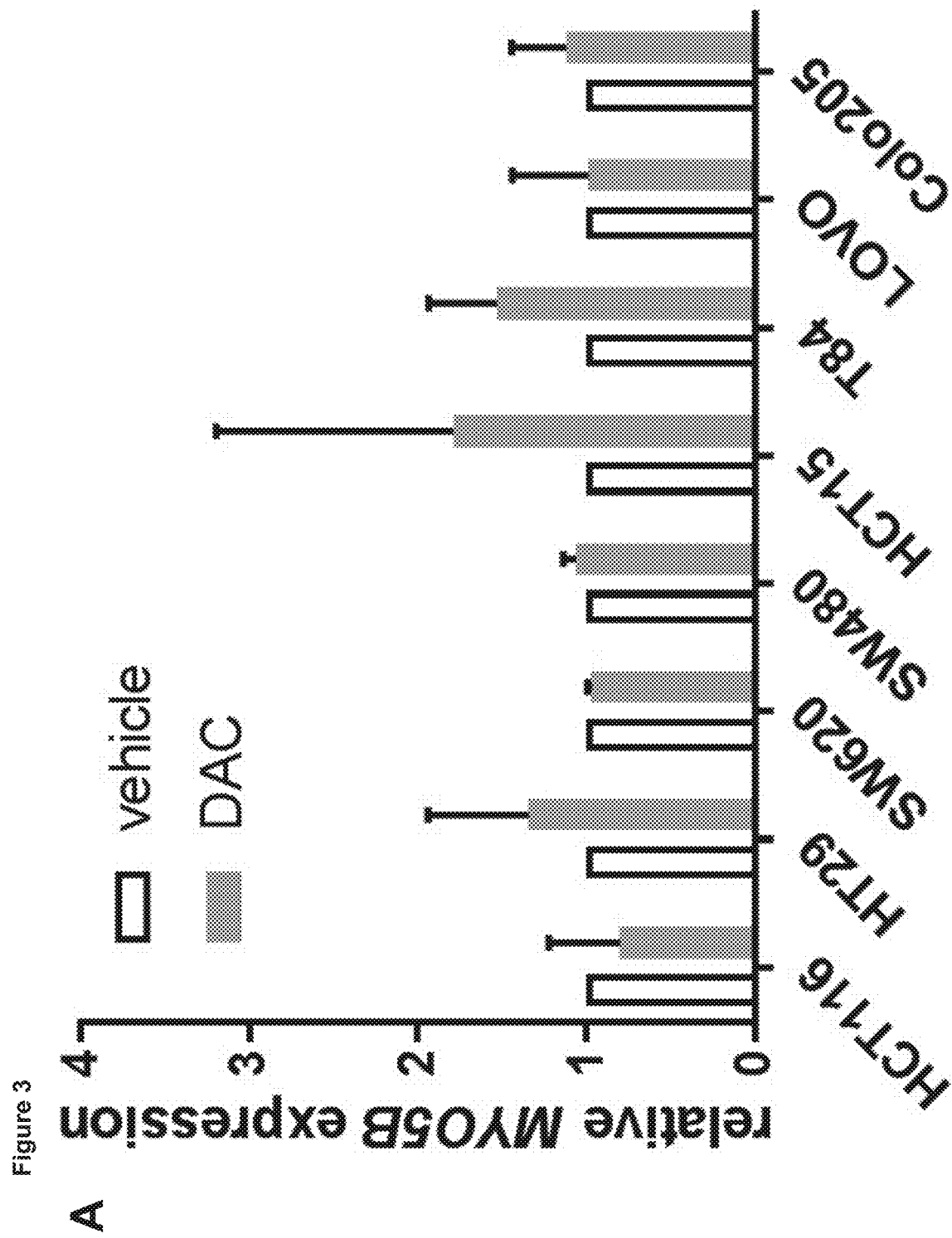
FIG. 3: Reduced expression of MYO5B is not due to methylation in CRC. A. 5-aza-dC (DAC) treatment does not increase basal MYO5B expression in colon cancer cell lines. Data is representative of 2-4 independent experiments and presented as mean t SD. B. Methylation pattern analyzed by mass array technology of eight CRC cell lines as well as eight tumor samples and four matching non-tumor counterparts. Each analyzed cytosine is represented by a dot; cytosines with values below 5% were considered as non-methylated.
Figure 3:
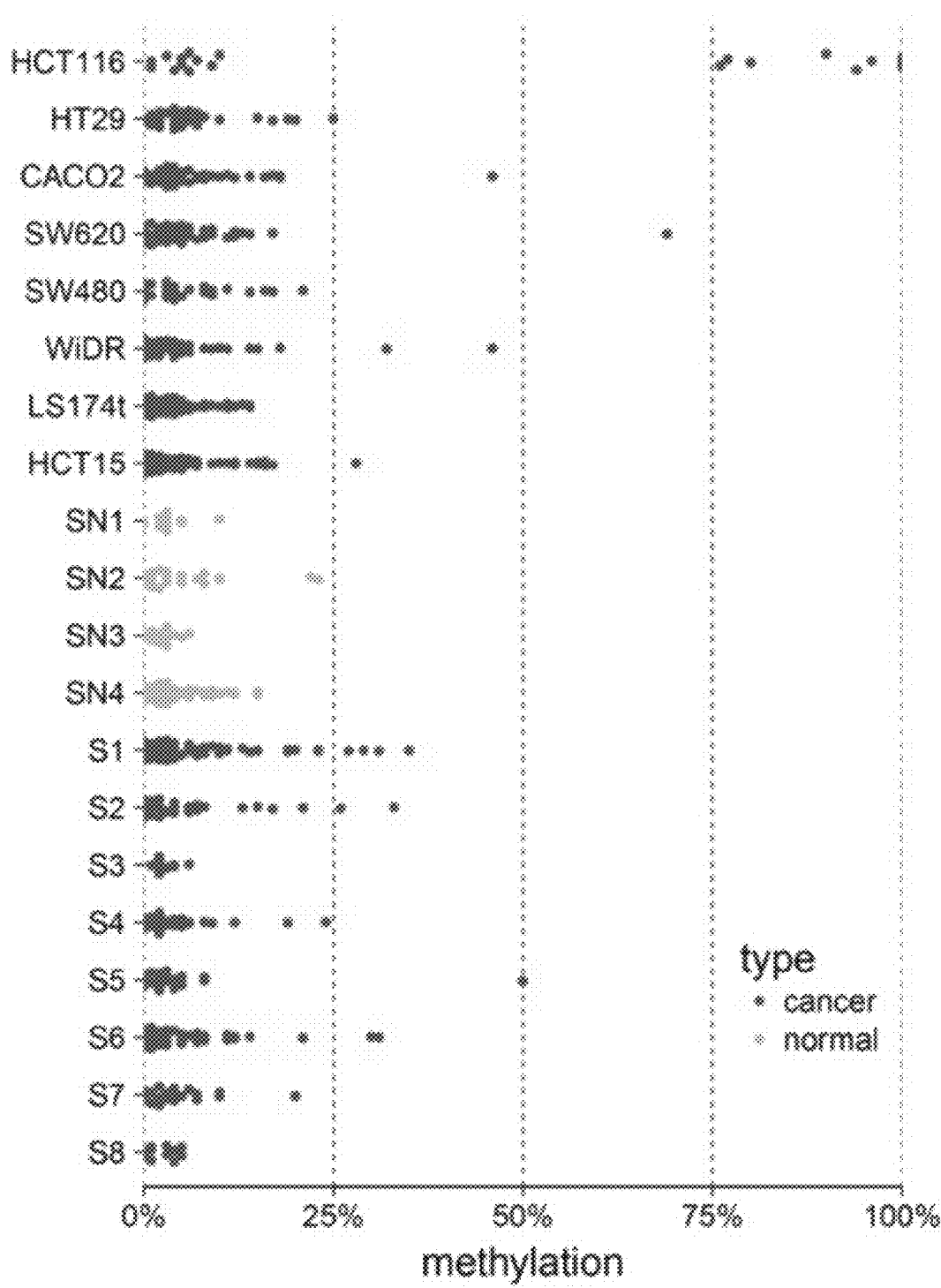

The inventors of the present invention could show that there is a significant inverse correlation between the expression of MYO5B and a CRC diagnosis (FIGS. 1A and 1C, FIG. 2A-D). There is also an inverse correlation between the expression of MYO5B and the progression of CRC expressed in the grade of the disease (FIG. 1B, FIGS. 2E and 2F). It could also be shown that methylation of MYO5B gene does not play a role (FIG. 3).

Figure 4:
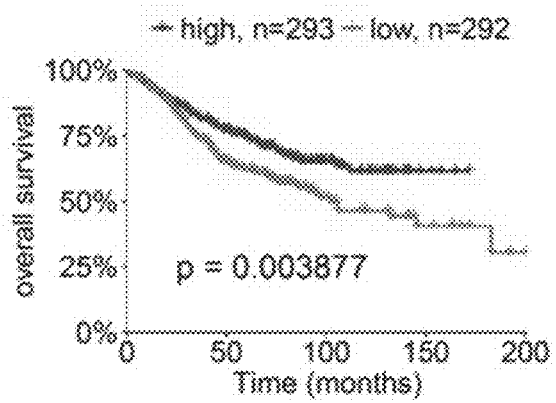
FIG. 4: MYO5B is a prognostic biomarker in CRC patients. A-B. Overall (A) and relapse-free (B) survival in 585 CRC patients stratified according to MYO5B expression in the GSE39582 dataset. C-D. Overall (C) and relapse-free (D) survival in early stage (stage I and II) CRC patients stratified according to MYO5B expression in the GSE39582 dataset. E. Disease-free survival curves for patients with "high" and "low" expression levels of MYO5B in an independent dataset (GSE24551) covering 160 patients. F. Metastasis-free survival based on "high" or "low" expression of MYO5B in a dataset (GSE28814) containing clinical data on metastasis from 125 CRC patients. Patient numbers and associated p-values are indicated in the figures.
Figure 4:
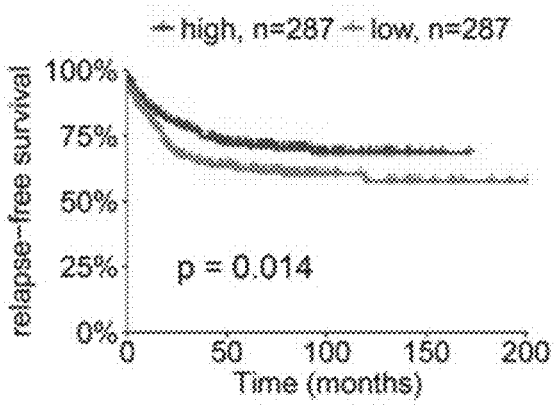
Figure 4:
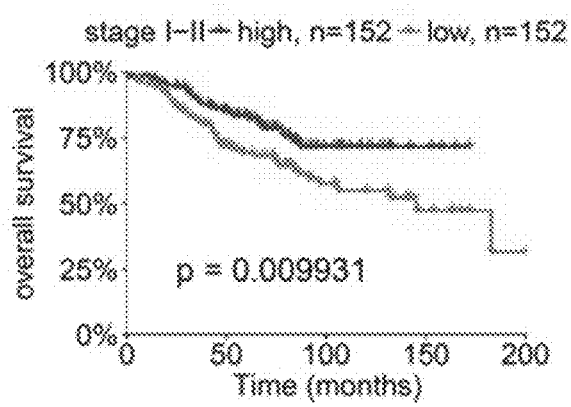
Figure 4:
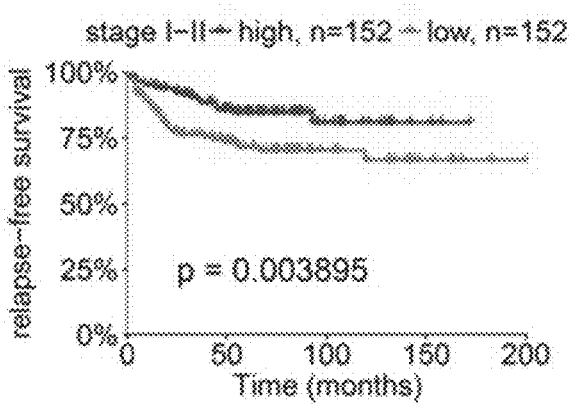
Figure 4:
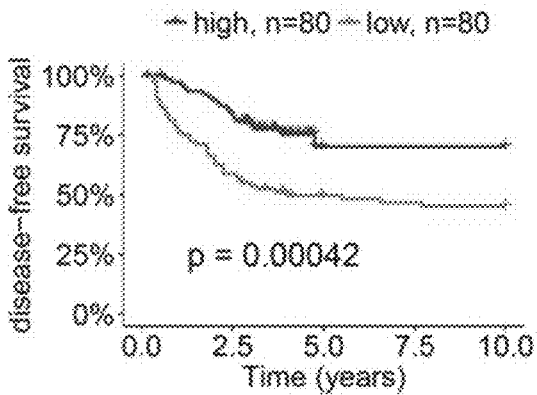
Figure 4:
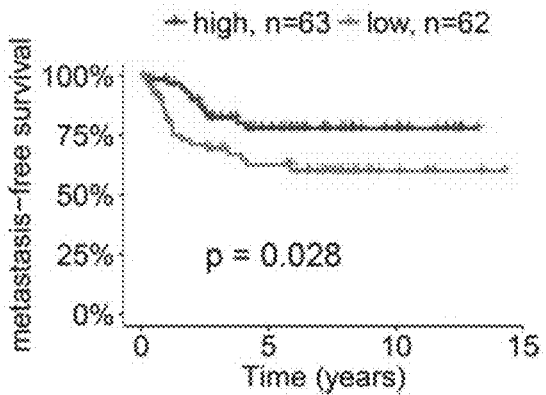
Figure 5:
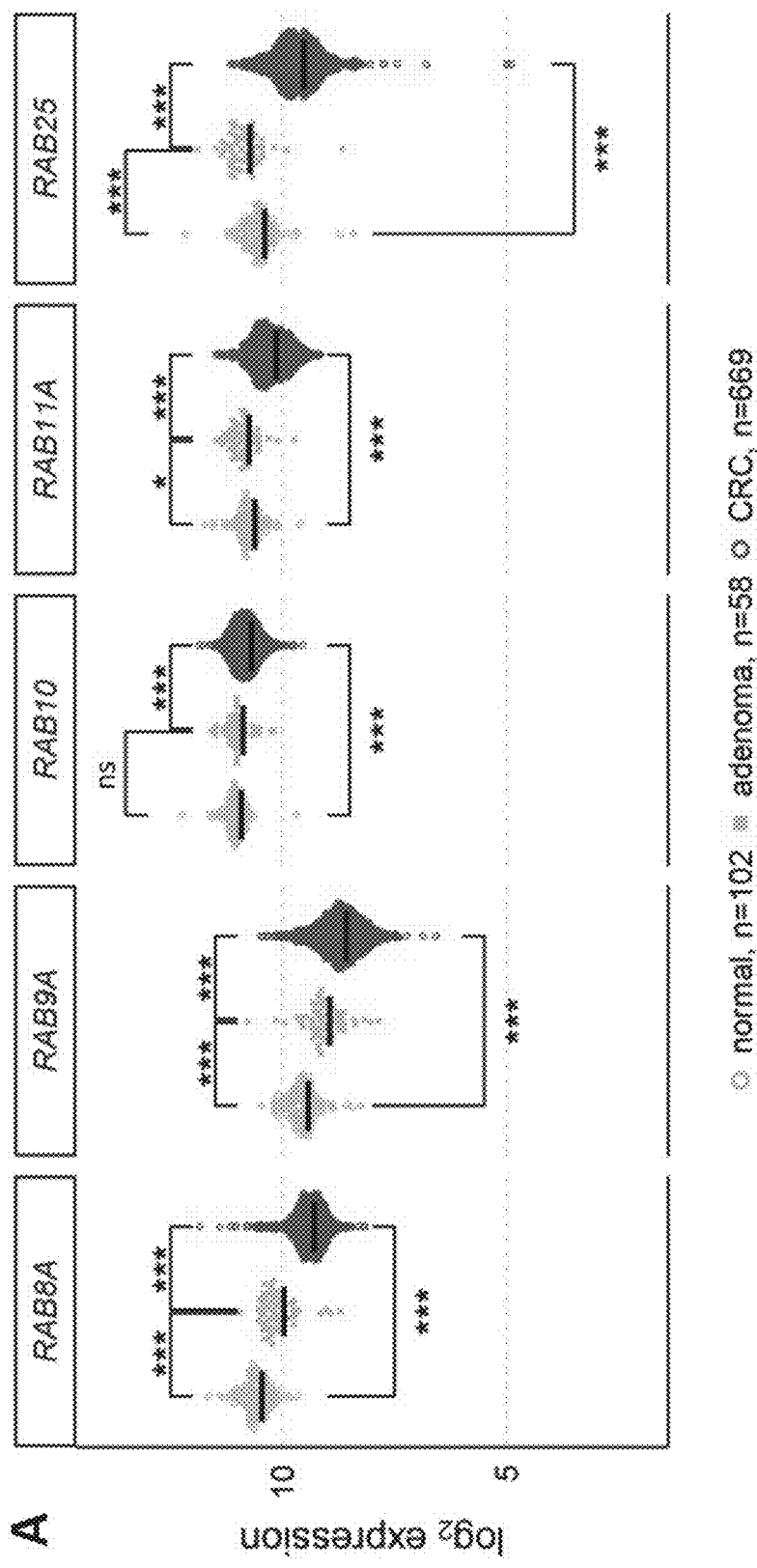
FIG. 5: RAB family members RAB8A and RAB25 are downregulated in CRC. A. Dot plot showing the $\log_2$ expression intensities of different RAB genes in adenoma and CRC samples compared to unmatched healthy colorectal mucosa samples in a meta-analysis of different CRC datasets including 829 patients. Bar represents the mean expression intensity (*$p<0.05$, ***$p<0.001$, t-test corrected for multiple testing). B. ROC curves with corresponding AUC values for RAB genes when classifying CRC and healthy patients in the meta-analysis. Distribution of gene expression values for normal and CRC samples are shown in the insets. C. RAB8A and RAB25 expression levels in bulk tissue of matched tumor (CRC, n=50) and non-tumor (Normal, n=50) samples from CRC patients. Data is presented as mean±SD; *p<0.05, ***p<0.001, paired t-test.
Figure 5:
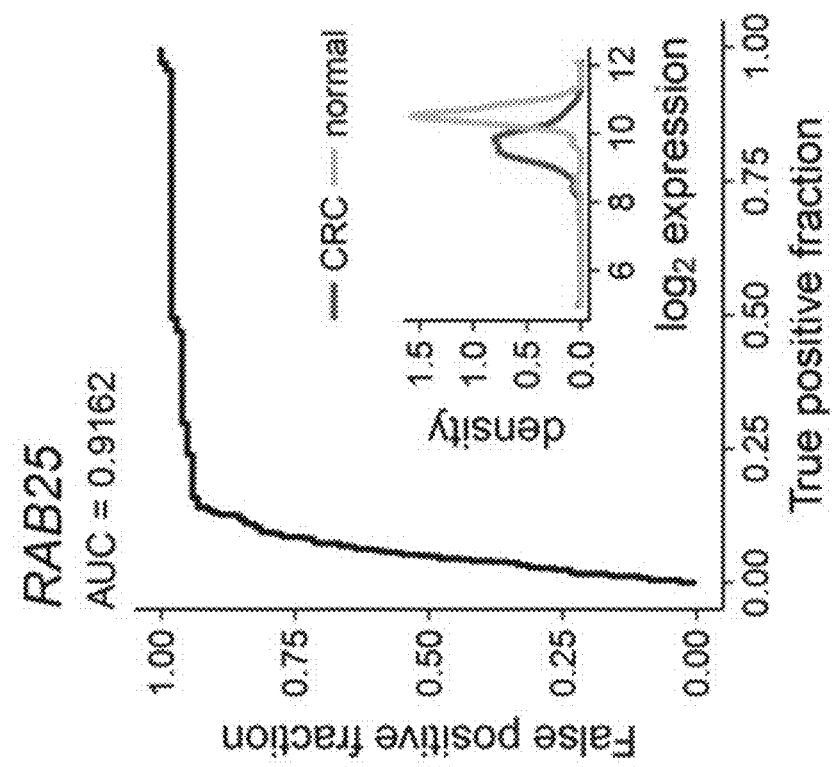
Figure 5:
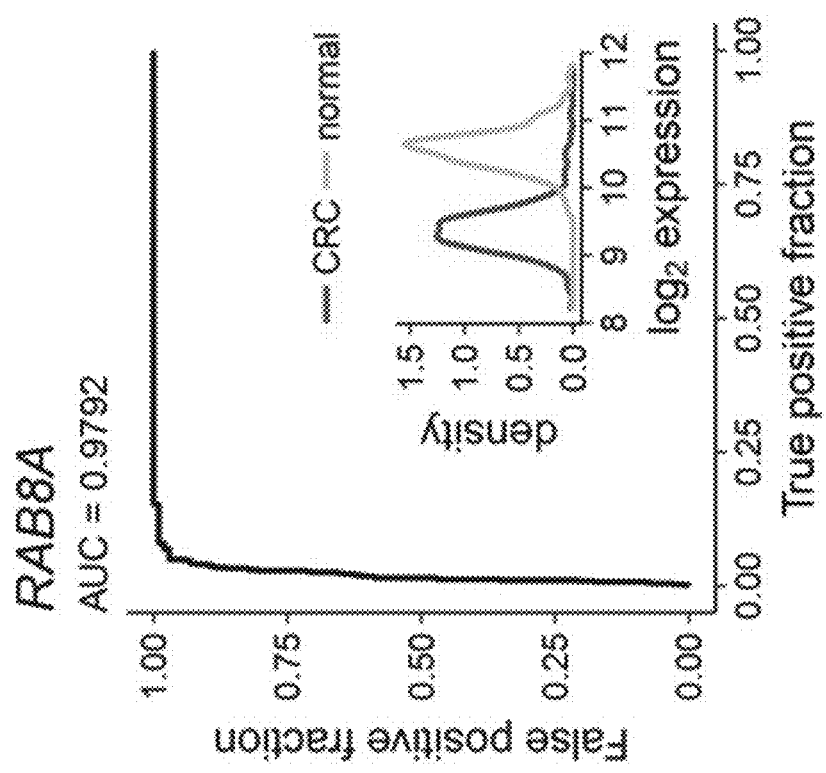
Figure 5:
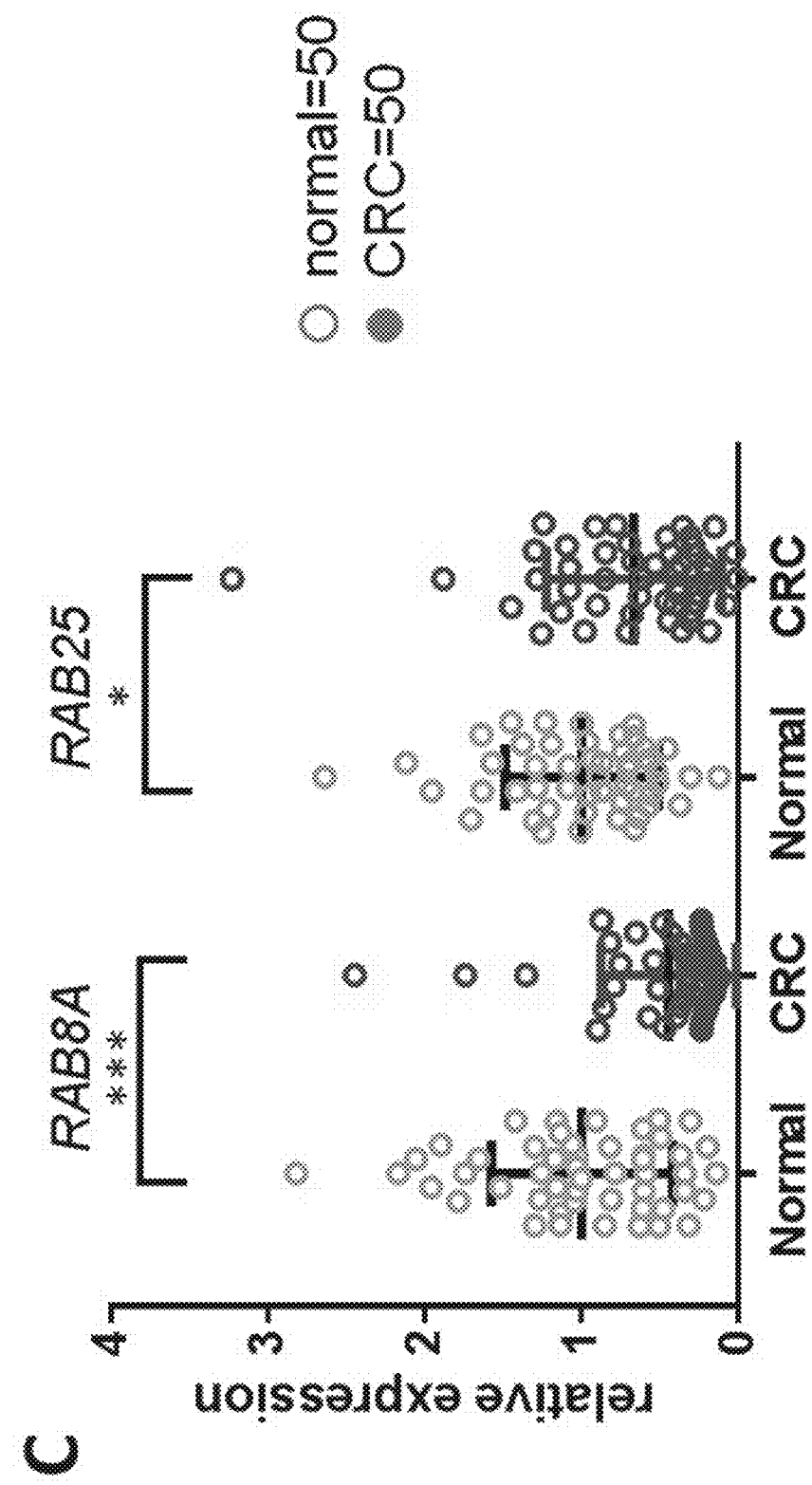
Figure 6:
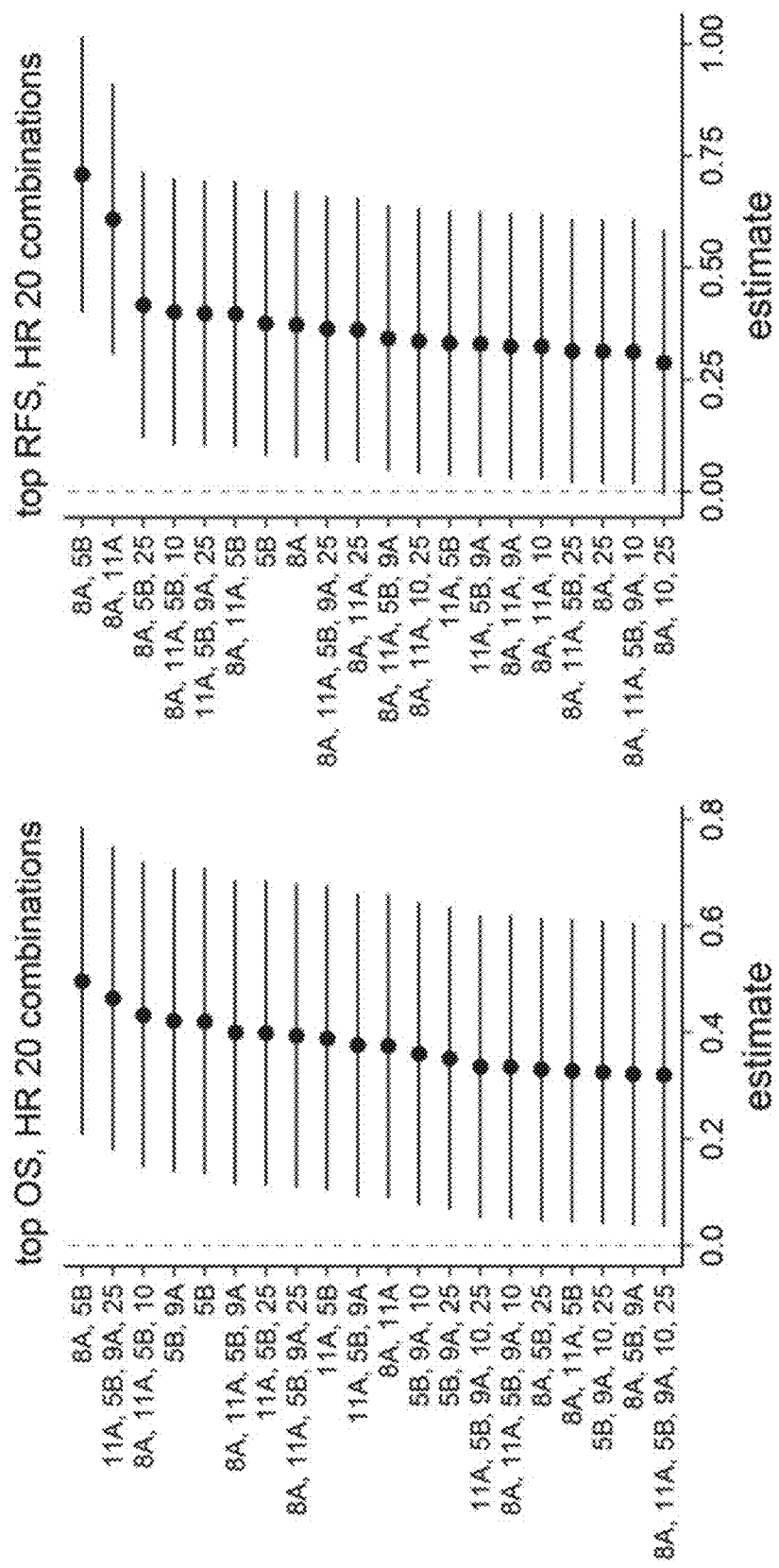
FIG. 6: The combination of MYO5B expression with its adapter protein RAB8A improves the prognostic power of MYO5B in CRC. A. Top 20 significant combinatorial signatures between MYO5B and different genes of the RAB family for overall (OS, left) and relapse-free (RFS, right) survival in 585 CRC patients of the GSE39582 dataset. Because of space issues, MYO as well as RAB have been omitted from the name description and only the last letters are shown. B. Overall (left) and relapse-free (right) survival in 585 CRC patients stratified according to their combined MYO5B and RAB8A expression signature in the GSE39582 dataset. The dotted line represents the MYO5B signature alone, whereas continuous lines represent the combinatorial signature. Patient numbers as well as their p-values are indicated in the figure.
Figure 6:
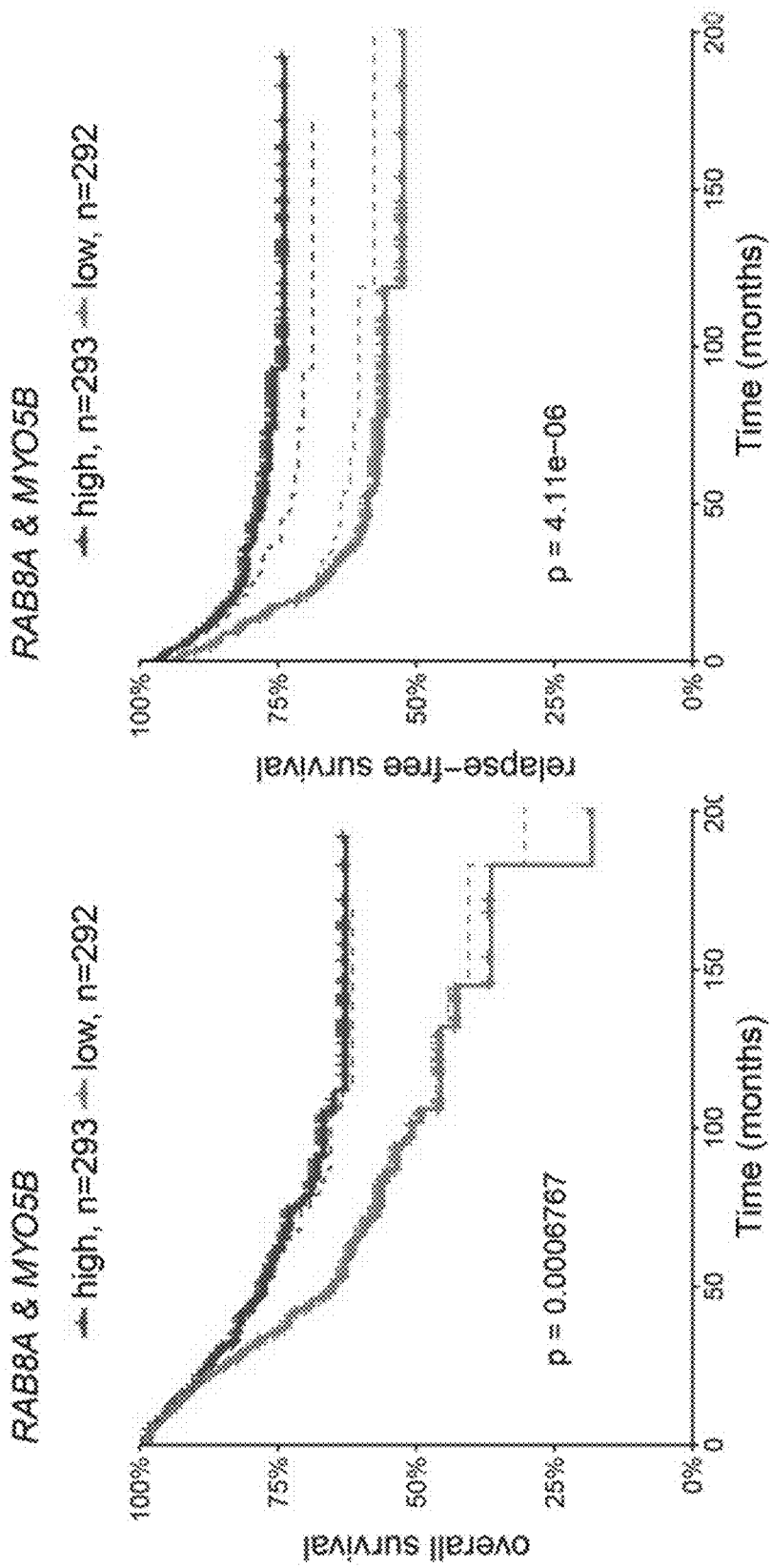
Figure 8:
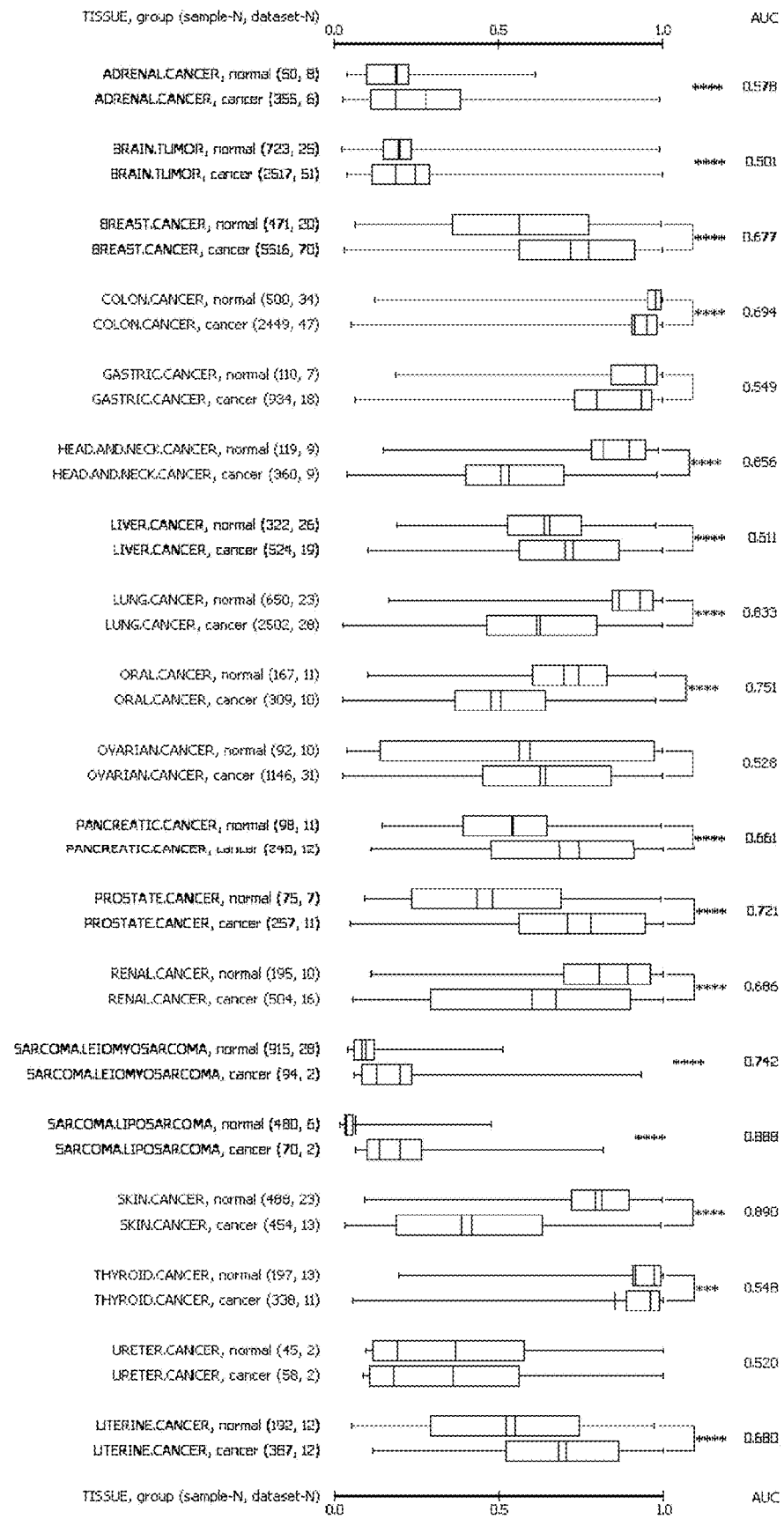
FIG. 8: MYO5B expression is also significantly reduced in tumour tissues for lung, head and neck and skin cancer. An analysis of the expression of MYO5B in various cancer tissues compared to normal tissue was performed by using the gene expression compendium Oncopression (Lee et al., 2017). Sample numbers are indicated in brackets.
Figure 9:
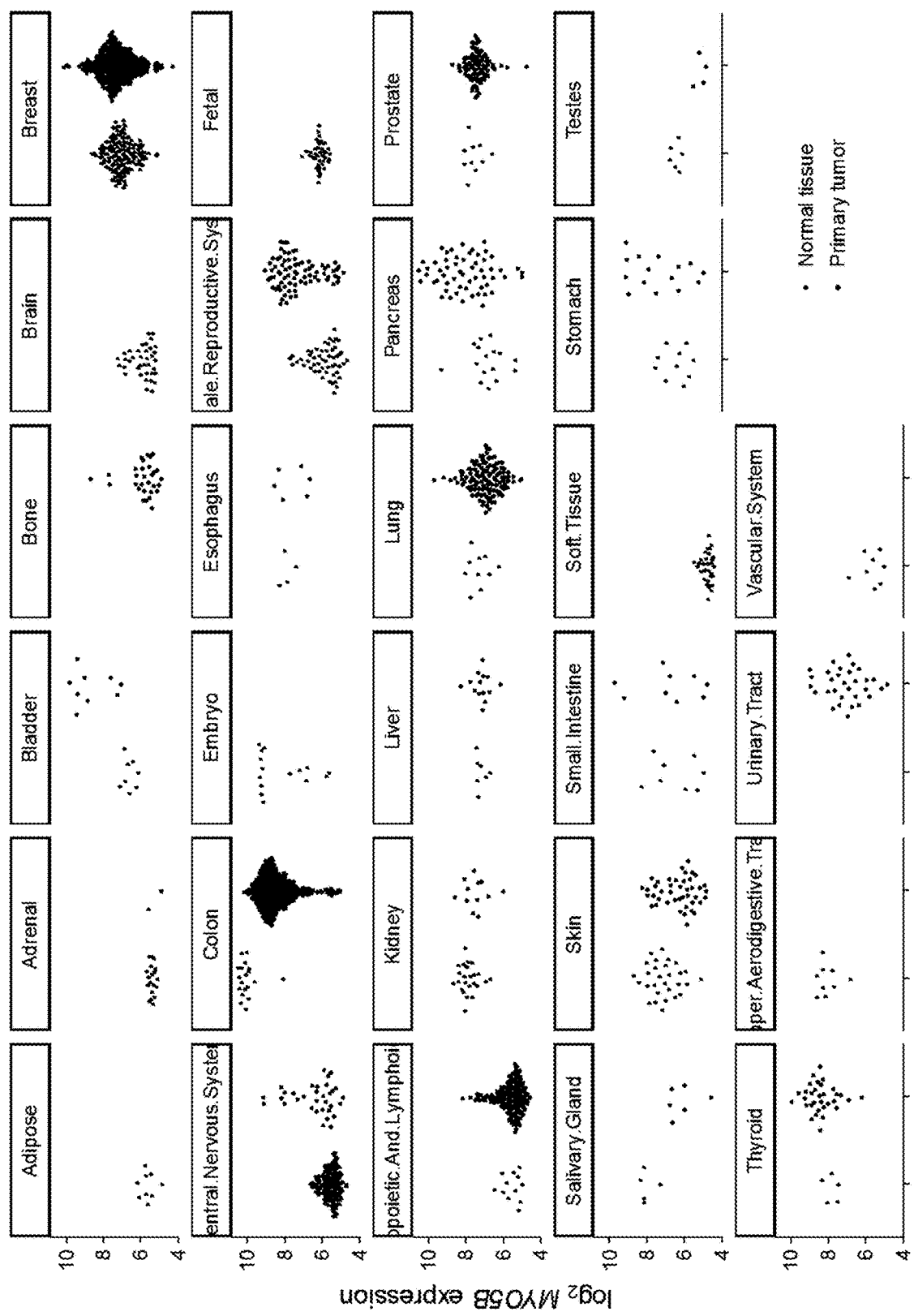
FIG. 9: MYO5B expression is also significantly reduced in tumour tissues for lung, and skin cancer in a second, independent dataset (TCGA dataset). Dot plot showing the log 2 FC values for MYO5B in various cancer types for normal control tissue (light) and tumour tissue (dark).
Figure 10:
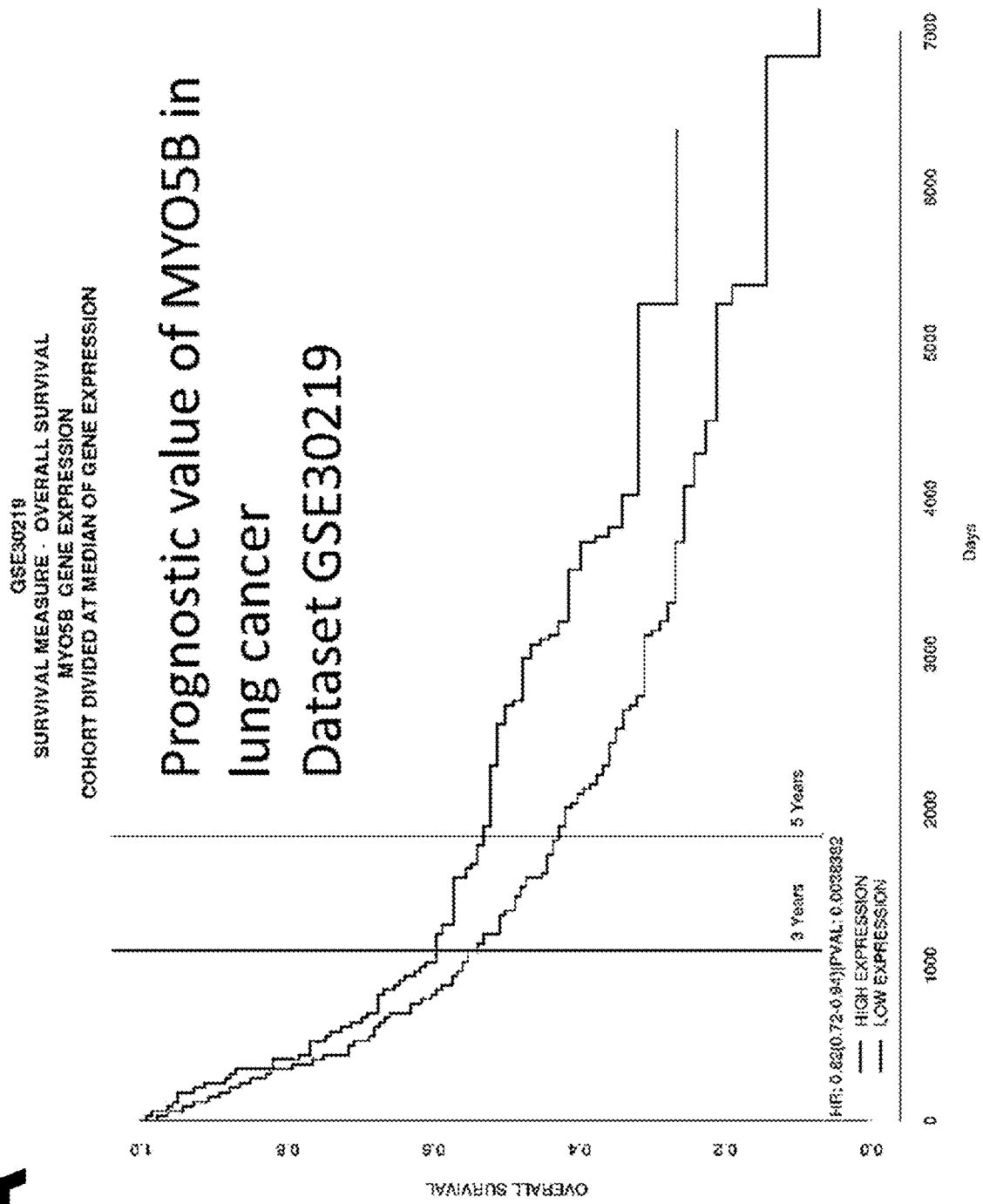
FIG. 10: MYO5B is a prognostic biomarker in lung, head and neck and skin cancer patients. Overall survival stratified according to MYO5B expression for lung cancer patients (GSE30219 dataset; p-value: 0.0038382) (A), head and neck cancer patients (GSE65858 dataset; p-value: 0.0051631) (B) and skin cancer patients (TCGA dataset; p-value: 0.015468) (C).
Figure 10:
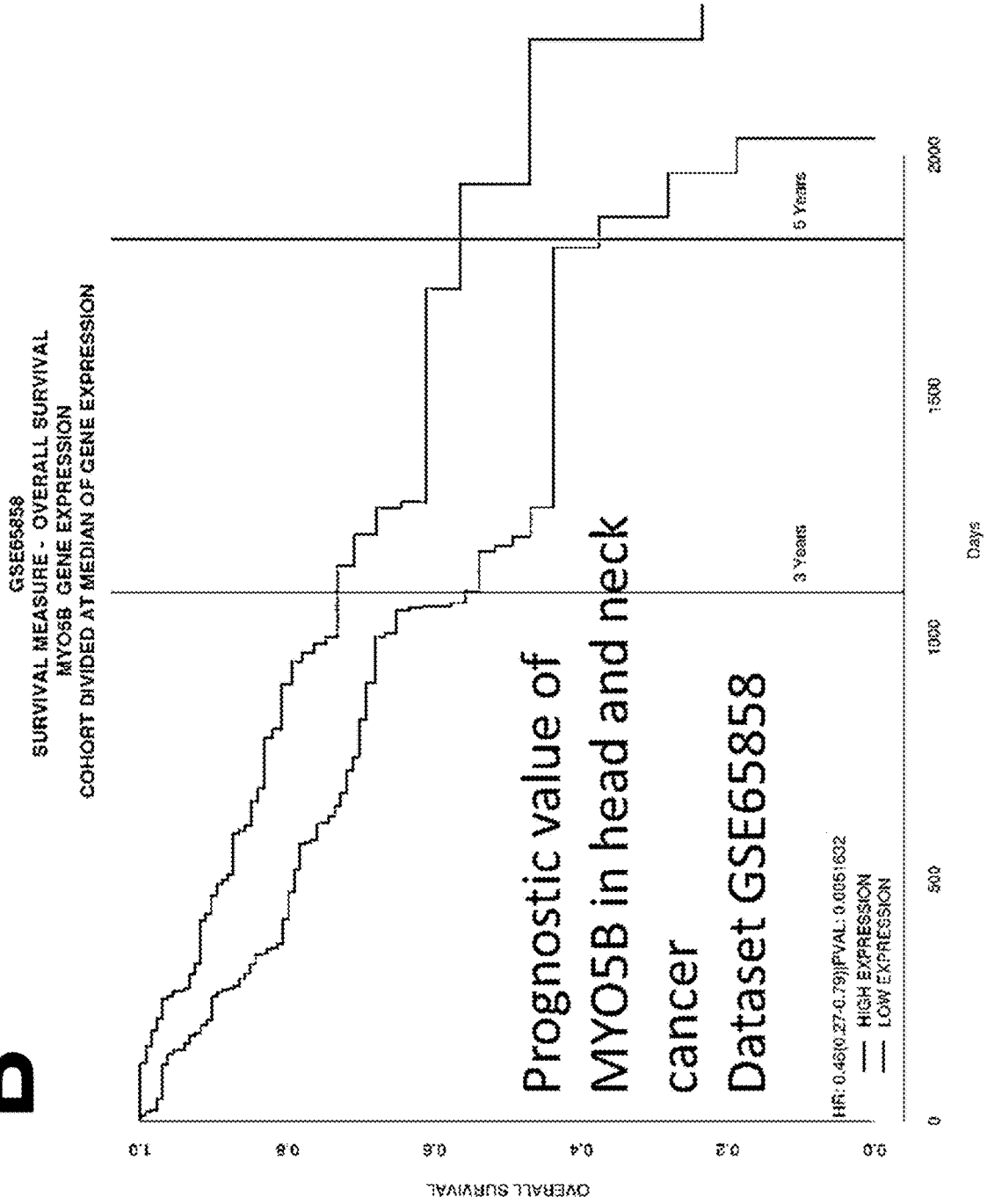
Figure 10:
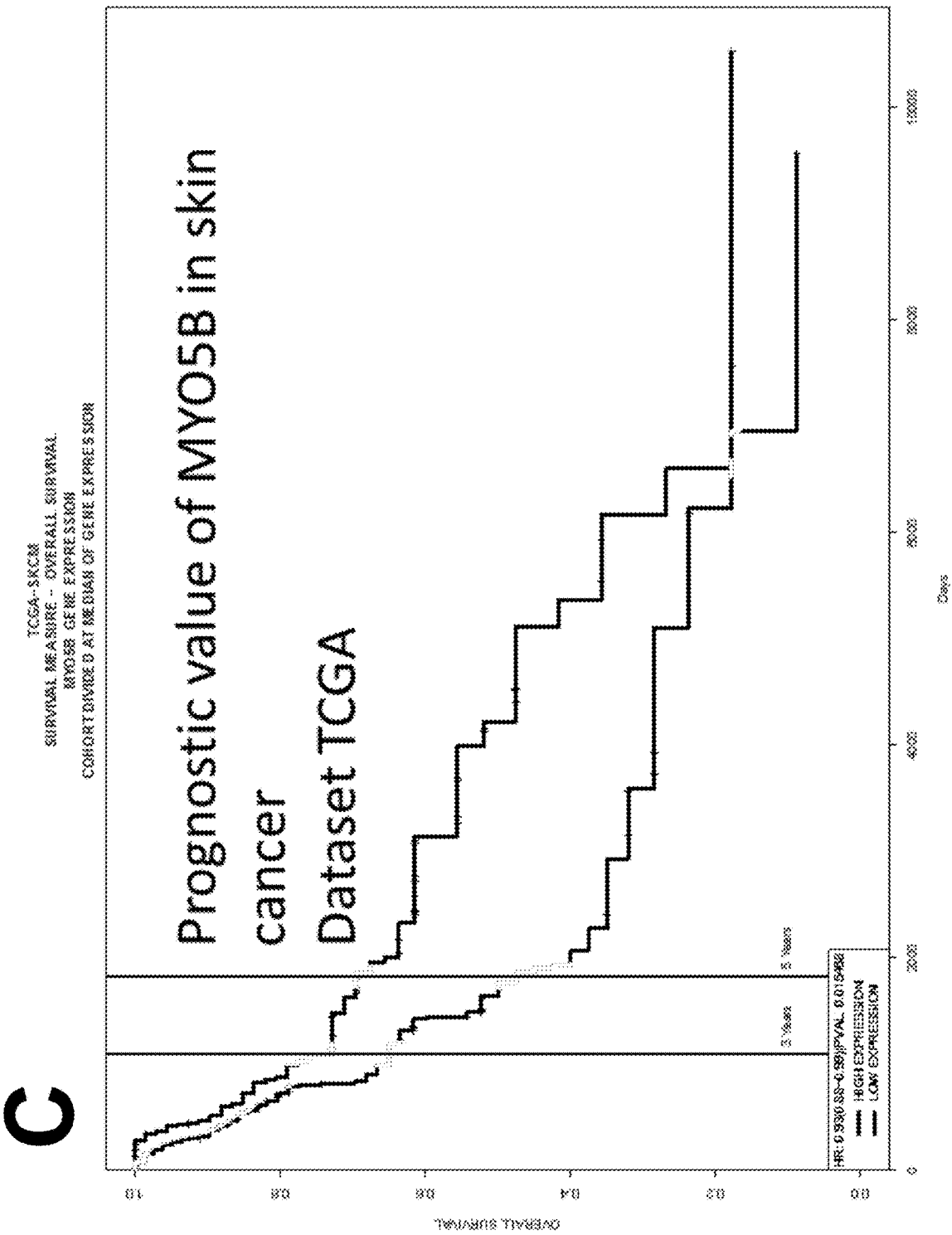

The inventors could further show that there is a highly significant inverse correlation between the clinical outcome of human patients diagnosed with colorectal cancer and the expression of MYO5B (FIG. 4). The same is true for RAB8A alone (FIG. 5) or in combination with MYO5B (FIG. 6). As shown in FIG. 8 and FIG. 9, the expression of MYO5B is also reduced in head and neck cancer, lung cancer and skin cancer and as shown in FIG. 10, the clinical outcome of lung cancer, head and neck cancer and skin cancer can also be predicted by MYO5B expression levels.

Figure 11:
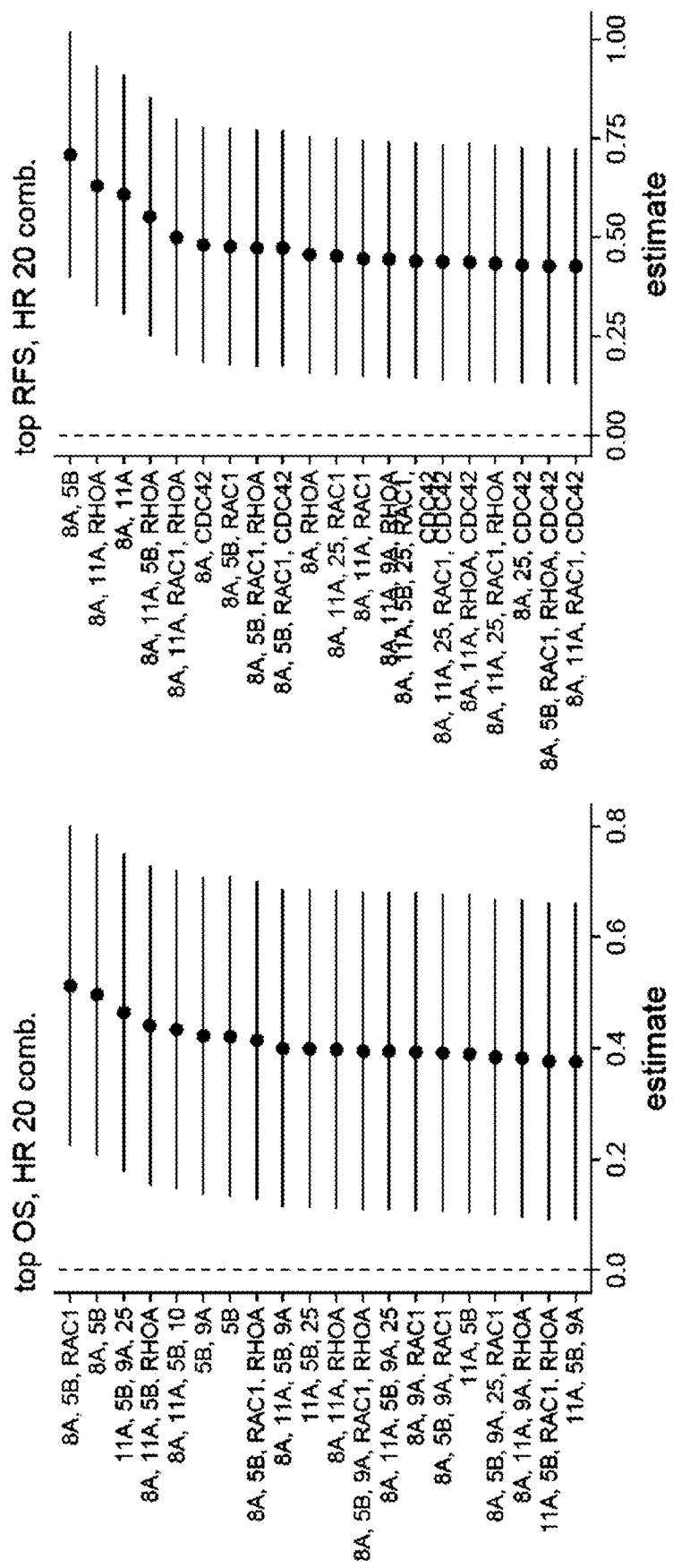
FIG. 11: Top combinatorial expression signatures between MYO5B, the RAB proteins, CDC42, RAC and RHOA for overall survival and relapse-free survival in colorectal cancer. Top 20 significant combinatorial signatures (of a total of 511 tested) obtained for overall (OS, left) and relapse-free (RFS, right) survival in 585 CRC patients of the GSE39582 dataset. Because of space issues, MYO as well as RAB have been omitted from the name description and only the last letters are shown.

As shown in FIGS. 6A and 11, there are also other combinations with additional biomarkers to MYO5B and/or RAB8A, which show a high correlation to the clinical outcome. Those additional biomarkers are RAB9A, RAB10, RAB11A, RAB25, CDC42, RAC and/or RhoA. Thus, the predictive value of MYO5B and/or RAB8A may be increased by additional analysis of those additional biomarkers.

Accordingly, the present invention relates to a method for predicting clinical outcome for a subject diagnosed with colorectal cancer, skin cancer, head and neck cancer or lung cancer, comprising: (a) determining a normalized expression level of an RNA transcript of MYO5B and/or RAB8A, or an expression product thereof, in a biological sample comprising colorectal, skin, head and neck or lung cancer cells obtained from said subject; and (b) predicting the likelihood of a positive clinical outcome for said subject based on said normalized expression level, wherein an increased normalized expression of an RNA transcript of MYO5B and/or RAB8A, or an expression product thereof, is positively correlated with an increased likelihood of a positive outcome.

Alternatively, the invention relates to a method for predicting clinical outcome for a subject diagnosed with colorectal cancer, skin cancer, head and neck cancer or lung cancer, comprising: (a) determining a normalized expression level of an RNA transcript of MYO5B and/or RAB8A, or an expression product thereof, in a biological sample comprising colorectal, skin, head and neck or lung cancer cells obtained from said subject; and (b) predicting the likelihood of a positive clinical outcome for said subject based on said normalized expression level, wherein a decreased normalized expression of an RNA transcript of MYO5B and/or RAB8A, or an expression product thereof, is positively correlated with an increased likelihood of a negative outcome.

The method for predicting clinical outcome for a subject diagnosed with colorectal cancer, skin cancer, head and neck cancer or lung cancer, comprising may also comprise the analysis of additional biomarkers like RAB9A, RAB10, RAB11A, RAB25, CDC42, RAC and/or RhoA. Accordingly, the method for predicting clinical outcome for a subject diagnosed with colorectal cancer, skin cancer, head and neck cancer or lung cancer may further comprise the steps: (c) determining a normalized expression level of an RNA transcript of RAB9A, RAB10, RAB11A, RAB25, CDC42, RAC and/or RhoA or an expression product thereof, in a biological sample comprising colorectal, skin, head and neck or lung cancer cells obtained from said subject; and (d) predicting the likelihood of a positive clinical outcome for said subject based on said normalized expression level, wherein an increased normalized expression of an RNA transcript of RAB9A, RAB10, RAB11A, RAB25, CDC42, RAC and/or RhoA, or an expression product thereof, is positively correlated with an increased likelihood of a positive outcome.

Alternatively, the method for predicting clinical outcome for a subject diagnosed with colorectal cancer, skin cancer, head and neck cancer or lung cancer may further comprise the steps: (c) determining a normalized expression level of an RNA transcript of RAB9A, RAB10, RAB11A, RAB25, CDC42, RAC and/or RhoA or an expression product thereof, in a biological sample comprising colorectal, skin, head and neck or lung cancer cells obtained from said subject; and (d) predicting the likelihood of a positive clinical outcome for said subject based on said normalized expression level, wherein an decreased normalized expression of an RNA transcript of RAB9A, RAB10, RAB11A, RAB25, CDC42, RAC and/or RhoA, or an expression product thereof, is positively correlated with an decreased likelihood of a positive outcome.

As outlined herein, it is also sufficient to analyze only the expression of MYO5B and/or RAB8A. Accordingly, the invention also relates to a method for predicting clinical outcome for a subject diagnosed with colorectal cancer, skin cancer, head and neck cancer or lung cancer comprising: (a) determining a normalized expression level of an RNA transcript of only MYO5B and/or RAB8A, or an expression product thereof, in a biological sample comprising colorectal, skin, head and neck or lung cancer cells obtained from said subject; and (b) predicting the likelihood of a positive clinical outcome for said subject based on said normalized expression level, wherein an increased normalized expression of an RNA transcript of MYO5B and/or RAB8A, or an expression product thereof, is positively correlated with an increased likelihood of a positive outcome.

The term "predicting clinical outcome" when used herein, refers to the likelihood that a patient will have a particular clinical outcome, whether positive or negative. The predictive methods of the present invention can be used clinically to make treatment decisions by choosing the most appropriate treatment modalities for any particular subject. The predictive methods of the present invention are valuable tools in predicting if a subject is likely to respond favorably to a treatment regimen, such as further therapy following surgical resection. The prediction may include prognostic factors.

The term "RNA transcript" as used herein refers to the RNA transcription products of a gene, including, for example, mRNA, an unspliced RNA, a splice variant mRNA, a microRNA, and a fragmented RNA. An RNA transcript of the present invention has at least 50, at least 100, at least 150, at least 200, at least 250 or at least 300 nucleotides.

The term "expression product" as used herein relates to the product that has been produced by cells according to a template. Preferably, the template is an RNA transcript. Preferably, the expression product is a protein, which has been synthesized by a ribosome according to an RNA transcript template. One or more of the amino acids in the polypeptide may be modified, for example, by the addition of a chemical entity such as a carbohydrate group, a hydroxyl group, a phosphate group, a farnesyl group, an isofarnesyl group, a fatty acid group. A protein, peptide, or polypeptide may be just a fragment of a naturally occurring protein or peptide, as long as it exhibits biological activity as defined herein. An expression product of the present invention has at least 10, at least 20, at least 30, at least 40, at least 50 or at least 75 amino acids.

MYO5B, RAB8A, RAB9A, RAB10, RAB11A, RAB25, CDC42, RAC and/or RhoA as defined herein are herein referred to as "biomarkers" of the invention and are characterized by corresponding SEQ IDs. These SEQ IDs comprise the encoding human gene and a corresponding protein sequence.

A variety of sequence based alignment methodologies, which are well known to those skilled in the art, can be used to determine identity among sequences. These include, but are not limited to, the local identity/homology algorithm of Smith, F. and Waterman, M. S. (1981) Adv. Appl. Math. 2: 482-89, homology alignment algorithm of Peason, W. R. and Lipman, D. J. (1988) Proc. Natl. Acad. Sci. USA 85: 2444-48, Basic Local Alignment Search Tool (BLAST) described by Altschul, S. F. et al. (1990) J. Mol. Biol. 215: 403-10, or the Best Fit program described by Devereau, J. et al. (1984) Nucleic Acids. Res. 12: 387-95, and the FastA and TFASTA alignment programs, preferably using default settings or by inspection. Alternatively, an alignment may be done manually/visually for amino acids sequences as follows: the percent identity between an amino acid sequence in question and the amino acid sequence of MYO5B, RAB8A, RAB9A, RAB10, RAB11A, RAB25, CDC42, RAC or RhoA as defined herein is determined by pairwise alignment in such a way that the maximum identity is obtained between both amino acid sequences. The identical amino acid residues between both amino acid sequences are counted and divided by the total number of residues of the amino acid sequence of MYO5B, RAB8A, RAB9A, RAB10, RAB11A, RAB25, CDC42, RAC and/or RhoA (including positions that do not contain amino acid residues, e.g. one or more gaps) yielding the percentage of identity. A similar method applies to nucleotide sequences: An alignment may be done manually/visually for nucleotide sequences as follows: the percent identity between an nucleotide sequence in question and the nucleotide sequence of MYO5B, RAB8A, RAB9A, RAB10, RAB11A, RAB25, CDC42, RAC or RhoA as defined herein is determined by pairwise alignment in such a way that the maximum identity is obtained between both nucleotide sequences. The identical nucleotides between both nucleotide sequences are counted and divided by the total number of nucleotides of the nucleotide sequence of MYO5B, RAB8A, RAB9A, RAB10, RAB11A, RAB25, CDC42, RAC and/or RhoA (including positions that do not contain nucleotides, e.g. one or more gaps) yielding the percentage of identity.

MYO5B, also known as myosin VB, unconventional myosin-Vb, is a member of the myosin V protein family. It may be involved in vesicular trafficking via its association with the CART complex. The CART complex is necessary for efficient transferrin receptor recycling but not for EGFR degradation. It is required in a complex with RAB11A and RAB11FIP2 for the transport of NPC1L1 to the plasma membrane. Together with RAB11A participates in CFTR trafficking to the plasma membrane and TF (transferrin) recycling in non-polarized cells. Together with RAB11A and RAB8A participates in epithelial cell polarization. MYO5B as used herein encompasses MYO5B from eukaryotes, preferably mammals, more preferably from humans. A preferred MYO5B is shown in the nucleotide sequence of SEQ ID NO: 11 or the amino acid sequence of SEQ ID NO: 12. Also encompassed by said MYO5B is a RNA transcript that has 50%, 60%, 70%, 80%, 90% or 95% or more identity over its entire nucleotide sequence with SEQ ID NO: 11. Also encompassed by said MYO5B is an expression product of an RNA transcript that has 50%, 60%, 70%, 80%, 90% or 95% or more identity over its entire amino acid sequence with in SEQ ID NO: 12. The percentage of sequence identity can, for example, be determined as described above.

RAB8A, also known as Mel Transforming Oncogene, MEL, Ras-Associated Protein RAB8, is a member of the RAS superfamily which are small GTP/GDP-binding proteins with an average size of 200 amino acids. The RAS-related proteins of the RAB/YPT family may play a role in the transport of proteins from the endoplasmic reticulum to the Golgi and the plasma membrane. RAB8A as used herein encompasses RAB8A from eukaryotes, preferably mammals, more preferably from humans. A preferred RAB8A is shown in the nucleotide sequence of SEQ ID NO: 13 or the amino acid sequence of SEQ ID NO: 14. Also encompassed by said RAB8A is a RNA transcript that has 50%, 60%, 70%, 80%, 90% or 95% or more identity over its entire nucleotide sequence with SEQ ID NO: 13. Also encompassed by said RAB8A is an expression product of an RNA transcript that has 50%, 60%, 70%, 80%, 90% or 95% or more identity over its entire amino acid sequence with in SEQ ID NO: 14. The percentage of sequence identity can, for example, be determined as described above.

RAB9A, also known as Ras-Related Protein Rab-9A, belongs to the Rab family of the small GTPase superfamily. RAB9A as used herein encompasses RAB9A from eukaryotes, preferably mammals, more preferably from humans. A preferred RAB9A is shown in the nucleotide sequence of SEQ ID NO: 15 or the amino acid sequence of SEQ ID NO: 16. Also encompassed by said RAB9A is a RNA transcript that has 50%, 60%, 70%, 80%, 90% or 95% or more identity over its entire nucleotide sequence with SEQ ID NO: 15. Also encompassed by said RAB9A is an expression product of an RNA transcript that has 50%, 60%, 70%, 80%, 90% or 95% or more identity over its entire amino acid sequence with in SEQ ID NO: 16. The percentage of sequence identity can, for example, be determined as described above.

RAB10, also known as Ras-related GTP-binding protein, belongs to the Rab family of the small GTPase superfamily. RAB10 as used herein encompasses RAB10 from eukaryotes, preferably mammals, more preferably from humans. A preferred RAB10 is shown in the nucleotide sequence of SEQ ID NO: 17 or the amino acid sequence of SEQ ID NO: 18. Also encompassed by said RAB10 is a RNA transcript that has 50%, 60%, 70%, 80%, 90% or 95% or more identity over its entire nucleotide sequence with SEQ ID NO: 17. Also encompassed by said RAB10 is an expression product of an RNA transcript that has 50%, 60%, 70%, 80%, 90% or 95% or more identity over its entire amino acid sequence with in SEQ ID NO: 18. The percentage of sequence identity can, for example, be determined as described above.

RAB11A, also known as YL8, Ras-related protein Rab-11A, belongs to the Rab family of the small GTPase superfamily. RAB11A as used herein encompasses RAB11A from eukaryotes, preferably mammals, more preferably from humans. A preferred RAB11A is shown in the nucleotide sequence of SEQ ID NO: 19 or the amino acid sequence of SEQ ID NO: 20. Also encompassed by said RAB11A is a RNA transcript that has 50%, 60%, 70%, 80%, 90% or 95% or more identity over its entire nucleotide sequence with SEQ ID NO: 19. Also encompassed by said RAB11A is an expression product of an RNA transcript that has 50%, 60%, 70%, 80%, 90% or 95% or more identity over its entire amino acid sequence with in SEQ ID NO: 20. The percentage of sequence identity can, for example, be determined as described above.

RAB25, also known as Ras-related protein Rab-25, CATX8 or RAB11C, is a member of the RAS superfamily of small GTPases and may be involved in membrane trafficking and cell survival. It may be a tumor suppressor and an oncogene, depending on the context. RAB25 as used herein encompasses RAB25 from eukaryotes, preferably mammals, more preferably from humans. A preferred RAB25 is shown in the nucleotide sequence of SEQ ID NO: 21 or the amino acid sequence of SEQ ID NO: 22. Also encompassed by said RAB25 is a RNA transcript that has 50%, 60%, 70%, 80%, 90% or 95% or more identity over its entire nucleotide sequence with SEQ ID NO: 21. Also encompassed by said RAB25 is an expression product of an RNA transcript that has 50%, 60%, 70%, 80%, 90% or 95% or more identity over its entire amino acid sequence with in SEQ ID NO: 22. The percentage of sequence identity can, for example, be determined as described above.

CDC42, also known as Cell division cycle 42, G25K GTP-binding protein or TKS, is a small GTPase of the Rho-subfamily, which regulates signaling pathways that control diverse cellular functions including cell morphology, migration, endocytosis and cell cycle progression. This protein could regulate actin polymerization through its direct binding to Neural Wiskott-Aldrich syndrome protein (N-WASP), which subsequently activates Arp2/3 complex. CDC42 as used herein encompasses CDC42 from eukaryotes, preferably mammals, more preferably from humans. A preferred CDC42 is shown in the nucleotide sequence of SEQ ID NO: 23 or the amino acid sequence of SEQ ID NO: 24. Also encompassed by said CDC42 is a RNA transcript that has 50%, 60%, 70%, 80%, 90% or 95% or more identity over its entire nucleotide sequence with SEQ ID NO: 23. Also encompassed by said CDC42 is an expression product of an RNA transcript that has 50%, 60%, 70%, 80%, 90% or 95% or more identity over its entire amino acid sequence with in SEQ ID NO: 24. The percentage of sequence identity can, for example, be determined as described above.

RAC1, also known as Ras-Related C3 Botulinum Toxin Substrate 1, Cell migration-inducing protein 5, P21-Rac1, TC25 or MIG5, is a GTPase which belongs to the RAS superfamily of small GTP-binding proteins. Members of this superfamily appear to regulate a diverse array of cellular events, including the control of cell growth, cytoskeletal reorganization, and the activation of protein kinases. RAC1 as used herein encompasses RAC1 from eukaryotes, preferably mammals, more preferably from humans. A preferred RAC1 is shown in the nucleotide sequence of SEQ ID NO:

25 or the amino acid sequence of SEQ ID NO: 26. Also encompassed by said RAC1 is a RNA transcript that has 50%, 60%, 70%, 80%, 90% or 95% or more identity over its entire nucleotide sequence with SEQ ID NO: 25. Also encompassed by said RAC1 is an expression product of an RNA transcript that has 50%, 60%, 70%, 80%, 90% or 95% or more identity over its entire amino acid sequence with in SEQ ID NO: 26. The percentage of sequence identity can, for example, be determined as described above.

RhoA, also known as Ras Homolog Family Member A, Aplysia Ras-related homolog 12 (ARHA) or RHO12, is a member of the Rho family of small GTPases. Among its related pathways are Bisphosphonate Pathway, Pharmacodynamics and Development VEGF signaling via VEGFR2—generic cascades. GO annotations related to this gene include GTP binding and myosin binding. RhoA as used herein encompasses RhoA from eukaryotes, preferably mammals, more preferably from humans. A preferred RhoA is shown in the nucleotide sequence of SEQ ID NO: 27 or the amino acid sequence of SEQ ID NO: 28. Also encompassed by said RhoA is a RNA transcript that has 50%, 60%, 70%, 80%, 90% or 95% or more identity over its entire nucleotide sequence with SEQ ID NO: 27. Also encompassed by said RhoA is an expression product of an RNA transcript that has 50%, 60%, 70%, 80%, 90% or 95% or more identity over its entire amino acid sequence with in SEQ ID NO: 28. The percentage of sequence identity can, for example, be determined as described above.

Preferably, the clinical outcome is recurrence-free interval (RFI), overall survival (OS), disease-free survival (DFS), distant recurrence-free interval (DRFI), likelihood of occurrence of recrudescence, metastasis development or disease progression.

The term "positive clinical outcome" means an improvement in any measure of patient status, including those measures ordinarily used in the art, such as an increase in the duration of Recurrence-Free interval (RFI), an increase in the time of Overall Survival (OS), an increase in the time of Disease-Free Survival (DFS), an increase in the duration of Distant Recurrence-Free Interval (DRFI), and the like. An increase in the likelihood of positive clinical outcome corresponds to a decrease in the likelihood of occurrence of recrudescence, metastasis development or disease progression.

The term "long-term" survival is used herein to refer to survival for at least 3 years, more preferably for at least 5 years. The term "Recurrence-Free Interval (RFI)" is used herein to refer to time in years to first cancer recurrence censoring for second primary cancer as a first event or death without evidence of recurrence. The term "Overall Survival (OS)" is used herein to refer to time in years from surgery to death from any cause. The term "Disease-Free Survival (DFS)" is used herein to refer to time in years to cancer recurrence or death from any cause. The term "Distant Recurrence-Free Interval (DRFI)" is used herein to refer to the time (in years) from surgery to the first anatomically distant cancer recurrence.

The term "likelihood" when used in the context of outcome or predisposition describes the probability of a certain outcome, no matter if positive or negative, or predisposition. Likelihood does not necessarily have to be 100% accurate. This is so because—self-explanatory as it is—the methods of the invention cannot provide a 100% safe prediction whether or not a patient may have a positive or negative outcome or if a patient has or has not a predisposition to develop colorectal cancer, skin cancer, head and neck cancer or lung cancer, since, apart from the expression of the biomarkers, individual factors such as age, body weight, general health, sex, diet, lifestyle, drug interaction and the like may have an influence on the outcome or predisposition. However, if a subject diagnosed with colorectal cancer, skin cancer, head and neck cancer or lung cancer shows a decreased expression of the biomarkers of the invention, the likelihood or probability that the subject has a negative outcome or a predisposition is more than 50%. Preferably, the likelihood or probability is more than 60%, 70%, 80% or 90%, more preferably more than 95%. Obviously, the terms "increased likelihood of a positive outcome" and "decreased likelihood of a negative outcome" have the same meaning. This also applies to "increased likelihood of a negative outcome" and "decreased outcome of a positive outcome". If a subject shows a decreased expression of the biomarkers of the invention, the likelihood or probability that the patient has a predisposition for colorectal cancer, skin cancer, head and neck cancer or lung cancer is more than 50%. Preferably, the likelihood or probability is more than 60%, 70%, 80% or 90%, more preferably more than 95%.

It is also preferred that the clinical outcome is benefit of the subject from therapy. The therapy may be chemotherapy, adjuvant chemotherapy, radiation therapy, targeted therapy or immunotherapy.

Chemotherapy is a category of cancer treatment that uses one or more anti-cancer drugs (chemotherapeutic agents) as part of a standardized chemotherapy regimen. Chemotherapy may be given with a curative intent (which almost always involves combinations of drugs), or it may aim to prolong life or to reduce symptoms (palliative chemotherapy).

Adjuvant therapy, also known as adjunct therapy, add-on therapy, and adjuvant care, is therapy that is given in addition to the primary or initial therapy to maximize its effectiveness. The surgeries and complex treatment regimens used in cancer therapy have led the term to be used mainly to describe adjuvant cancer treatments. An example of such adjuvant therapy is the additional treatment usually given after surgery where all detectable disease has been removed, but where there remains a statistical risk of relapse due to the presence of undetected disease. If known disease is left behind following surgery, then further treatment is not technically adjuvant. Radiation therapy or radiotherapy, often abbreviated RT, RTx, or XRT, is therapy using ionizing radiation, generally as part of cancer treatment to control or kill malignant cells and normally delivered by a linear accelerator. An adjuvant agent modifies the effect of another agent, so adjuvant therapy modifies other therapy.

Radiation therapy may be curative in a number of types of cancer if they are localized to one area of the body. It may also be used as part of adjuvant therapy, to prevent tumor recurrence after surgery to remove a primary malignant tumor. Radiation therapy is synergistic with chemotherapy, and has been used before, during, and after chemotherapy in susceptible cancers.

Targeted therapy or molecularly targeted therapy is one of the major modalities of medical treatment (pharmacotherapy) for cancer. As a form of molecular medicine, targeted therapy blocks the growth of cancer cells by interfering with specific targeted molecules needed for carcinogenesis and tumor growth, rather than by simply interfering with all rapidly dividing cells with traditional chemotherapy. Because most agents for targeted therapy are biopharmaceuticals, the term biologic therapy may be sometimes synonymous with targeted therapy when used in the context of cancer therapy and thus distinguished from chemotherapy, that is, cytotoxic therapy. However, the modalities may be combined; antibody-drug conjugates combine biologic and cytotoxic mechanisms into one targeted therapy. Another form of targeted therapy may involve the use of nanoengineered enzymes to bind to a tumor cell such that the body's natural cell degradation process can digest the cell, effectively eliminating it from the body.

Immunotherapy or cancer immunotherapy is the use of the immune system to treat cancer. Immunotherapies can be categorized as active, passive or hybrid (active and passive). These approaches exploit the fact that cancer cells often have molecules on their surface that can be detected by the immune system, known as tumor-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses and include the use of monoclonal antibodies, lymphocytes and cytokines. Among these, multiple antibody therapies are approved in various jurisdictions to treat a wide range of cancers. Cell surface receptors are common targets for antibody therapies and include CD20, CD274 and CD279. Once bound to a cancer antigen, antibodies can induce antibody-dependent cell-mediated cytotoxicity, activate the complement system, or prevent a receptor from interacting with its ligand, all of which can lead to cell death. Approved antibodies include alemtuzumab, ipilimumab, nivolumab, ofatumumab and rituximab.

Not all subjects diagnosed with cancer profit from therapy. Cancer therapy is especially useful and effective at early stages of the diseases like stage I or II colorectal cancer, skin cancer, head and neck cancer or lung cancer. Thus, the use of the biomarkers of the present invention may help identifying those subjects, which will profit the most of a therapy. Accordingly, the therapy preferably is for a subject having stage I or II colorectal cancer, skin cancer, head and neck cancer or lung cancer.

The terms "cancer" and "cancerous" refer to or describe the physiological condition in mammals that is typically characterized by unregulated cell growth. Examples of cancer include, but are not limited to, skin cancer, colorectal cancer, head and neck cancer, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid. Preferably, cancer as referred to herein in the methods, uses and kits is colorectal cancer, skin cancer, head and neck cancer or lung cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "colorectal cancer" is used in the broadest sense and refers to (1) all stages and all forms of cancer arising from epithelial cells of the large intestine and/or rectum and/or (2) all stages and all forms of cancer affecting the lining of the large intestine and/or rectum. In the staging systems used for classification of colorectal cancer, the colon and rectum may be treated as one organ.

The term "skin cancer" as used herein relates to cancers that arise from the skin. There are three main types of skin cancers, which are encompassed by said term: basal-cell skin cancer (BCC), squamous-cell skin cancer (SCC) and melanoma. The first two, along with a number of less common skin cancers, are known as nonmelanoma skin cancer (NMSC). Basal-cell cancer grows slowly and can damage the tissue around it but is unlikely to spread to distant areas or result in death. It often appears as a painless raised area of skin that may be shiny with small blood vessel running over it or may present as a raised area with an ulcer. Squamous-cell skin cancer is more likely to spread. It usually presents as a hard lump with a scaly top but may also form an ulcer. Melanomas are the most aggressive. Signs include a mole that has changed in size, shape, color, has irregular edges, has more than one color, is itchy or bleeds.

The term "head and neck cancer" as used herein relates to a group of cancers that starts within the mouth, nose, throat, larynx, sinuses, or salivary glands. Symptoms may include a lump or sore that does not heal, a sore throat that does not go away, trouble swallowing, or a change in the voice. There may also be unusual bleeding, facial swelling, or trouble breathing.

The term "lung cancer" as used herein relates to lung carcinoma, a malignant lung tumor characterized by uncontrolled cell growth in tissues of the lung. This growth can spread beyond the lung by the process of metastasis into nearby tissue or other parts of the body. The two main types are small-cell lung carcinoma (SCLC) and non-small-cell lung carcinoma (NSCLC). The most common symptoms are coughing (including coughing up blood), weight loss, shortness of breath, and chest pains.

Cancers like colorectal cancer, skin cancer, head and neck cancer or lung cancer may be staged by using the TNM system of the American Joint Committee on Cancer. It is based on the characterization of primary tumor (T), on the presence of metastasis in regional, efferent lymph nodes ("N") and on the presence of distant metastases ("M").

In or to allow a reasonable prediction of the clinical outcome of colorectal cancer, skin cancer, head and neck cancer or lung cancer, it is preferred that the normalized expression level has to be compared to gene expression data obtained from corresponding cancer reference samples. Corresponding cancer reference samples are samples that have been obtained from subjects that have a known clinical outcome. Thus, a person skilled in the art compares the normalized expression levels of samples with reference samples and can decide on the relative difference on the clinical outcome.

The normalized expression level of an RNA transcript or and expression product thereof may be determined by various methods. RNA transcripts may be determined using a nucleic acid amplification-based method. Preferably, the nucleic acid amplification-based method is PCR, microarrays or quantitative PCR. Methods for the detection of expression products comprise antibody-based methods, preferably histochemistry, ELISA (enzyme-linked immunosorbent assay) or Western Blot, or mass spectrometry. The application of these methods is known to a person skilled in the art.

Accordingly, it is preferred that the normalized expression level of an RNA transcript of MYO5B and/or RAB8A or an expression product thereof, is determined using a nucleic acid amplification-based method, such as PCR, or a method for quantifying expression products, such as antibody-based methods, e.g. histochemistry, ELISA or mass spectrometry.

In addition to the normalized expression levels of MYO5B and/or RAB8A, the additional biomarkers RAB9A, RAB10, RAB11A, RAB25, CDC42, RAC and/or RhoA have to be analyzed as well. Accordingly, it is preferred that the normalized expression level of an RNA transcript of RAB9A, RAB10, RAB11A, RAB25, CDC42, RAC and/or RhoA or an expression product thereof is determined using a nucleic acid amplification-based method, such as PCR, or a method for quantifying expression products, such as antibody-based methods, e.g. histochemistry, ELISA or mass spectrometry.

The expression level of RNA transcripts have to be normalized to enable comparison to other samples or control samples. In order to achieve this, the expression levels of RNA transcripts are normalized relative to the expression level of an RNA transcript of at least one reference gene. Reference genes are e.g. actin, 18S or GAPDH (Glyceraldehyde 3-phosphate dehydrogenase), HPRT (Hypoxanthine-guanine phosphoribosyltransferase).

It is preferred that the normalized expression level of an RNA transcript of MYO5B and/or RAB8A is normalized relative to the expression level of an RNA transcript of at least one reference gene. Similarly it is preferred that the normalization of the levels of RNA transcripts of the additional biomarkers RAB9A, RAB10, RAB11A, RAB25, CDC42, RAC and/or RhoA, one may also use expression levels of an RNA transcript of reference genes. Accordingly, the normalized expression level of an RNA transcript of RAB9A, RAB10, RAB11A, RAB25, CDC42, RAC and/or RhoA may be normalized relative to the expression level of an RNA transcript of at least one reference gene.

The normalized expression levels of expression products of RNA transcripts have to be normalized as well in order to enable the comparison to other samples or control samples. In order to achieve this, the expression level of an expression product of a RNA transcript is preferably normalized relative to the expression level of an expression product of an RNA transcript of at least one reference gene. Reference genes are e.g. actin, 18S, GAPDH (Glyceraldehyde 3-phosphate dehydrogenase), nucleolin.

In a preferred embodiment of the invention, the normalized expression level of an expression product of an RNA transcript of MYO5B and/or RAB8A is normalized relative to the expression level of an expression product of an RNA transcript of at least one reference gene.

For the normalization of the levels of an expression product of an RNA transcript of the additional biomarkers RAB9A, RAB10, RAB11A, RAB25, CDC42, RAC and/or RhoA, one may also use expression levels of an expression product of an RNA transcript of reference genes. Accordingly, it is preferred that the normalized expression level of an expression product of an RNA transcript of RAB9A, RAB10, RAB11A, RAB25, CDC42, RAC and/or RhoA is normalized relative to the expression level of an expression product of an RNA transcript of at least one reference gene.

The term "subject" as used herein includes any mammal. Preferably, the subject is human patient. This patient preferably suffers from or is at risk of colorectal cancer, skin cancer, head and neck cancer or lung cancer.

The term "biological sample" as used herein relates to a fresh or frozen tissue sample, blood sample, laser-microdissected sample, paraffin-embedded and fixed sample. The biological sample preferably comprises cells. More preferably, the cells are cancer cells.

The invention further relates to a method for predicting clinical outcome for a subject diagnosed with colorectal cancer, skin cancer, head and neck cancer or lung cancer, comprising: (a) determining a normalized expression level of an RNA transcript of MYO5B and RAB8A, or an expression product thereof, in a biological sample comprising colorectal, skin, head and neck or lung cancer cells obtained from said subject; and (b) predicting the likelihood of a positive clinical outcome for said subject based on said normalized expression level, wherein an increased normalized expression of an RNA transcript of MYO5B and RAB8A, or an expression product thereof, is positively correlated with an increased likelihood of a positive outcome.

The invention further relates to a method for predicting clinical outcome for a subject diagnosed with colorectal cancer, skin cancer, head and neck cancer or lung cancer, comprising: (a) determining a normalized expression level of an RNA transcript of only MYO5B and RAB8A, or an expression product thereof, in a biological sample comprising colorectal, skin, head and neck or lung cancer cells obtained from said subject; and (b) predicting the likelihood of a positive clinical outcome for said subject based on said normalized expression level, wherein an increased normalized expression of an RNA transcript of MYO5B and RAB8A, or an expression product thereof, is positively correlated with an increased likelihood of a positive outcome.

The invention further relates to a method for predicting clinical outcome for a subject diagnosed with colorectal cancer, skin cancer, head and neck cancer or lung cancer, comprising: (a) determining a normalized expression level of an RNA transcript of MYO5B and RAB9A, MYO5B and RAB10, MYO5B and RAB11A, MYO5B and RAB25, MYO5B and CDC42, MYO5B and RAC, or MYO5B and RhoA, or an expression product thereof, in a biological sample comprising colorectal, skin, head and neck or lung cancer cells obtained from said subject; and (b) predicting the likelihood of a positive clinical outcome for said subject based on said normalized expression level, wherein an increased normalized expression of an RNA transcript of MYO5B and RAB9A, MYO5B and RAB10, MYO5B and RAB11A, MYO5B and RAB25, MYO5B and CDC42, MYO5B and RAC, or MYO5B and RhoA, or an expression product thereof, is positively correlated with an increased likelihood of a positive outcome.

The invention further relates to a method for predicting clinical outcome for a subject diagnosed with colorectal cancer, skin cancer, head and neck cancer or lung cancer, comprising: (a) determining a normalized expression level of an RNA transcript of RAB8A and RAB9A, RAB8A and RAB10, RAB8A and RAB11A, RAB8A and RAB25, RAB8A and CDC42, RAB8A and RAC, or RAB8A and RhoA, or an expression product thereof, in a biological sample comprising colorectal, skin, head and neck or lung cancer cells obtained from said subject; and (b) predicting the likelihood of a positive clinical outcome for said subject based on said normalized expression level, wherein an increased normalized expression of an RNA transcript of RAB8A and RAB9A, RAB8A and RAB10, RAB8A and RAB11A, RAB8A and RAB25, RAB8A and CDC42, RAB8A and RAC, or RAB8A and RhoA, or an expression product thereof, is positively correlated with an increased likelihood of a positive outcome.

The inventors surprisingly found that there is an inverse correlation between the expression of MYO5B and/or RAB8A and the progression of cancer. This finding is also useful in the analysis whether a subject has a predisposition to develop colorectal cancer, skin cancer, head and neck cancer or lung cancer. Accordingly, the present invention also relates in a further aspect to a method for predicting whether a subject has a predisposition to develop colorectal cancer, skin cancer, head and neck cancer or lung cancer, comprising: (a) determining a normalized expression level of an RNA transcript of MYO5B and/or RAB8A, or an expression product thereof, in a biological sample comprising colorectal, skin, head and neck or lung cells obtained from said subject; and (b) predicting the likelihood of a predisposition for said subject based on said normalized expression level, wherein an increased normalized expression of an RNA transcript of MYO5B and/or RAB8A, or an expression product thereof, is positively correlated with a decreased likelihood of a predisposition to develop colorectal, skin, head and neck or lung cancer.

The invention further relates to a method for predicting whether a subject has a predisposition to develop colorectal cancer, skin cancer, head and neck cancer or lung cancer, comprising: (a) determining a normalized expression level of an RNA transcript of only MYO5B and/or RAB8A, or an expression product thereof, in a biological sample comprising colorectal, skin, head and neck or lung cells obtained from said subject; and (b) predicting the likelihood of a predisposition for said subject based on said normalized expression level, wherein an increased normalized expression of an RNA transcript of MYO5B and/or RAB8A, or an expression product thereof, is positively correlated with a decreased likelihood of a predisposition to develop colorectal, skin, head and neck or lung cancer.

Alternatively, the invention relates to a method for predicting whether a subject has a predisposition to develop colorectal cancer, skin cancer, head and neck cancer or lung cancer, comprising: (a) determining a normalized expression level of an RNA transcript of MYO5B and/or RAB8A, or an expression product thereof, in a biological sample comprising colorectal, skin, head and neck or lung cells obtained from said subject; and (b) predicting the likelihood of a predisposition for said subject based on said normalized expression level, wherein a decreased normalized expression of an RNA transcript of MYO5B and/or RAB8A, or an expression product thereof, is positively correlated with an increased likelihood of a predisposition to develop colorectal, skin, head and neck or lung cancer.

The method predicting whether a subject has a predisposition to develop colorectal cancer, skin cancer, head and neck cancer or lung cancer may also additionally comprise the analysis of additional biomarkers. Accordingly, it is preferred that the method predicting whether a subject has a predisposition to develop colorectal cancer, skin cancer, head and neck cancer or lung cancer may further comprise (c) determining a normalized expression level of an RNA transcript of RAB9A, RAB10, RAB11A, RAB25, CDC42, RAC and/or RhoA, or an expression product thereof, in a biological sample comprising colorectal, skin, head and neck or lung cells obtained from said subject; and (d) predicting the likelihood of a predisposition for said subject based on said normalized expression level, wherein an increased normalized expression of an RNA transcript of RAB9A, RAB10, RAB11A, RAB25, CDC42, RAC and/or RhoA, or an expression product thereof, is positively correlated with a decreased likelihood of a predisposition to develop colorectal, skin, head and neck or lung cancer.

Alternatively, the method for predicting whether a subject has a predisposition to develop colorectal cancer, skin cancer, head and neck cancer or lung cancer may further comprise (c) determining a normalized expression level of an RNA transcript of RAB9A, RAB10, RAB11A, RAB25, CDC42, RAC and/or RhoA, or an expression product thereof, in a biological sample comprising colorectal, skin, head and neck or lung cells obtained from said subject; and (d) for said subject based on said normalized expression level, wherein a decreased normalized expression of an RNA transcript of RAB9A, RAB10, RAB11A, RAB25, CDC42, RAC and/or RhoA, or an expression product thereof, is positively correlated with an increased likelihood of a predisposition to develop colorectal, skin, head and neck or lung cancer.

The embodiments described in the method for predicting clinical outcome for a subject diagnosed with colorectal cancer, skin cancer, head and neck cancer or lung cancer as described herein also apply mutatis mutandis to the method for predicting whether a subject has a predisposition to develop colorectal cancer, skin cancer, head and neck cancer or lung cancer with one exception concerning the reference sample described in the next paragraph.

In order to allow a reasonable prediction of the predisposition to develop colorectal cancer, skin cancer, head and neck cancer or lung cancer, the normalized expression level has to be compared to gene expression data obtained from healthy reference samples in the method for predicting whether a subject has a predisposition to develop colorectal cancer, skin cancer, head and neck cancer or lung cancer. Healthy reference samples have been obtained from subjects that do not have a predisposition to colorectal cancer, skin cancer, head and neck cancer or lung cancer. Thus, a person skilled in the art compares the normalized expression levels of samples with healthy reference samples and can decide based on the relative difference on the predisposition.

In a still further aspect of the invention, the expression levels of the biomarkers of the invention may also be useful in the staging of the colorectal cancer, skin cancer, head and neck cancer or lung cancer. The staging of cancers is a useful tool to adapt a treatment plan or regimen to the actual need of a subject. The biomarkers of the invention are useful new tools to quickly and reliably categorize subjects into the different stages. Accordingly, the present invention relates to a method for aiding in the staging of colorectal cancer, skin cancer, head and neck cancer or lung cancer of a subject, comprising (a) determining a normalized expression level of an RNA transcript of MYO5B and/or RAB8A, or an expression product thereof, in a biological sample comprising colorectal, skin, head and neck or lung cancer cells obtained from said subject; and (b) predicting the cancer stage for said subject based on said normalized expression level, wherein a decreased normalized expression of an RNA transcript of MYO5B and/or RAB8A, or an expression product thereof, is positively correlated with a more advanced colorectal, skin, head and neck or lung cancer stage.

In another embodiment, the present invention relates to a method for aiding in the staging of colorectal cancer, skin cancer, head and neck cancer or lung cancer of a subject, comprising (a) determining a normalized expression level of an RNA transcript of only MYO5B and/or RAB8A, or an expression product thereof, in a biological sample comprising colorectal, skin, head and neck or lung cancer cells obtained from said subject; and (b) predicting the cancer stage for said subject based on said normalized expression level, wherein a decreased normalized expression of an RNA transcript of MYO5B and/or RAB8A, or an expression product thereof, is positively correlated with a more advanced colorectal, skin, head and neck or lung cancer stage.

Alternatively, the method for aiding in the staging of colorectal cancer, skin cancer, head and neck cancer or lung cancer of a subject, comprising (a) determining a normalized expression level of an RNA transcript of MYO5B and/or RAB8A, or an expression product thereof, in a biological sample comprising colorectal, skin, head and neck or lung cancer cells obtained from said subject; and (b) predicting the cancer stage for said subject based on said normalized expression level, wherein an increased normalized expression of an RNA transcript of MYO5B and/or RAB8A, or an expression product thereof, is positively correlated with a less advanced colorectal, skin, head and neck or lung cancer stage.

The staging may be further supported by the analysis of additional biomarkers. Accordingly, the method for aiding in the staging of colorectal cancer, skin cancer, head and neck cancer or lung cancer of a subject may further comprise (c) determining a normalized expression level of an RNA transcript of RAB9A, RAB10, RAB11A, RAB25, CDC42, RAC and/or RhoA, or an expression product thereof, in a biological sample comprising colorectal cancer cells obtained from said subject; and (d) predicting the cancer stage for said subject based on said normalized expression level, wherein a decreased normalized expression of an RNA transcript of RAB9A, RAB10, RAB11A, RAB25, CDC42, RAC and/or RhoA, or an expression product thereof, is positively correlated with a more advanced colorectal, skin, head and neck or lung cancer stage.

Alternatively, the method for aiding in the staging of colorectal cancer, skin cancer, head and neck cancer or lung cancer of a subject may further comprise (c) determining a normalized expression level of an RNA transcript of RAB9A, RAB10, RAB11A, RAB25, CDC42, RAC and/or RhoA, or an expression product thereof, in a biological sample comprising colorectal cancer cells obtained from said subject; and (d) predicting the cancer stage for said subject based on said normalized expression level, wherein an increased normalized expression of an RNA transcript of RAB9A, RAB10, RAB11A, RAB25, CDC42, RAC and/or RhoA, or an expression product thereof, is positively correlated with a less advanced colorectal, skin, head and neck or lung cancer stage.

The embodiments described in the method for predicting clinical outcome for a subject diagnosed with colorectal cancer, skin cancer, head and neck cancer or lung cancer as described herein also apply mutatis mutandis to the method for aiding in the staging of colorectal cancer, skin cancer, head and neck cancer or lung cancer of a subject.

In another aspect, the biomarkers disclosed in this invention may also be used to determine whether a subject diagnosed with colorectal cancer, skin cancer, head and neck cancer or lung cancer should be subjected to a further therapy following a surgical resection of the cancer. By applying such a method, unnecessary treatments with probable severe side effects could be avoided. Accordingly, the present invention also relates to a method of determining whether a subject diagnosed with colorectal cancer, skin cancer, head and neck cancer or lung cancer should be subjected to further therapy following surgical resection of the cancer, comprising carrying out the method for predicting clinical outcome for a subject diagnosed with colorectal cancer, skin cancer, head and neck cancer or lung cancer and the method for aiding in the staging of colorectal cancer, skin cancer, head and neck cancer or lung cancer, wherein if the likelihood of positive clinical outcome of cancer is decreased, the patient is recommended further therapy following surgical resection.

Alternatively, the present invention relates to method of determining whether a subject diagnosed with colorectal cancer, skin cancer, head and neck cancer or lung cancer should be subjected to further therapy following surgical resection of the cancer, comprising carrying out the method for predicting clinical outcome for a subject diagnosed with colorectal cancer, skin cancer, head and neck cancer or lung cancer or the method for aiding in the staging of colorectal cancer, skin cancer, head and neck cancer or lung cancer, wherein if the likelihood of positive clinical outcome of cancer is increased, the patient is not recommended further therapy following surgical resection.

The therapy following surgical resection preferably is chemotherapy, adjuvant chemotherapy, radiation therapy, targeted therapy or immunotherapy.

The invention further relates to a kit for carrying out the methods of the invention comprising means for determining a normalized expression level of a RNA transcript or an expression product thereof of MYO5B and, optionally at least one of RAB8A, RAB9A, RAB10, RAB11A, RAB25, CDC42, RAC or RhoA. Means for determining a normalized expression level of a RNA transcript comprise primer enabling the amplification of RNA transcripts of the biomarker and optionally one or more reference genes, and optionally at least one of means for RNA extraction, for transcription of RNA to DNA and/or performing a PCR or qPCR reaction. Means for determining a normalized expression level of an expression product of a RNA transcript comprise antibodies or fragments thereof targeting at one or more biomarkers of the invention and optionally one or more of means of extraction of expression products and means for detection of expression products.

The invention further relates to the use of a MYO5B, RAB8A, RAB9A, RAB10, RAB11A, RAB25, CDC42, RAC and/or RhoA nucleic acid for predicting clinical outcome for a subject diagnosed with colorectal cancer, skin cancer, head and neck cancer or lung cancer using the methods described herein.

The invention further relates to the use of an antibody directed against MYO5B, RAB8A, RAB9A, RAB10, RAB11A, RAB25, CDC42, RAC and/or RhoA for predicting clinical outcome for a subject diagnosed with colorectal cancer, skin cancer, head and neck cancer or lung cancer using the methods described herein.

The invention further relates to the use of a MYO5B, RAB8A, RAB9A, RAB10, RAB11A, RAB25, CDC42, RAC and/or RhoA nucleic acid for aiding in the staging of colorectal cancer, skin cancer, head and neck cancer or lung cancer of a subject using the methods described herein.

The invention further relates to the use of an antibody directed against MYO5B, RAB8A, RAB9A, RAB10, RAB11A, RAB25, CDC42, RAC and/or RhoA for aiding in the staging of colorectal cancer, skin cancer, head and neck cancer or lung cancer of a subject using the methods described herein.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "more than" does not include the concrete number.

For example, less than 20 means less than the number indicated. Similarly, more than or greater than means more than or greater than the indicated number, e.g. more than 80% means more than or greater than the indicated number of 80%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

A better understanding of the present invention and of its advantages will be had from the following examples, offered for illustrative purposes only. The examples are not intended to limit the scope of the present invention in any way.

EXAMPLES OF THE INVENTION

The following examples illustrate the invention. These examples should not be construed as to limit the scope of the invention. The examples are included for purposes of illustration and the present invention is limited only by the claims.

Example 1: Material and Methods

Patients and Samples

All human tissue samples used in this study were donated freely and written informed consent as well as ethical approval from the Comité National d'Ethique de Recherche du Luxembourg (Reference 201009/09) and from the institutional Ethics Review Panel (ERP-16-032) were obtained. Primary colon cancer samples and matched distant non-neoplastic colon tissue (at the furthest longitudinal surgical margin) from 61 CRC patients were collected by the Integrated Biobank of Luxembourg (IBBL) following the standard preanalytical protocol for biospecimens (Betsou et al, 2010). Samples were immediately stored in liquid nitrogen after surgical excision.

The CRC cohort was composed of 61 CRC patients including 41 male and 20 female patients with a median age of 68 years (68±11, range 53-88). The histopathological data was provided by a pathologist. The cohort includes stage I (n=8), II (n=29), III (n=19), and IV (n=3) tumor samples, classified according to the TNM Classification of Malignant Tumors (TNM system, American Joint Committee on Cancer) (Hari et al, 2013) staging system, as well as 61 normal tissue samples matching the corresponding tumor. The CRC collection has been complemented with 46 tumor specimens from the Ontario Tumor Bank (Ontario Institute for Cancer Research).

Materials

All CRC cell lines were obtained from the American Type Culture Collection (ATCC, Rockville, USA) and maintained in recommended culture conditions. For methylation analysis, cells were treated with 5 µM 5-Aza-2'-Deoxycytidine (5-aza-dC/DAC, Sigma) or vehicle (DMSO) for four days followed by RNA extraction.

Tissue Preparation, RNA/DNA Extraction and RT-qPCR

Tissue processing and laser-microdissection (LMD) were performed as previously described (Letellier et al, 2014). AllPrep extraction kits (Qiagen) was used to extract RNA and DNA from microdissected samples. cDNA was obtained via reverse transcription by using a high capacity cDNA reverse transcription kit (Applied Biosystems). The Experion™ automated electrophoresis system (Bio-Rad Laboratories, Inc.) was used to check for RNA quality, which was of acceptable quality for all primary samples. The expression of MYO5B was investigated using TaqMan chemistry-based primer/probe sets that are recommended for the use of RNA from microdissected samples (Erickson et al, 2009) (Table 1 for reference numbers).

PCR conditions were used as previously described (Letellier et al, 2014) and the expression levels of the gene of interest were normalized against the housekeeping gene HPRT (Erickson et al, 2009). For bulk tissue and CRC cell lines, the RNA was extracted with the Mirneasy kit from Qiagen and the cDNA was obtained with the mirscript II (Qiagen). PCR cycling conditions as well as quality control and normalization steps were done in qBase+ (Biogazelle), using 2 reference genes as previously described (Qureshi-Baig et al, 2016; Ullmann et a, 2016). Primer sequences are listed in Table 1.

TABLE 1

Primer sequences

| Primer | Sequences | |
|---|---|---|
| MYO5B-F | 5'-AACGTGGGCATGGAGAACAAGG-3' | (SEQ ID NO: 1) |
| MYO5B-R | 5'-TTCTTCAGCCGCTCTACCTCCA-3' | (SEQ ID NO: 2) |
| RAB8A-F | 5'-TCAGGAACGGITTCGGACGATC-3' | (SEQ ID NO: 3) |
| RAB8A-R | 5'-GCTCCTCAATGTTGCGAATCCAG-3' | (SEQ ID NO: 4) |

TABLE 1-continued

Primer sequences

| Primer | Sequences |
|---|---|
| RAB25-F | 5'-ACTGCTCTTCCTGGAGACCTCA-3' (SEQ ID NO: 5) |
| RAB25-R | 5'-GCTGTTCTGTCTCTGCTTGGAC-3 (SEQ ID NO: 6) |
| House-keeping genes: | |
| HPRT-F | 5'-TGGACAGGACTGAACGTCTT-3 (SEQ ID NO: 7) |
| HPRT-R | 5'-GAGCACACAGAGGGCTACAA-3' (SEQ ID NO: 8) |
| CycloA F | 5'-CAGACAAGGTCCCAAAGACA-3' (SEQ ID NO: 9) |
| CycloA R | R-5'-CCATTATGGCGTGTGAAGTC-3' (SEQ ID NO: 10) |
| MYO5B | Taqman assays-Hs00393037_m1 |
| HPRT1 | Taqman assay HPRT1-Hs02800695_m1 (Applied Biosystems, Thermo Fisher Scientific) |

Methylation Analysis

For monitoring of the methylation pattern of the entire MYO5B promoter, MassARRAY technology by Sequenom was performed at Varionostics GmbH, Ulm, Germany.

Tissue Microarrays and Immunohistochemical Analysis

Tissue microarray (TMA) blocks were prepared using primary CRC formalin-fixed paraffin-embedded tumor samples as well as their paired normal colon counterparts. Two punches, one millimeter in diameter, were taken from each donor block providing two spots of both tumor and normal control tissue. The punching of tissue cores and their transfer to the receiver block were done using a 3D Histech® TMA arrayer. Immunohistochemical staining was done on an automated Benchmark XT device (Ventana) using the CC1M antigen retrieval protocol (Cell Conditioning 1 buffer, basic pH and M=30 minutes). Primary antibody against MYO5B (HPA040902, Sigma-Aldrich) was used at a 1:50 dilution, with an incubation time of 32 min. The secondary antibody (dilution) was retrieved from an Ultra-View DAB detection kit (Ventana). Tissue sections were analyzed and a pathologist blindly scored MYO5B staining as follows: 0 (no signal), 1 (low signal), 2 (moderate signal), or 3 (strong signal).

Bioinformatical Meta-Analysis

The setup a meta-analysis has previously been described and used (Letellier et al, 2014). Briefly, all the individual CEL files have been integrated from selected datasets profiled on HG-U133 plus 2.0 (Affymetrix, Santa Clara, CA, USA) retrieved from GEO (GSE14333; GSE17538; GSE21510; GSE8671; GSE9254; GSE20916; GSE10714; GSE15960; GSE4183; GSE10961) and corresponding to different studies (Sabates-Bellver et al, 2007; Galamb et al, 2008, 2010; LaPointe et al, 2008; Jorissen et al, 2009; Skrzypczak et al, 2010; Smith et al, 2010; Tsukamoto et al, 2011) into one single global analysis covering expression data on 829 patients. The suitability of potential biomarkers to discriminate between CRC and normal colon samples was assessed by ROC curves as previously described in (Letellier et al, 2014).

Survival Analyzes

Normalized gene expression values from three different microarray studies with the accession number GSE39582 (Marisa et al, 2013), GSE24551 (Sveen et al, 2011; Agesen et al, 2012), and GSE2881 (Loboda et al, 2011) and containing clinical data on the survival of CRC patients were retrieved from GEO using the R package GEOquery (v2.40, (Davis & Meltzer, 2007)). For gene symbols with multiple probe set assignments, the probe set with the largest interquartile range per gene has been selected, as suggested in (Shi & He, 2016). The retained probe sets for the genes of interest were as follows: MYO5B, 225299_at; RAB8B, 222846_at; RAB10, 222981_s_at; RAB11A, 234998_at; RAB11B, 34478_at; CDC42, 207827_s_at; RAC1, 1567458_s_at; RHOA, 1555814_a_at RAB25 only had one probe set. Survival curves were generated using the R package survival (v2.41-2, (Therneau 2015)) and plotted with the R package survminer (v0.3.1, (Kassambara and Kosinski 2017)). The continuous log 2 expression was separated into two discrete categories ("high" and "low"), separated according to the median MYO5B expression value. Of note, the median value was assigned to the "high" category for odd-numbered datasets.

Combined Gene Signatures

To combine several genes together, the log 2 expression of the six retained genes (MYO5B, RAB8A, RAB9A, RAB10, RAB11A, RAB25) were mean-centered and scaled using the scale( ) function to make them comparable. Then, for each of the 63 combinations, scaled expressions were combined following the PROGgene procedure (Goswami & Nakshatri, 2013). Briefly, the six scaled values were averaged to obtain only one gene expression signature value for each patient. The gene signatures were divided into "high" and "low" groups using the median as described above. Hazard ratios were computed using the coxph( ) function and ranked by the estimates. Differences between Kaplan-Meier curves were assessed using the surdiff( ) function and p-values are reported on each plot.

Data Analysis

All analyzes and plots were generated using the R environment (v3.3.3), the R package ggplot2 (v2.2.1 (Wickham 2009)) and other packages from the tidyverse idiom (Wickham 2017) as well as GraphPad Prism software, version 5 (GraphPad). The student t-test was used in order to compare expression levels between tumor and normal tissue. Kaplan-Meier plots were analyzed using the Cox proportional hazards model, via the survival R package. Unless otherwise stated, results are shown as mean t SD and p-values<0.05 are considered as statistically significant.

Example 2: A Bioinformatics Study Identifies MYO5B as a Potential Biomarker for CRC The relevance of Myosin V family members as novel CRC biomarkers was assessed. First, a meta-analysis of several human CRC datasets (n=829) was used (Letellier et al, 2014), to examine the gene expression of different members of the Myosin V family in CRC. It was found that, compared to samples obtained from normal colorectal mucosa, MYO5A levels were decreased in adenoma samples but did not vary significantly between cancerous and normal tissue (FIG. 1A). Lan and colleagues have previously reported that MYO5A expression is increased in metastatic CRC tissues (Lan et al, 2010). In that study, the epithelial-mesenchymal transition inducer Snail acted as a transcriptional activator of MYO5A, positively affecting cell migration and, subsequently, metastasis dissemination (Lan et al, 2010). However, using the meta-analysis on 829 patients, a significant alteration in MYO5A expression in metastatic vs. non-metastatic tissues (FIG. 7) were not be able to observed. Interestingly and surprisingly, MYO5B expression was reduced by approximately 45% in tumor tissue compared to normal colorectal mucosa samples (FIG. 1A). MYO5C showed a similar decrease in expression (FIG. 1A). Additionally, a detailed analysis of MYO5B expression during CRC progression suggested that MYO5B is down-regulated in a stage-dependent manner (FIG. 1B).

Next, ROC curves were generated to determine the predictive power of MYO5B normalized expression levels to distinguish cancerous from normal tissue. AUC values of 0.9697 and 0.9284 for MYO5B and MYO5C were observed, respectively (FIG. 1C). In contrast, and in accordance with the expression data in FIG. 1A, the levels of MYO5A did not allow for a clear separation of CRC and normal colorectal mucosa samples (AUC=0.5334, FIG. 1C). The distribution of MYO5B gene expression levels separated into two distinct, almost non-overlapping, peaks, whereas a certain degree of overlap was still observable for the MYO5C peaks (FIG. 1C inset). In conclusion, its high AUC values as well as its well-separated distribution profile thus support the use of MYO5B as a diagnostic biomarker. Therefore it was decided to analyze the clinical relevance of MYO5B down-regulation in CRC.

Example 3: MYO5B is Downregulated on mRNA and Protein Level in Primary Human CRC Samples To validate the findings of the bioinformatical analysis, the normalized expression of MYO5B in snap-frozen human CRC samples from a distinct patient cohort was assessed. First, the gene expression of MYO5B in fifty matching CRC and non-tumor bulk tissue samples was analyzed and found that MYO5B normalized expression was significantly lower in the tumor samples (FIG. 2A). To ensure that the expression of MYO5B was derived from epithelial cells and not from infiltrated immune or residing stromal cells, a highly pure malignant or normal epithelial cell population by laser microdissection has been specifically selected.

In a set of 21 paired samples, which was already analyzed as bulk tissue (FIG. 2A) and which was further complemented by a set of 46 CRC laser-microdissected tumor samples, it was observed that MYO5B expression was again significantly decreased in tumor samples, compared to normal colon tissue (FIG. 2B). While examining the paired samples selected by laser microdissection, a higher expression of MYO5B could be observed in adjacent non-tumor tissue than in the corresponding tumor samples in 20 out of 21 tested patients (FIG. 2C).

Interestingly, laser-microdissected samples allowed for a better separation between CRC and non-tumor samples, suggesting that tumor-microenvironmental-derived cells may prevent from a proper analysis of signals emanating from epithelial cells. To further test the potential applicability of MYO5B as a biomarker, tissue microarrays have been used to determine its expression on the protein level. In normal healthy colon epithelium, MYO5B staining is known to be very strong at the apical brush border of the colonic mucosa (Müller et al, 2008). Likewise, a signal for MYO5B has been observed in normal and tumorigenic epithelial cells that occurred inside the cytoplasm and identified an increasing gradient ranging from the basal pole to the apex (FIG. 2D, left panel). Then the staining intensity of MYO5B has been evaluated in 56 paired CRC and non-tumor samples and it was found that normal counterpart tissue shows a significantly stronger signal when compared to matching tumor samples (FIG. 2D, right panel).

To determine whether MYO5B expression correlates with disease progression, the sample set has been divided into early (I and II) and late (III and IV) stage groups based on their TNM staging. Late-stage samples showed a dramatic loss of MYO5B expression (FIG. 2E, left panel) when compared to both normal epithelial tissue (FIG. 2E, right panel) and to samples from earlier stage tumors (FIG. 2E, right panel), confirming the gradual loss of MYO5B observed in the meta-analysis. As the loss of MYO5B is known to contribute to the disruption of cell polarity (Müller et al, 2008), its expression was further investigated in tumors with varying differentiation grades, i.e. ranging from well- to low-differentiated tumors. Interestingly, a stepwise reduction in signal intensity has been observed from well (histological grade 1) to moderately (histological grade 2) and poorly (histological grade 3) differentiated adenocarcinomas (FIG. 2F). Overall, the results show that MYO5B is stage-dependently downregulated and suggest that it might play a role in CRC progression.

Example 4: Loss of MYO5B Expression in CRC is not Due to Promoter Hypermethylation Over the last years, hypermethylation of tumor suppressor genes has been reported in different cancer types (Biswas & Rao, 2017). In a similar manner, MYO5B is methylated in both gastric tumors (Dong et al, 2013) and leukemias (Kuang et al, 2008). Thus, it was analyzed whether promoter methylation could explain the observed down-regulation of MYO5B in CRC. To this end, the expression of MYO5B in CRC cell lines was investigated first after treatment with 5-Aza-2'-Deoxycytidine (5-aza-dC/DAC), a known demethylating agent.

However, DAC treatment only resulted in minor changes compared to MYO5B basal expression levels (FIG. 3A), suggesting that methylation of its promoter may not be responsible for the observed reduction in MYO5B mRNA and protein expression. However, as DAC unspecifically demethylates the entire DNA, indirect effects may have influenced MYO5B expression. Thus, it was decided to investigate the methylation status of the CpG sites within the entire promoter sequence via mass array technology. The methylation profile analysis of eight CRC cell lines, eight CRC patients as well as four matching normal non-tumor samples thereby did not show any tumor-specific methylation (background signal is defined by a methylation signal of <5%), neither in CRC cell lines nor in primary human tumor samples (FIG. 3B).

It was therefore concluded that the down-regulation of MYO5B mRNA and protein expression in our patient collection is most likely not due to MYO5B promoter methylation, suggesting that other factors, such as histone modifications or inactivating mutations, might be responsible for the loss of MYO5B expression.

Example 5: MYO5B Expression has Prognostic Value in CRC

To evaluate whether MYO5B has prognostic value in CRC, publicly available gene expression data of 585 CRC patients (GSE39582) were used (Marisa et al, 2013). The downregulation of MYO5B was confirmed in this independent dataset, which was not contained in the meta-analysis. Next, patients were divided into two groups ("high" or "low"), based on their MYO5B expression, followed by Kaplan-Meier survival analysis. A significant correlation between low MYO5B expression and shorter overall was detected (FIG. 4A) and relapse-free survival (FIG. 4B). Using the same dataset GSE39582, the analysis was extended to include CRC staging data and found that, in stage I and II (lymph node-negative cancer) patients, both overall (FIG. 4C) and relapse-free survival time (FIG. 4D) were associated with MYO5B expression. The strong increase in the statistical power of MYO5B to predict relapse-free survival in stage I/II patients compared to all stages confounded (p=0.003895 in stage I/II vs p=0.014 in stages I-IV altogether) highlights the clinical relevance of MYO5B expression in early CRC stages.

Indeed, identifying patients at risk for recurrence during the early course of the disease might help clinicians to choose the best treatment plan. It is well known that stage II patients do not all benefit from chemotherapy and that markers able to successfully identify "high-risk" patients are urgently needed. Additionally, the prognostic value of MYO5B was further confirmed using a second independent patient cohort (GSE24551, (Sveen et al, 2011; Agesen et al, 2012) that included clinical data from 160 CRC patients (FIG. 4E). Accordingly, a dataset that contained clinical information on metastasis from 125 CRC patients (GSE28814, (Loboda et al, 2011)) was investigated, whether MYO5B expression could predict the occurrence of metastasis and, by extension, disease relapse. It was found that a patient classification according to their MYO5B expression allows for the prediction of metastasis development (FIG. 4F). In conclusion, the data suggests that MYO5B expression has a strong prognostic value in CRC patients.

Example 6: RAB Family Members RAB8A and RAB25 are Down-Regulated in CRC

Figure 7:
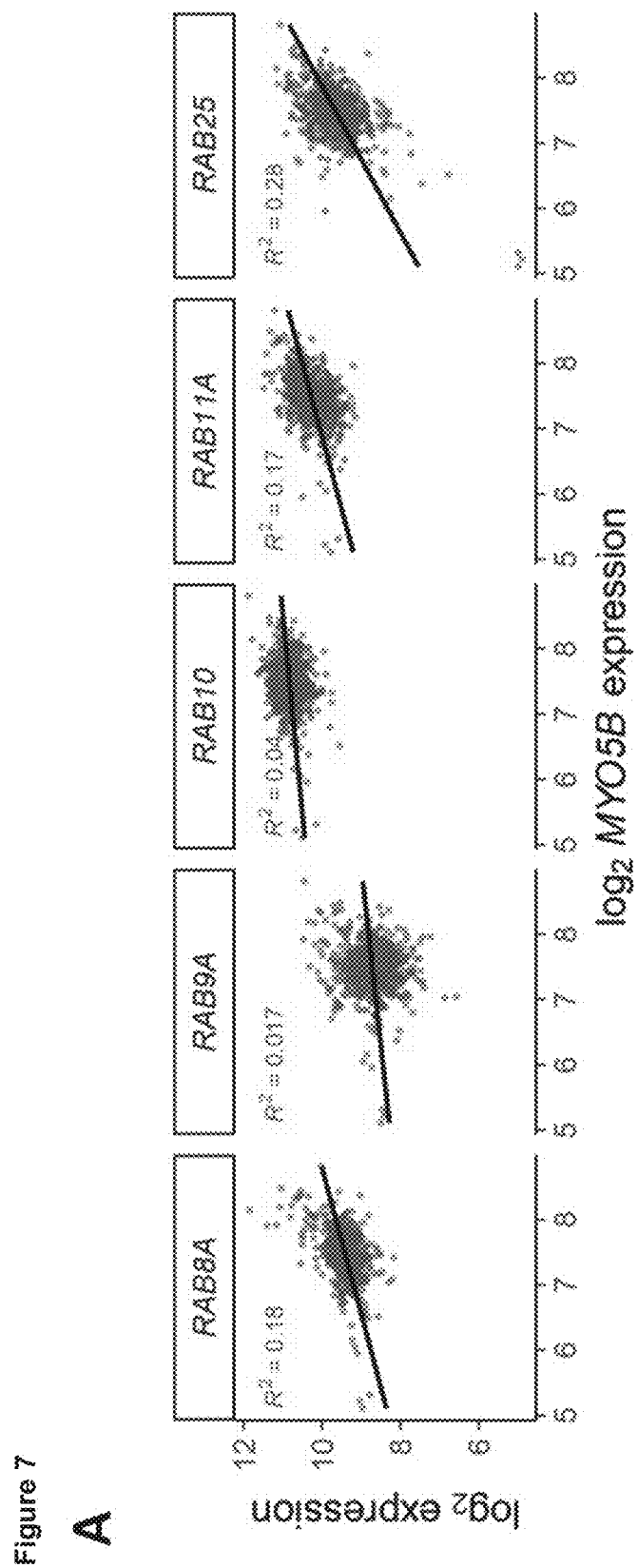
FIG. 7: A. Correlation of the expression of MYO5B with different RAB family members in a meta-analysis of different CRC datasets including 829 patients. B. ROC curves with corresponding AUC values for RAB9A, RAB10, and RAB11A when comparing CRC and healthy samples in the meta-analysis. Distribution of gene expression values for healthy and CRC samples are shown in the insets.
Figure 7:
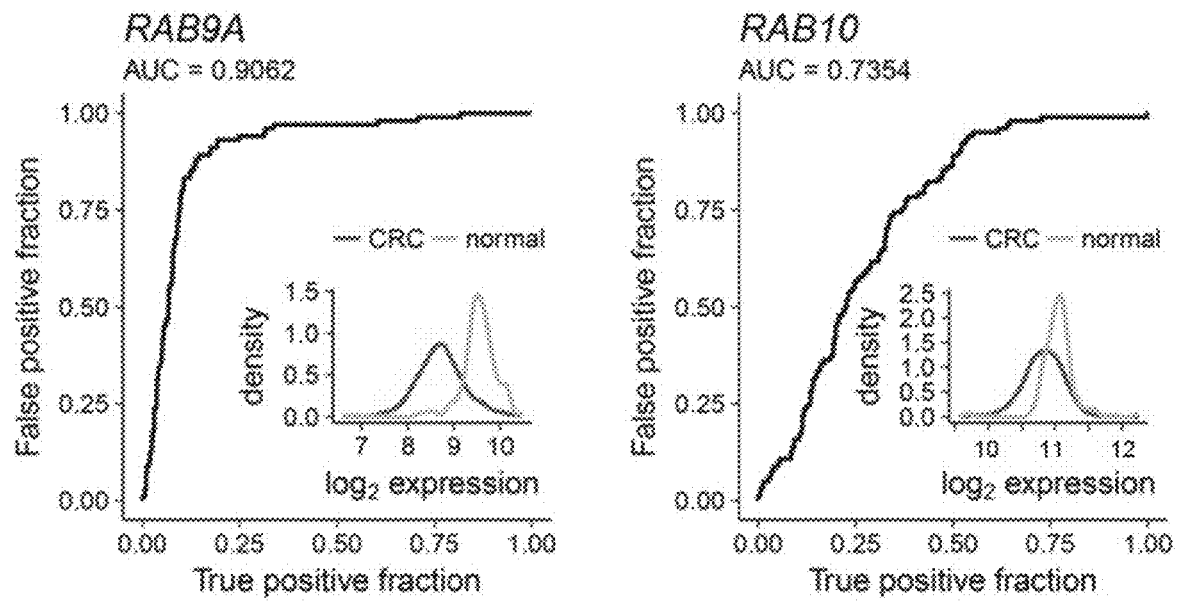
Figure 7:
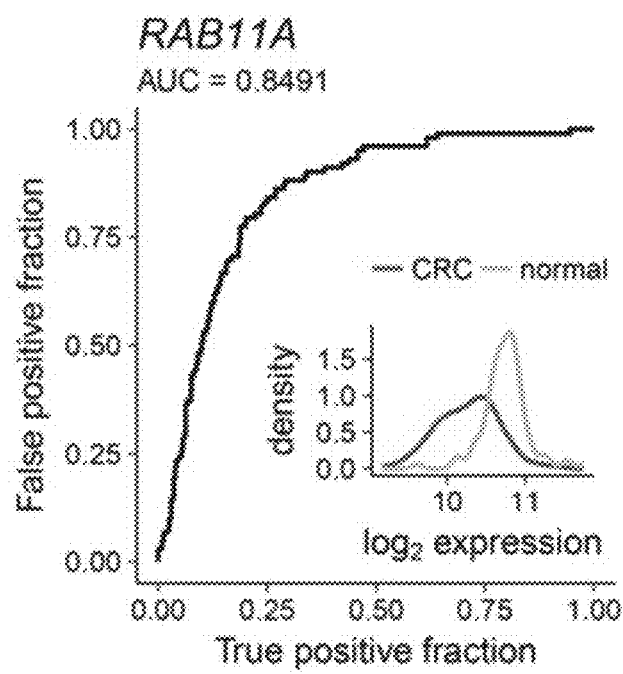

MYO5B is known to interact with different members of the RAB family, such as RAB8A, RAB9A, RAB10, RAB11A and RAB25 (Fan et al, 2004; Ishikura & Klip, 2008; Roland et al, 2011). Besides carrying out trafficking, several of these proteins have also been identified to exhibit a tumor suppressor role in cancer (Mitra et al, 2012). In order to select the most relevant RAB family members in CRC, the correlation was analyzed between the expression of MYO5B and different RAB family members by performing linear regression analyzes using the meta-analysis. Five RAB genes, which are known to interact with MYO5B and for which the expression correlated with that of MYO5B, namely RAB8A, RAB9A, RAB10, RAB11A, and RAB25, were selected for further expression analysis (FIG. 7). Interestingly, all examined RAB members were significantly downregulated in CRC (FIG. 5A).

Furthermore, RAB8A and RAB9A levels were far lower in adenoma samples than in normal healthy samples (FIG. 5A). This finding may potentially be used as an indicator for pre-malignant tumors, as RAB8A and RAB9A expression is further reduced over the course of tumor progression (FIG. 5A). Following this, the suitability of the examined RAB members as biomarkers for CRC were determined. The results obtained were further strengthened by the correlation data, as RAB8A and RAB25 showed the highest AUC values, indicating their suitability as CRC biomarkers (FIG. 5B and FIG. 7).

Finally, the expression of these adapter molecules in CRC was assessed and found that RAB8A and RAB25 were significantly downregulated in the paired tumor/non-tumor dataset (FIG. 5C). It was hypothesized that the expression of MYO5B and its adapter proteins, RAB8A and RAB25, is reduced in CRC, potentially contributing to the loss of polarity in epithelial cells and ultimately leading to tumor invasion and disease progression.

Example 7: The Combinatorial Signature of MYO5B with its Adapter Protein RAB8A has Strong Prognostic Value in CRC A correlation between certain adapter proteins and MYO5B expression was identified, so it was hypothesized that a combinatorial signature with one or more adapter proteins might further increase the prognostic power of MYO5B. To analyze this further, a multitude of different combinatorial signatures (n=63) was tested, carrying the analysis on the GSE39582 dataset (n=585 CRC patients). Strikingly, among the 63 possible different possibilities, the combination of the expression of MYO5B and its adapter protein RAB8A showed the highest response (FIG. 6A) and dramatically increased the prognostic power of MYO5B, both on overall and on relapse-free survival (FIG. 6B).

Example 8: Reduced Expression and Prognostic Value of MYO5B in Lung, Head and Neck, and Skin Cancer In order to assess whether MYO5B is also significantly downregulated on other cancer types, the RNA expression levels of MYO5B was analysed in datasets containing a variety of cancer types (Oncopression resource (Lee et al. 2017) for FIG. 8 and TCGA for FIG. 9). It was found that, compared to samples obtained from normal tissue, MYO5A levels were decreased significantly in tumor samples of lung, head and neck and skin cancer patients. To evaluate whether MYO5B has also a prognostic value in lung, head and neck and skin cancer, publicly available gene expression datasets (GSE30219 for lung cancer; GSE65858 for head and neck cancer; TCGA dataset for skin cancer) were used. Patients were divided into two groups ("high" or "low"), based on their MYO5B expression, followed by Kaplan-Meier survival analysis. A significant correlation between low MYO5B expression and shorter overall was detected for the three cancer types (FIG. 10).

Example 9: Combinatorial Signatures of MYO5B with RAB Family Members and Also Including CDC42, RAC and RhoA Show Prognostic Value in CRC It was hypothesized that combinatorial signatures including RAB family genes, CDC42, RAC and RhoA might increase the prognostic power of MYO5B alone. To analyze this further, a multitude of different combinatorial signatures (N=511) was tested, performing the analysis on the GSE39582 dataset (n=585 CRC patients). Different combinatorial signatures showed increased prognostic power if compared to MYO5B alone, both on overall and on relapse-free survival (FIG. 11, where the Top 20 combinations are represented). Some combinations additionally including RhoA further increased the prognostic value.

REFERENCES

Agesen T H, Sveen A, Merok M A, Lind G E, Nesbakken A, Skotheim R I, Lothe R A (2012) ColoGuideEx: a robust gene classifier specific for stage II colorectal cancer prognosis. *Gut* 61: 1560-1567, doi:10.1136/gutjnl-2011-301179.

Betsou F, Lehmann S, Ashton G, Barnes M, Benson E E, Coppola D, DeSouza Y, Eliason J, Glazer B, Guadagni F, Harding K, Horsfall D J, Kleeberger C, Nanni U, Prasad A, Shea K, Skubitz A, Somiari S. Gunter E (2010) Standard preanalytical coding for biospecimens: defining the sample PREanaytical code. *Cancer Epidemiol Biomarkers Prev* 19: 1004-1011, doi:10.1158/1055-9965.EPI-09-1268.

Biswas S, Rao C M (2017) Epigenetics in cancer Fundamentals and Beyond. *Pharmacol Ther* 173: 118-134, doi:10.1016/j.pharmthera.2017.02.011.

Davis S, Meltzer P S (2007) GEOquery: a bridge between the Gene Expression Omnibus (GEO) and BioConductor. *Bioinformatics* 23: 1846-1847, doi:10.1093/bioinformatics/btm254.

Dong W, Chen X, Chen P, Yue D, Zhu L, Fan Q (2012) Inactivation of MYO5B promotes invasion and motility in gastric cancer cells. *Dig Dis Sci* 57: 1247-1252, doi:10.1007/s10620-011-1989-z.

Dong W, Wang L, Shen R (2013) MYO5B is epigenetically silenced and associated with MET signaling in human gastric cancer. *Dig Dis Sci* 58: 2038-2045, doi:10.1007/s10620-013-2600-6.

Erickson H S, Albert P S, Gillespie J W, Rodriguez-Canales J, Marston Linehan W, Pinto P A, Chuaqui R F, Emmert-Buck M R (2009) Quantitative R T-PCR gene expression analysis of laser microdissected tissue samples. *Nat Protoc* 4: 902-922, doi:10.1038/nprot.2009.61.

Fan G-H, Lapierre L A, Goldenring J R, Sai J, Richmond A (2004) Rab11-family interacting protein 2 and myosin Vb are required for CXCR2 recycling and receptor-mediated chemotaxis. *Mol Biol Cell* 15: 2456-2469, doi:10.1091/mbc.E03-09-0706.

Galamb O, Györffy B, Sipos F, Spisák S, Németh A M, Miheller P, Tulassay Z, Dinya E, Molnár B (2008) Inflammation, adenoma and cancer: objective classification of colon biopsy specimens with gene expression signature. *Dis Markers* 25: 1-16.

Galamb O, Spisák S, Sipos F, Tóth K, Soymosi N, Wichmann B, Krenács T, Valcz G, Tulassay Z, Molnár B (2010) Reversal of gene expression changes in the colorectal normal-adenoma pathway by NS398 selective COX2 inhibitor. *Br J Cancer* 102: 765-773, doi:10.1038/sj.bjc.6605515.

Goswami C P, Nakshatri H (2013) PROGgene: gene expression based survival analysis web application for multiple cancers. *J Clin Bioinforma* 3: 22, doi:10.1186/2043-9113-3-22.

Hari D M, Leung A M, Lee J-H, Sim M-S, Vuong B, Chiu C G, Bilchik A J (2013) AJCC Cancer Staging Manual 7th edition criteria for colon cancer do the complex modifications improve prognostic assessment? *J Am Coll Surg* 217: 181-190, doi:10.1016/j.jamcollsurg.2013.04.018.

Ishikura S, Klip A (2008) Muscle cells engage Rab8A and myosin Vb in insulin-dependent GLUT4 translocation. *Am J Physiol Cell Physiol* 295: C1016-25, doi:10.1152/ajpcell.00277.2008.

Jorissen R N, Gibbs P, Christie M, Prakash S, Upton L, Desai J, Kerr D, Aatonen L A, Arango D, Kruhøffer M. Orntoft T F, Andersen C L, Gruidl M, Kamath V P, Eschrich S, Yeatman T J, Sieber O M (2009) Metastasis-Associated Gene Expression Changes Predict Poor Outcomes in Patients with Dukes Stage B and C Colorectal Cancer. *Clin Cancer Res* 15: 7642-7651, doi:10.1158/1078-0432.CCR-09-1431.

Kassambara A and Kosinski M (2017). survminer: Drawing Survival Curves using 'ggplot2'. https://CRAN.R-project.org/package=survminer Kuang S-Q, Tong W-G, Yang H, Lin W, Lee M K, Fang Z H, Wei Y, Jelinek J, Issa J-P, Garcia-Manero G (2008) Genome-wide identification of aberrantly methylated promoter associated CpG islands in acute lymphocytic leukemia. *Leukemia* 22: 1529-1538, doi:10.1038/leu.2008.130.

Lan L, Han H, Zuo H. Chen Z, Du Y Zhao W, Gu J, Zhang Z (2010) Upregulation of myosin Va by Snail is involved in cancer cell migration and metastasis. *Int J cancer* 126: 53-64, doi:10.1002/ijc.24641.

LaPointe L C, Dunne R, Brown G S, Worthley D L, Molloy P L, Wattchow D, Young G P (2008) Map of differential transcript expression in the normal human large intestine. *Physiol Genomics* 33: 50-64, doi:10.1152/physiolgenomics.00185.2006.

Lee J, Coi C (2017) Oncopression: gene expression compendium for cancer with matched normal tissues. *Bioinformatics* 33: 2068-2070.

Letellier E, Schmitz M, Baig K, Beaume N, Schwartz C, Frasquilho S, Antunes L, Marcon N, Nazarov P V, Vallar L, Even J, Haan S (2014) Identification of SOCS2 and SOCS6 as biomarkers in human colorectal cancer. *Br J Cancer* 111: 726-735, doi:10.1038/bjc.2014.377.

Li Y-R, Yang W-X (2015) Myosins as fundamental components during tumorgenesis: diverse and indispensable. *Oncotarget* 7: 46785-46812, doi:10.18632/oncotarget.8800.

Loboda A, Nebozhyn M V, Watters J W, Buser C A, Shaw P M, Huang P S, Van't Veer L, Tollenaar RAEM, Jackson D B, Agrawal D, Dai H, Yeatman T J (2011) EMT is the dominant program in human colon cancer. *BMC Med Genomics* 4: 9, doi:10.1186/1755-8794-4-9.

Marsa L, de Reynies A, Duval A, Selves J, Gaub M P, Vescovo L, Etienne-Grmaldi M-C, Schiappa R, Guenot D, Ayadi M, Kirzin S, Chazal M, Fléjou J-F, Benchimol D, Berger A, Lagarde A, Pencreach E. Piard F, Elias D, Parc Y, Olschwang S. Milano G, Laurent-Puig P, Boige V (2013) Gene expression classification of colon cancer into molecular subtypes: characterization, validation, and prognostic value. *PLoS Med* 10: e1001453, doi:10.1371/journal.pmed.1001453.

Mitra S, Cheng K W, Mills G B (2012) Rab25 in cancer: a brief update. *Biochem Soc Trans* 40: 1404-1408, doi:10.1042/BST20120249.

Müller T, Hess M W, Schiefermeier N, Pfaller K, Ebner H L, Heinz-Erian P, Ponstingl H, Partsch J, Röllinghoff B, Köhler H, Berger T, Lenhartz H, Schlenck B, Houwen R J, Taylor C J, Zoller H, Lechner S, Goulet O, Utermann G, Ruemmele F M, Huber L A, Janecke A R (2008) MYO5B mutations cause microvillus inclusion disease and disrupt epithelial cell polarity. Nat Genet 40: 1163-1165, doi:10.1038/ng.225.

Ouderkirk J L, Krendel M (2014) Non-muscle myosins in tumor progression, cancer cell invasion, and metastasis. *Cytoskeleton* 71: 447-463, doi:10.1002/cm.21187.

Qureshi-Baig K, Ullmann P, Rodriguez F, Frasquilho S, Nazarov P V., Haan S, Letellier E (2016) What Do We Learn from Spheroid Culture Systems? Insights from Tumorspheres Derived from Primary Colon Cancer Tissue. *PLoS One* 11: e0146052, doi:10.1371/journal.pone.0146052.

Roland J T, Bryant D M, Datta A, Itzen A, Mostov K E, Goldenring J R (2011) Rab GTPase-Myo5B complexes control membrane recycling and epithelial polarization. *Proc Natl Acad Sci USA* 108: 2789-2794, doi:10.1073/pnas.1010754108.

Sabates-Bellver J, Van der Flier L G, de Palo M, Cattaneo E, Maake C, Rehrauer H, Laczko E, Kurowski M a, Bujnicki J M, Menigatti M. Luz J, Ranalli T V, Gomes V, Pastorelli A, Faggiani R, Anti M, Jiricny J, Clevers H, Marra G (2007) Transcriptome profile of human colorectal adenomas. *Mol Cancer Res* 5: 1263-1275, doi:10.1158/1541-7786.MCR-07-0267.

Shi M, He J (2016) ColoFinder a prognostic 9-gene signature improves prognosis for 871 stage II and III colorectal cancer patients. *Peer J* 4: e1804, doi:10.7717/peerj.1804.

Skrzypczak M, Goryca K, Rubel T, Paziewska A, Mikula M, Jarosz D, Pachlewski J, Oledzki J. Ostrowski J, Ostrowsk J (2010) Modeling oncogenic signaling in colon tumors by multidirectional analyses of microarray data directed for maximization of analytical reliability. *PLoS One* 5: doi:10.1371/journal.pone.0013091.

Smith J J, Deane N G, Wu F, Merchant N B, Zhang B, Jiang A, Lu P, Johnson J C, Schmidt C, Bailey C E, Eschrich S, Kis C, Levy S, Washington M K, Heslin M J, Coffey R J, Yeatman T J, Shyr Y, Beauchamp R D (2010) Experimentally derived metastasis gene expression profile predicts recurrence and death in patients with colon cancer. *Gastroenterology* 138: 958-968, doi:10.1053/j.gastro.2009.11.005.

Sveen A, Agesen T H, Nesbakken A, Rognum T O, Lothe R A, Skotheim R I (2011) Transcriptome instability in colorectal cancer identified by exon microarray analyses: Associations with splicing factor expression levels and patient survival. *Genome Med* 3: 32, doi:10.1186/gm248.

Therneau T (2015). A Package for Survival Analysis in S. version 2.38, https://CRAN.R-project.org/package=survival.

Torre L A, Bray F, Siegel R L, Ferlay J, Lortet-Tieulent J, Jemal A (2015) Global cancer statistics, 2012. *C A Cancer J Clin* 65: 87-108, doi:10.3322/caac.21262.

Trybus K M (2008) Myosin V from head to tail. *Cell Mol Life Sci* 65: 1378-1389, doi:10.1007/s00018-008-7507-6.

Tsukamoto S, Ishikawa T, Iida S, Ishiguro M, Mogushi K, Mizushima H, Uetake H, Tanaka H, Sugihara K (2011) Clinical significance of osteoprotegerin expression in human colorectal cancer. *Clin Cancer Res* 17:2444-2450, doi:10.1158/1078-0432.CCR-10-2884.

Ullmann P, Qureshi-Baig K, Rodriguez F, Ginolhac A, Nonnenmacher Y, Temes D, Weiler J, Gäbler K, Bahlawane C, Hiller K, Haan S, Letellier E (2016) Hypoxia-responsive miR-210 promotes self-renewal capacity of colon tumor-initiating cells by repressing ISCU and by inducing lactate production. *Oncotarget* doi:10.18632/oncotarget.11772.

H. Wickham H. (2009). ggplot2: Elegant Graphics for Data Analysis. Springer-Verlag New York. Wickham H. (2017). tidyverse: Easily Install and Load 'Tidyverse' Packages. R package version

The invention claimed is:

1. A method for predicting clinical outcome for and treating a human subject diagnosed with colorectal cancer, wherein predicting clinical outcome consists of:

(a) measuring the expression level of an RNA transcript of MYO5B or an expression product thereof, and optionally an RNA transcript of RAB8A, RAB9A, RAB10, RAB11A, RAB25, CDC42, RAC and/or RhoA, in a biological sample comprising colorectal cancer cells obtained from said subject;

(b) determining a normalized expression level of an RNA transcript of MYO5B, or an expression product thereof, and optionally an RNA transcript of RAB8A, RAB9A, RAB10, RAB11A, RAB25, CDC42, RAC and/or RhoA; and (c) predicting a decreased likelihood of a positive clinical outcome for said subject, if the normalized expression level of MYO5B, or an expression product thereof, and optionally an RNA transcript of RAB8A, RAB9A, RAB10, RAB11A, RAB25, CDC42, RAC and/or RhoA, is decreased compared to gene expression data obtained from corresponding cancer reference samples, wherein the method further comprises (d) treating the subject with chemotherapy, adjuvant chemotherapy, radiation therapy, targeted therapy, or immunotherapy, if a decreased likelihood of a positive clinical outcome for said subject is predicted.

2. The method of claim 1, where in the clinical outcome is recurrence-free interval (RFI), overall survival (OS), disease-free survival (DFS), distant recurrence-free interval (DRFI), likelihood of occurrence of recrudescence, metastasis development or disease progression.

3. The method of claim 1, wherein the subject has stage I or II colorectal cancer.

4. The method of claim 1, wherein said normalized expression level of an RNA transcript of MYO5B and/or RAB8A or an expression product of MYO5B, is determined using a nucleic acid amplification-based method, wherein the nucleic acid amplification method is optionally PCR, or a method for quantifying expression products.

5. The method of claim 1, wherein said normalized expression level of an RNA transcript of MYO5B and/or RAB8A is normalized relative to the expression level of an RNA transcript of at least one reference gene.

6. The method of claim 1, wherein said normalized expression level of an expression product of an RNA transcript of MYO5B is normalized relative to the expression level of an expression product of an RNA transcript of at least one reference gene.

7. The method of claim 1, wherein said normalized expression level of an RNA transcript of RAB9A, RAB10, RAB11A, RAB25, CDC42, RAC and/or RhoA is determined using a nucleic acid amplification-based method, wherein said nucleic acid amplification-based method is optionally PCR.

8. The method of claim 1, wherein the biological sample is a fresh or frozen tissue sample, blood sample, laser-microdissected sample, or paraffin-embedded and fixed sample.

9. The method of claim 1 wherein the chemotherapy, adjuvant chemotherapy, radiation therapy, targeted therapy, or immunotherapy is administered in an effective amount for treating colorectal cancer.

10. A method of predicting clinical outcome for and treating a subject that has undergone surgical resection of colorectal cancer, wherein predicting clinical outcome consists of:

(a) measuring the expression level of an RNA transcript of MYO5B or an expression product thereof, and optionally an RNA transcript of RAB8A, RAB9A, RAB10, RAB11A, RAB25, CDC42, RAC and/or RhoA, in a biological sample comprising colorectal cancer cells obtained from said subject;

(b) determining a normalized expression level of an RNA transcript of MYO5B, or an expression product thereof, and optionally an RNA transcript of RAB8A, RAB9A, RAB10, RAB11A, RAB25, CDC42, RAC and/or RhoA;

(c) predicting a decreased likelihood of a positive clinical outcome for said subject, if the normalized expression level of MYO5B, or an expression product thereof, and optionally an RNA transcript of RAB8A, RAB9A, RAB10, RAB11A, RAB25, CDC42, RAC and/or RhoA, is decreased compared to gene expression data obtained from corresponding cancer reference samples wherein the method further comprises (d) treating the subject with chemotherapy, adjuvant chemotherapy, radiation therapy, targeted therapy, or immunotherapy, if a decreased likelihood of a positive clinical outcome for said subject is predicted.

11. The method of claim 10 wherein the chemotherapy, adjuvant chemotherapy, radiation therapy, targeted therapy, or immunotherapy is administered in an effective amount for treating colorectal cancer.

* * * * *

SEQUENCE LISTING

```
<160> NUMBER OF SEQ ID NOS: 28

<210> SEQ ID NO 1
<211> LENGTH: 22
<212> TYPE: DNA
<213> ORGANISM: Artificial sequence
<220> FEATURE:
<223> OTHER INFORMATION: oligonucleotide primer

<400> SEQUENCE: 1
aacgtgggca tggagaacaa gg                                                 22

<210> SEQ ID NO 2
<211> LENGTH: 22
<212> TYPE: DNA
<213> ORGANISM: Artificial sequence
<220> FEATURE:
<223> OTHER INFORMATION: oligonucleotide primer

<400> SEQUENCE: 2
ttcttcagcc gctctacctc ca                                                 22

<210> SEQ ID NO 3
<211> LENGTH: 22
<212> TYPE: DNA
<213> ORGANISM: Artificial sequence
<220> FEATURE:
<223> OTHER INFORMATION: oligonucleotide primer

<400> SEQUENCE: 3
tcaggaacgg tttcggacga tc                                                 22

<210> SEQ ID NO 4
```

```
<211> LENGTH: 23
<212> TYPE: DNA
<213> ORGANISM: Artificial sequence
<220> FEATURE:
<223> OTHER INFORMATION: oligonucleotide primer

<400> SEQUENCE: 4
gctcctcaat gttgcgaatc cag                                              23

<210> SEQ ID NO 5
<211> LENGTH: 22
<212> TYPE: DNA
<213> ORGANISM: Artificial sequence
<220> FEATURE:
<223> OTHER INFORMATION: oligonucleotide primer

<400> SEQUENCE: 5
actgctcttc ctggagacct ca                                               22

<210> SEQ ID NO 6
<211> LENGTH: 22
<212> TYPE: DNA
<213> ORGANISM: Artificial sequence
<220> FEATURE:
<223> OTHER INFORMATION: oligonucleotide primer

<400> SEQUENCE: 6
gctgttctgt ctctgcttgg ac                                               22

<210> SEQ ID NO 7
<211> LENGTH: 20
<212> TYPE: DNA
<213> ORGANISM: Artificial sequence
<220> FEATURE:
<223> OTHER INFORMATION: oligonucleotide primer

<400> SEQUENCE: 7
tggacaggac tgaacgtctt                                                  20

<210> SEQ ID NO 8
<211> LENGTH: 20
<212> TYPE: DNA
<213> ORGANISM: Artificial sequence
<220> FEATURE:
<223> OTHER INFORMATION: oligonucleotide primer

<400> SEQUENCE: 8
gagcacacag agggctacaa                                                  20

<210> SEQ ID NO 9
<211> LENGTH: 20
<212> TYPE: DNA
<213> ORGANISM: Artificial sequence
<220> FEATURE:
<223> OTHER INFORMATION: oligonucleotide primer

<400> SEQUENCE: 9
cagacaaggt cccaaagaca                                                  20

<210> SEQ ID NO 10
<211> LENGTH: 20
<212> TYPE: DNA
<213> ORGANISM: Artificial sequence
<220> FEATURE:
<223> OTHER INFORMATION: oligonucleotide primer

<400> SEQUENCE: 10
```

-continued

```
ccattatggc gtgtgaagtc                                                   20
```

<210> SEQ ID NO 11
<211> LENGTH: 5547
<212> TYPE: DNA
<213> ORGANISM: Homo sapiens

<400> SEQUENCE: 11

```
atgtcggtgg gcgagctcta cagccagtgc acaagggtct ggatccctga ccctgatgag      60
gtatggcgct cagctgagtt aaccaaggac tacaaagaag agacaagag cctacagctc      120
agactggagg atgaaacgat tctggaatac ccaattgatg tacaacgcaa ccagctgccc     180
ttcttacgga atccagatat cttggtggga aaaatgacc tgactgccct tagctatctt      240
catgagcctg cagttttgca taatttgaag gtccgtttcc tggagtccaa ccatatctac     300
acttactgtg gtatcgtact tgttgccatt aatccttatg aacagttgcc aatctatgga     360
caagatgtca tctataccta cagtggccaa acatgggag acatggaccc ccacatcttt     420
gctgtggcag aagaagccta caagcagatg ccagagatg agaagaatca gtccatcata     480
gtcagtgggg agtctggagc cgggaagacg gtatcagcca gtatgccat gcgctatttc     540
gccaccgttg gtggctcggc cagtgaaacc aacatcgaag agaaggtgct ggcatccagt     600
cccatcatgg aggccattgg aaatgccaag accacccgca tgacaacag cagccgtttt     660
ggcaagtaca tccagattgg ctttgacaaa aggtaccaca tcatcggggc caacatgagg     720
acttacctct ggagaagtc cagagtggtc ttccaggcag atgatgagag gaattaccac     780
atcttttacc agctctgtgc tgctgccggt cttccagaat ttaaagagct tgcactaaca     840
agtgcagagg actttttcta tacatcacag ggaggagaca cttccatcga gggtgtggac     900
gatgctgagg actttgagaa gactcgacaa gccttcacac tcctcggagt gaaagagtcc     960
catcagatga gcatttttaa gataattgct tctatcttgc accttggaag tgtggcgatt    1020
caggctgagc gtgatggtga ttcctgtagt atatcacccc aggatgtata cctaagcaac    1080
ttctgccgac tgctaggggt ggagcacagt cagatggagc actggctgtg tcatcgcaag    1140
ctggtcacca cctcggagac ctacgtcaag accatgtccc tgcagcaggt gatcaatgcg    1200
cgcaacgccc tggcgaagca catctatgcc cagttgttcg gctggattgt ggagcacatc    1260
aacaaggccc tgcacacctc cctcaagcag cactccttca tcggggtcct ggacatctat    1320
gggtttgaga catttgaggt aaacagcttt gagcagttct gtatcaacta tgcaaatgaa    1380
aagctccagc agcagttcaa ctcgcatgtt ttcaaactgg agcaagaaga atacatgaag    1440
gaacagatcc cttggaccct gattgatttt tatgataacc aaccttgtat cgacctcatt    1500
gaagccaagc tgggtatctt ggacctgttg atgaagaat gtaaggtccc caaaggaact    1560
gaccagaact gggctcagaa gctctatgac cggcactcca gcagccagca cttccagaag    1620
ccccgcatgt ccaacacggc cttcatcatc gtccactttg cagacaaggt ggagtacctc    1680
tctgatggtt ttctggagaa aaacagagac acggtgtatg aagagcagat caatatcctg    1740
aaggccagca agttcccact agtggctgac ttgtttcatg atgacaagga ccctgttcct    1800
gccaccaccc ctgggaaggg gtcatcttcg aagatcagcg tccgttctgc cagacccccc    1860
atgaaagtct ccaacaagga gcacaagaaa accgttggcc accagttccg tacctccctg    1920
catctgctca tggagaccct gaatgccacg acacctcact atgtccgctg catcaagccc    1980
aacgatgaga agctccccct tcactttgac ccaaagagag cagtgcagca actcagagcc    2040
```

```
tgcggggtgt tggagacgat tcgaatcagt gcagctggct acccatccag gtgggcctac    2100
catgactttt tcaaccggta tcgggtgctg gtcaagaaga gagagctcgc caacacagac    2160
aaaaaggcca tctgcaggtc tgtcctggag aacctcatca aggaccccga caagttccag    2220
tttggccgca ccaagatctt ctttcgagca ggccaggtgg cctacctgga aagctgcgg    2280 gctgacaagt tccggacagc caccatcatg atccagaaaa ctgtccgggg atggctgcag    2340
aaggtgaaat atcacaggct gaaggggct accttaaccc tgcagaggta ctgccgggga    2400
cacctggccc gcaggctggc tgagcacctg cggaggatca gagcggctgt ggtgctccag    2460
aaacattacc gcatgcagag ggcccgccag gcctaccaga gggtccgcag agctgccgtt    2520
gttatccagg ccttcacccg ggccatgttt gtgcggagaa cctaccgcca ggtcctcatg    2580
gagcacaagg ccaccaccat ccagaagcac gtgcggggct ggatggcacg caggcacttc    2640
cagcggctgc gggatgcagc cattgtcatc cagtgtgcct tccggatgct caaggccagg    2700
cgggagctga aggccctcag gattgaggcc cgctcagcag agcatctgaa acgtctcaac    2760
gtgggcatgg agaacaaggt ggtccagctg cagcggaaga tcgatgagca gaacaaagag    2820
ttcaagacac tttcagagca gttgtccgtg accacctcaa catacaccat ggaggtagag    2880
cggctgaaga aggagctggt gcactaccag cagagcccag tgaggacac cagcctcagg    2940 ctgcaggagg aggtggagag cctgcgcaca gagctgcaga gggcccactc ggagcgcaag    3000
atcttggagg acgcccacag cagggagaaa gatgagctga ggaagcgagt tgcagacctg    3060
gagcaagaaa atgctctctt gaaagatgag aaagaacagc tcaacaacca aatcctgtgc    3120
cagtctaaag atgaatttgc ccagaactct gtgaaggaaa atctcatgaa gaaagaactg    3180
gaggaggagc gatcccggta ccagaaccttt gtgaaggaat attcacagtt ggagcagaga    3240
tacgacaacc ttcgggatga aatgaccatc ataaagcaaa ctccaggtca taggcggaac    3300
ccatcaaacc aaagtagctt agaatctgac tccaattacc cctccatctc cacatctgag    3360
atcggagaca ctgaggatgc cctccagcag gtggaggaaa ttggcctgga aaggcagcc    3420 atggacatga cggtcttcct gaagctgcag aagagagtac gggagctgga gcaggagagg    3480
aaaaagctgc aagtgcagct ggagaagaga gaacagcagg acagcaagaa agtccaggcg    3540
gaaccaccac agactgacat agatttggac ccgaatgcag atctggccta caatagtctg    3600
aagaggcaag agctggagtc agagaacaaa aagctgaaga atgacctgaa tgagctgagg    3660
aaagccgtgg ccgaccaagc cacgcagaat aactccagcc acggctcccc agatagctac    3720
agcctcctgc tgaaccagct caagctggcc cacgaggagc tcgaggtgcg caaggaggag    3780
gtgctcatcc tcaggaccca gatcgtgagc gccgaccagc ggcgactcgc cggcaggaac    3840
gcggagccga acattaatgc cagatcaagt tggcctaaca gtgaaaagca tgttgaccag    3900
gaggatgcca ttgaggccta tcacggggtc tgccagacaa acagcaagac tgaggattgg    3960
ggatatttaa atgaagatgg agaactcggc ttggcctacc aaggcctaaa gcaagttgcc    4020
aggctgctgg aggctcagct gcaggcccag agcctggagc atgaggagga ggtggagcat    4080
ctcaaggctc agctcgaggc cctgaaggag gagatggaca acagcagca gaccttctgc    4140 cagacgctac tgctctcccc agaggcccag gtggaattcg cgttcagca ggaaatatcc    4200 cggctgacca acgagaatct ggaccttaaa gaactggtag aaaagctgga aaagaatgag    4260
aggaagctca aaaagcaact gaagatttac atgaagaaag cccaggacct agaagctgcc    4320
caggcattgg cccagagtga gaggaagcgc catgagctca acaggcaggt cacggtccag    4380
cggaaagaga aggatttcca gggcatgctg gagtaccaca agaggacga ggccctcctc    4440
```

```
atccggaacc tggtgacaga cttgaagccc cagatgctgt cgggcacagt gccctgtctc    4500
cccgcctaca tcctctacat gtgcatccgg cacgcggact acaccaacga cgatctcaag    4560
gtgcactccc tgctgacctc caccatcaac ggcattaaga agtcctgaa aaagcacaat     4620
gatgactttg agatgacgtc attctggtta ccaacacct gccgccttct tcactgtctg     4680
aagcagtaca gcggggatga gggcttcatg actcagaaca ctgcaaagca gaatgaacac    4740
tgtcttaaga attttgacct caccgaatac cgtcaggtgc tgagtgacct ttccattcag    4800
atctaccagc agctcattaa aattgccgag ggcgtgttac agccgatgat agtttctgcc    4860
atgttggaaa atgagagcat tcagggtcta tctggtgtga agcccaccgg ctaccggaag    4920
cgctcctcca gcatggcaga tggggataac tcatactgcc tggaagctat catccgccag    4980
atgaatgcct ttcatacagt catgtgtgac cagggcttgg accctgagat catcctgcag    5040
gtattcaaac agctcttcta catgatcaac gcagtgactc ttaacaaacct gctcttgcgg    5100
aaggacgtct gctcttggag cacaggcatg caactcaggt acaatataag tcagcttgag    5160
gagtggcttc ggggaagaaa ccttcaccag agtggagcag ttcagaccat ggaacctctg    5220
atccaagcag cccagctcct gcaattaaag aagaaaaccc aggaggacgc agaggctatc    5280
tgctccctgt gtacctccct cagcacccag cagattgtca aaattttaaa cctttatact    5340
cccctgaatg aatttgaaga acgggtaaca gtggccttta acgaacaat ccaggcacaa     5400
ctacaagagc ggaatgaccc tcagcaactg ctattagatg ccaagcacat gtttcctgtt    5460
ttgtttccat ttaatccatc ttctctaacc atggactcaa tccacatccc agcgtgtctc    5520
aatctggaat tcctcaatga agtctga                                        5547
```

<210> SEQ ID NO 12
<211> LENGTH: 1848
<212> TYPE: PRT
<213> ORGANISM: Homo sapiens

<400> SEQUENCE: 12

Met Ser Val Gly Glu Leu Tyr Ser Gln Cys Thr Arg Val Trp Ile Pro
1               5                   10                  15

Asp Pro Asp Glu Val Trp Arg Ser Ala Glu Leu Thr Lys Asp Tyr Lys
                20                  25                  30

Glu Gly Asp Lys Ser Leu Gln Leu Arg Leu Glu Asp Glu Thr Ile Leu
            35                  40                  45

Glu Tyr Pro Ile Asp Val Gln Arg Asn Gln Leu Pro Phe Leu Arg Asn
        50                  55                  60

Pro Asp Ile Leu Val Gly Glu Asn Asp Leu Thr Ala Leu Ser Tyr Leu
65                  70                  75                  80

His Glu Pro Ala Val Leu His Asn Leu Lys Val Arg Phe Leu Glu Ser
                85                  90                  95

Asn His Ile Tyr Thr Tyr Cys Gly Ile Val Leu Val Ala Ile Asn Pro
            100                 105                 110

Tyr Glu Gln Leu Pro Ile Tyr Gly Gln Asp Val Ile Tyr Thr Tyr Ser
        115                 120                 125

Gly Gln Asn Met Gly Asp Met Asp Pro His Ile Phe Ala Val Ala Glu
    130                 135                 140

Glu Ala Tyr Lys Gln Met Ala Arg Asp Glu Lys Asn Gln Ser Ile Ile
145                 150                 155                 160

Val Ser Gly Glu Ser Gly Ala Gly Lys Thr Val Ser Ala Lys Tyr Ala
                165                 170                 175

```
Met Arg Tyr Phe Ala Thr Val Gly Gly Ser Ala Ser Glu Thr Asn Ile
            180                 185                 190

Glu Glu Lys Val Leu Ala Ser Pro Ile Met Glu Ala Ile Gly Asn
        195                 200                 205

Ala Lys Thr Thr Arg Asn Asp Asn Ser Ser Arg Phe Gly Lys Tyr Ile
        210                 215                 220

Gln Ile Gly Phe Asp Lys Arg Tyr His Ile Ile Gly Ala Asn Met Arg
225                 230                 235                 240

Thr Tyr Leu Leu Glu Lys Ser Arg Val Val Phe Gln Ala Asp Asp Glu
            245                 250                 255

Arg Asn Tyr His Ile Phe Tyr Gln Leu Cys Ala Ala Gly Leu Pro
            260                 265                 270

Glu Phe Lys Glu Leu Ala Leu Thr Ser Ala Glu Asp Phe Phe Tyr Thr
        275                 280                 285

Ser Gln Gly Gly Asp Thr Ser Ile Glu Gly Val Asp Asp Ala Glu Asp
        290                 295                 300

Phe Glu Lys Thr Arg Gln Ala Phe Thr Leu Leu Gly Val Lys Glu Ser
305                 310                 315                 320

His Gln Met Ser Ile Phe Lys Ile Ile Ala Ser Ile Leu His Leu Gly
                325                 330                 335

Ser Val Ala Ile Gln Ala Glu Arg Asp Gly Asp Ser Cys Ser Ile Ser
        340                 345                 350

Pro Gln Asp Val Tyr Leu Ser Asn Phe Cys Arg Leu Leu Gly Val Glu
        355                 360                 365

His Ser Gln Met Glu His Trp Leu Cys His Arg Lys Leu Val Thr Thr
        370                 375                 380

Ser Glu Thr Tyr Val Lys Thr Met Ser Leu Gln Gln Val Ile Asn Ala
385                 390                 395                 400

Arg Asn Ala Leu Ala Lys His Ile Tyr Ala Gln Leu Phe Gly Trp Ile
            405                 410                 415

Val Glu His Ile Asn Lys Ala Leu His Thr Ser Leu Lys Gln His Ser
            420                 425                 430

Phe Ile Gly Val Leu Asp Ile Tyr Gly Phe Glu Thr Phe Glu Val Asn
        435                 440                 445

Ser Phe Glu Gln Phe Cys Ile Asn Tyr Ala Asn Glu Lys Leu Gln Gln
        450                 455                 460

Gln Phe Asn Ser His Val Phe Lys Leu Glu Gln Glu Glu Tyr Met Lys
465                 470                 475                 480

Glu Gln Ile Pro Trp Thr Leu Ile Asp Phe Tyr Asp Asn Gln Pro Cys
            485                 490                 495

Ile Asp Leu Ile Glu Ala Lys Leu Gly Ile Leu Asp Leu Leu Asp Glu
            500                 505                 510

Glu Cys Lys Val Pro Lys Gly Thr Asp Gln Asn Trp Ala Gln Lys Leu
        515                 520                 525

Tyr Asp Arg His Ser Ser Gln His Phe Gln Lys Pro Arg Met Ser
        530                 535                 540

Asn Thr Ala Phe Ile Ile Val His Phe Ala Asp Lys Val Glu Tyr Leu
545                 550                 555                 560

Ser Asp Gly Phe Leu Glu Lys Asn Arg Asp Thr Val Tyr Glu Glu Gln
            565                 570                 575

Ile Asn Ile Leu Lys Ala Ser Lys Phe Pro Leu Val Ala Asp Leu Phe
            580                 585                 590
```

-continued

His Asp Asp Lys Asp Pro Val Pro Ala Thr Thr Pro Lys Gly Ser
        595             600             605

Ser Ser Lys Ile Ser Val Arg Ser Ala Arg Pro Met Lys Val Ser
    610             615             620

Asn Lys Glu His Lys Lys Thr Val Gly His Gln Phe Arg Thr Ser Leu
625             630             635             640

His Leu Leu Met Glu Thr Leu Asn Ala Thr Thr Pro His Tyr Val Arg
            645             650             655

Cys Ile Lys Pro Asn Asp Glu Lys Leu Pro Phe His Phe Asp Pro Lys
            660             665             670

Arg Ala Val Gln Gln Leu Arg Ala Cys Gly Val Leu Glu Thr Ile Arg
        675             680             685

Ile Ser Ala Ala Gly Tyr Pro Ser Arg Trp Ala Tyr His Asp Phe Phe
690             695             700

Asn Arg Tyr Arg Val Leu Val Lys Lys Arg Glu Leu Ala Asn Thr Asp
705             710             715             720

Lys Lys Ala Ile Cys Arg Ser Val Leu Glu Asn Leu Ile Lys Asp Pro
            725             730             735

Asp Lys Phe Gln Phe Gly Arg Thr Lys Ile Phe Phe Arg Ala Gly Gln
        740             745             750

Val Ala Tyr Leu Glu Lys Leu Arg Ala Asp Lys Phe Arg Thr Ala Thr
    755             760             765

Ile Met Ile Gln Lys Thr Val Arg Gly Trp Leu Gln Lys Val Lys Tyr
    770             775             780

His Arg Leu Lys Gly Ala Thr Leu Thr Leu Gln Arg Tyr Cys Arg Gly
785             790             795             800

His Leu Ala Arg Arg Leu Ala Glu His Leu Arg Arg Ile Arg Ala Ala
            805             810             815

Val Val Leu Gln Lys His Tyr Arg Met Gln Arg Ala Arg Gln Ala Tyr
            820             825             830

Gln Arg Val Arg Arg Ala Ala Val Val Ile Gln Ala Phe Thr Arg Ala
        835             840             845

Met Phe Val Arg Arg Thr Tyr Arg Gln Val Leu Met Glu His Lys Ala
850             855             860

Thr Thr Ile Gln Lys His Val Arg Gly Trp Met Ala Arg Arg His Phe
865             870             875             880

Gln Arg Leu Arg Asp Ala Ala Ile Val Ile Gln Cys Ala Phe Arg Met
            885             890             895

Leu Lys Ala Arg Arg Glu Leu Lys Ala Leu Arg Ile Glu Ala Arg Ser
        900             905             910

Ala Glu His Leu Lys Arg Leu Asn Val Gly Met Glu Asn Lys Val Val
        915             920             925

Gln Leu Gln Arg Lys Ile Asp Glu Gln Asn Lys Glu Phe Lys Thr Leu
    930             935             940

Ser Glu Gln Leu Ser Val Thr Thr Ser Thr Tyr Thr Met Glu Val Glu
945             950             955             960

Arg Leu Lys Lys Glu Leu Val His Tyr Gln Gln Ser Pro Gly Glu Asp
            965             970             975

Thr Ser Leu Arg Leu Gln Glu Glu Val Glu Ser Leu Arg Thr Glu Leu
            980             985             990

Gln Arg Ala His Ser Glu Arg Lys Ile Leu Glu Asp Ala His Ser Arg
        995             1000            1005

Glu Lys Asp Glu Leu Arg Lys Arg Val Ala Asp Leu Glu Gln Glu

-continued

```
               1010                1015                1020
Asn Ala Leu Leu Lys Asp Glu Lys Glu Gln Leu Asn Asn Gln Ile
               1025                1030                1035
Leu Cys Gln Ser Lys Asp Glu Phe Ala Gln Asn Ser Val Lys Glu
               1040                1045                1050
Asn Leu Met Lys Lys Glu Leu Glu Glu Arg Ser Arg Tyr Gln
               1055                1060                1065
Asn Leu Val Lys Glu Tyr Ser Gln Leu Glu Gln Arg Tyr Asp Asn
               1070                1075                1080
Leu Arg Asp Glu Met Thr Ile Ile Lys Gln Thr Pro Gly His Arg
               1085                1090                1095
Arg Asn Pro Ser Asn Gln Ser Ser Leu Glu Ser Asp Ser Asn Tyr
               1100                1105                1110
Pro Ser Ile Ser Thr Ser Glu Ile Gly Asp Thr Glu Asp Ala Leu
               1115                1120                1125
Gln Gln Val Glu Glu Ile Gly Leu Glu Lys Ala Ala Met Asp Met
               1130                1135                1140
Thr Val Phe Leu Lys Leu Gln Lys Arg Val Arg Glu Leu Glu Gln
               1145                1150                1155
Glu Arg Lys Lys Leu Gln Val Gln Leu Glu Lys Arg Glu Gln Gln
               1160                1165                1170
Asp Ser Lys Lys Val Gln Ala Glu Pro Pro Gln Thr Asp Ile Asp
               1175                1180                1185
Leu Asp Pro Asn Ala Asp Leu Ala Tyr Asn Ser Leu Lys Arg Gln
               1190                1195                1200
Glu Leu Glu Ser Glu Asn Lys Lys Leu Lys Asn Asp Leu Asn Glu
               1205                1210                1215
Leu Arg Lys Ala Val Ala Asp Gln Ala Thr Gln Asn Asn Ser Ser
               1220                1225                1230
His Gly Ser Pro Asp Ser Tyr Ser Leu Leu Leu Asn Gln Leu Lys
               1235                1240                1245
Leu Ala His Glu Glu Leu Glu Val Arg Lys Glu Glu Val Leu Ile
               1250                1255                1260
Leu Arg Thr Gln Ile Val Ser Ala Asp Gln Arg Arg Leu Ala Gly
               1265                1270                1275
Arg Asn Ala Glu Pro Asn Ile Asn Ala Arg Ser Ser Trp Pro Asn
               1280                1285                1290
Ser Glu Lys His Val Asp Gln Glu Asp Ala Ile Glu Ala Tyr His
               1295                1300                1305
Gly Val Cys Gln Thr Asn Ser Lys Thr Glu Asp Trp Gly Tyr Leu
               1310                1315                1320
Asn Glu Asp Gly Glu Leu Gly Leu Ala Tyr Gln Gly Leu Lys Gln
               1325                1330                1335
Val Ala Arg Leu Leu Glu Ala Gln Leu Gln Ala Gln Ser Leu Glu
               1340                1345                1350
His Glu Glu Glu Val Glu His Leu Lys Ala Gln Leu Glu Ala Leu
               1355                1360                1365
Lys Glu Glu Met Asp Lys Gln Gln Gln Thr Phe Cys Gln Thr Leu
               1370                1375                1380
Leu Leu Ser Pro Glu Ala Gln Val Glu Phe Gly Val Gln Gln Glu
               1385                1390                1395
Ile Ser Arg Leu Thr Asn Glu Asn Leu Asp Leu Lys Glu Leu Val
               1400                1405                1410
```

-continued

Glu Lys Leu Glu Lys Asn Glu Arg Lys Leu Lys Lys Gln Leu Lys
1415                1420                1425

Ile Tyr Met Lys Lys Ala Gln Asp Leu Glu Ala Ala Gln Ala Leu
1430                1435                1440

Ala Gln Ser Glu Arg Lys Arg His Glu Leu Asn Arg Gln Val Thr
1445                1450                1455

Val Gln Arg Lys Glu Lys Asp Phe Gln Gly Met Leu Glu Tyr His
1460                1465                1470

Lys Glu Asp Glu Ala Leu Leu Ile Arg Asn Leu Val Thr Asp Leu
1475                1480                1485

Lys Pro Gln Met Leu Ser Gly Thr Val Pro Cys Leu Pro Ala Tyr
1490                1495                1500

Ile Leu Tyr Met Cys Ile Arg His Ala Asp Tyr Thr Asn Asp Asp
1505                1510                1515

Leu Lys Val His Ser Leu Leu Thr Ser Thr Ile Asn Gly Ile Lys
1520                1525                1530

Lys Val Leu Lys Lys His Asn Asp Asp Phe Glu Met Thr Ser Phe
1535                1540                1545

Trp Leu Ser Asn Thr Cys Arg Leu Leu His Cys Leu Lys Gln Tyr
1550                1555                1560

Ser Gly Asp Glu Gly Phe Met Thr Gln Asn Thr Ala Lys Gln Asn
1565                1570                1575

Glu His Cys Leu Lys Asn Phe Asp Leu Thr Glu Tyr Arg Gln Val
1580                1585                1590

Leu Ser Asp Leu Ser Ile Gln Ile Tyr Gln Gln Leu Ile Lys Ile
1595                1600                1605

Ala Glu Gly Val Leu Gln Pro Met Ile Val Ser Ala Met Leu Glu
1610                1615                1620

Asn Glu Ser Ile Gln Gly Leu Ser Gly Val Lys Pro Thr Gly Tyr
1625                1630                1635

Arg Lys Arg Ser Ser Ser Met Ala Asp Gly Asp Asn Ser Tyr Cys
1640                1645                1650

Leu Glu Ala Ile Ile Arg Gln Met Asn Ala Phe His Thr Val Met
1655                1660                1665

Cys Asp Gln Gly Leu Asp Pro Glu Ile Ile Leu Gln Val Phe Lys
1670                1675                1680

Gln Leu Phe Tyr Met Ile Asn Ala Val Thr Leu Asn Asn Leu Leu
1685                1690                1695

Leu Arg Lys Asp Val Cys Ser Trp Ser Thr Gly Met Gln Leu Arg
1700                1705                1710

Tyr Asn Ile Ser Gln Leu Glu Glu Trp Leu Arg Gly Arg Asn Leu
1715                1720                1725

His Gln Ser Gly Ala Val Gln Thr Met Glu Pro Leu Ile Gln Ala
1730                1735                1740

Ala Gln Leu Leu Gln Leu Lys Lys Lys Thr Gln Glu Asp Ala Glu
1745                1750                1755

Ala Ile Cys Ser Leu Cys Thr Ser Leu Ser Thr Gln Gln Ile Val
1760                1765                1770

Lys Ile Leu Asn Leu Tyr Thr Pro Leu Asn Glu Phe Glu Glu Arg
1775                1780                1785

Val Thr Val Ala Phe Ile Arg Thr Ile Gln Ala Gln Leu Gln Glu
1790                1795                1800

Arg Asn Asp Pro Gln Gln Leu Leu Leu Asp Ala Lys His Met Phe
    1805                1810                1815

Pro Val Leu Phe Pro Phe Asn Pro Ser Ser Leu Thr Met Asp Ser
    1820                1825                1830

Ile His Ile Pro Ala Cys Leu Asn Leu Glu Phe Leu Asn Glu Val
    1835                1840                1845

<210> SEQ ID NO 13
<211> LENGTH: 624
<212> TYPE: DNA
<213> ORGANISM: Homo sapiens

<400> SEQUENCE: 13

```
atggcgaaga cctacgatta cctgttcaag ctgctgctga tcggggactc gggggtgggg      60
aagacctgtg tcctgttccg cttctccgag gacgccttca actccacttt tatctccacc     120
ataggaattg actttaaaat taggaccata gagctcgatg gcaagagaat taaactgcag     180
atatgggaca cagccggtca ggaacggttt cggacgatca aacggcccta ctacaggggt     240
gcaatgggca tcatgctggt ctacgacatc accaacgaga gtccttcga caacatccgg      300 aactggattc gcaacattga ggagcacgcc tctgcagacg tcgaaaagat gatactcggg     360
aacaagtgtg atgtgaatga caagagacaa gtttccaagg aacggggaga aaagctggcc     420
ctcgactatg gaatcaagtt catggagacc agcgcgaagg ccaacatcaa tgtggaaaat     480
gcatttttca ctctcgccag agatatcaaa gcaaaaatgg acaaaaaatt ggaaggcaac     540
agcccccagg ggagcaacca gggagtcaaa atcacaccgg accagcagaa gaggagcagc     600
tttttccgat gtgttcttct gtga                                           624
```

<210> SEQ ID NO 14
<211> LENGTH: 207
<212> TYPE: PRT
<213> ORGANISM: Homo sapiens

<400> SEQUENCE: 14

Met Ala Lys Thr Tyr Asp Tyr Leu Phe Lys Leu Leu Leu Ile Gly Asp
1               5                   10                  15

Ser Gly Val Gly Lys Thr Cys Val Leu Phe Arg Phe Ser Glu Asp Ala
            20                  25                  30

Phe Asn Ser Thr Phe Ile Ser Thr Ile Gly Ile Asp Phe Lys Ile Arg
        35                  40                  45

Thr Ile Glu Leu Asp Gly Lys Arg Ile Lys Leu Gln Ile Trp Asp Thr
    50                  55                  60

Ala Gly Gln Glu Arg Phe Arg Thr Ile Thr Thr Ala Tyr Tyr Arg Gly
65                  70                  75                  80

Ala Met Gly Ile Met Leu Val Tyr Asp Ile Thr Asn Glu Lys Ser Phe
                85                  90                  95

Asp Asn Ile Arg Asn Trp Ile Arg Asn Ile Glu Glu His Ala Ser Ala
            100                 105                 110

Asp Val Glu Lys Met Ile Leu Gly Asn Lys Cys Asp Val Asn Asp Lys
        115                 120                 125

Arg Gln Val Ser Lys Glu Arg Gly Glu Lys Leu Ala Leu Asp Tyr Gly
    130                 135                 140

Ile Lys Phe Met Glu Thr Ser Ala Lys Ala Asn Ile Asn Val Glu Asn
145                 150                 155                 160

Ala Phe Phe Thr Leu Ala Arg Asp Ile Lys Ala Lys Met Asp Lys Lys
                165                 170                 175

Leu Glu Gly Asn Ser Pro Gln Gly Ser Asn Gln Gly Val Lys Ile Thr
            180                 185                 190

Pro Asp Gln Gln Lys Arg Ser Ser Phe Phe Arg Cys Val Leu Leu
        195                 200                 205

<210> SEQ ID NO 15
<211> LENGTH: 606
<212> TYPE: DNA
<213> ORGANISM: Homo sapiens

<400> SEQUENCE: 15
atggcaggaa aatcatcact ttttaaagta attctccttg gagatggtgg agttgggaag      60
agttcactta tgaacagata tgtaactaat aagtttgata cccagctctt ccatacaata     120
ggtgtggaat ttttaaataa agatttggaa gtggatggac attttgttac catgcagatt     180
tgggacacgg caggtcagga gcgattccga agcctgagga caccatttta cagaggttct     240
gactgctgcc tgcttacttt tagtgtcgat gattcacaaa gcttccagaa cttaagtaac     300
tggaagaaag aattcatata ttatgcagat gtgaaagagc ctgagagctt cccttttgtg     360
attctgggta caagattga cataagcgaa cggcaggtgt ctacagaaga agcccaagct     420
tggtgcaggg acaacggcga ctatccttat tttgaaacaa gtgcaaaaga tgccacaaat     480
gtggcagcag cctttgagga agcggttcga agagttcttg ctaccgagga taggtcagat     540
catttgattc agacagacac agtcaatctt caccgaaagc ccaagcctag ctcatcttgc     600
tgttga                                                                606

<210> SEQ ID NO 16
<211> LENGTH: 201
<212> TYPE: PRT
<213> ORGANISM: Homo sapiens

<400> SEQUENCE: 16

Met Ala Gly Lys Ser Ser Leu Phe Lys Val Ile Leu Leu Gly Asp Gly
1               5                   10                  15

Gly Val Gly Lys Ser Ser Leu Met Asn Arg Tyr Val Thr Asn Lys Phe
            20                  25                  30

Asp Thr Gln Leu Phe His Thr Ile Gly Val Glu Phe Leu Asn Lys Asp
        35                  40                  45

Leu Glu Val Asp Gly His Phe Val Thr Met Gln Ile Trp Asp Thr Ala
    50                  55                  60

Gly Gln Glu Arg Phe Arg Ser Leu Arg Thr Pro Phe Tyr Arg Gly Ser
65                  70                  75                  80

Asp Cys Cys Leu Leu Thr Phe Ser Val Asp Asp Ser Gln Ser Phe Gln
                85                  90                  95

Asn Leu Ser Asn Trp Lys Lys Glu Phe Ile Tyr Tyr Ala Asp Val Lys
            100                 105                 110

Glu Pro Glu Ser Phe Pro Phe Val Ile Leu Gly Asn Lys Ile Asp Ile
        115                 120                 125

Ser Glu Arg Gln Val Ser Thr Glu Glu Ala Gln Ala Trp Cys Arg Asp
    130                 135                 140

Asn Gly Asp Tyr Pro Tyr Phe Glu Thr Ser Ala Lys Asp Ala Thr Asn
145                 150                 155                 160

Val Ala Ala Ala Phe Glu Glu Ala Val Arg Arg Val Leu Ala Thr Glu
                165                 170                 175

Asp Arg Ser Asp His Leu Ile Gln Thr Asp Thr Val Asn Leu His Arg

```
                    180                 185                 190

Lys Pro Lys Pro Ser Ser Ser Cys Cys
        195                 200

<210> SEQ ID NO 17
<211> LENGTH: 603
<212> TYPE: DNA
<213> ORGANISM: Homo sapiens

<400> SEQUENCE: 17
atggcgaaga agacgtacga cctgcttttc aagctgctcc tgatcgggga ttccggagtg     60
gggaagacct gcgtcctttt tcgttttttcg gatgatgcct caatactac ctttatttcc    120 accataggaa tagacttcaa gatcaaaaca gttgaattac aaggaaagaa gatcaagcta    180
cagatatggg atacagcagg ccaggagcga tttcacacca tcacaacctc ctactacaga    240
ggcgcaatgg gtatcatgct agtatatgac atcaccaatg gtaaaagttt tgaaaacatc    300
agcaaatggc ttagaaacat agatgagcat gccaatgaag atgtggaaag aatgttacta    360
ggaaacaagt gtgatatgga cgacaaaaga gttgtaccta aggaaaagg agaacagatt    420 gcaagggagc atggtattag gttttttgag actagtgcaa aagcaaatat aaacatcgaa    480
aaggcgttcc tcacgttagc tgaagatatc cttcgaaaga cccctgtaaa agagcccaac    540
agtgaaaatg tagatatcag cagtggagga ggcgtgacag gctggaagag caaatgctgc    600
tga                                                                  603

<210> SEQ ID NO 18
<211> LENGTH: 200
<212> TYPE: PRT
<213> ORGANISM: Homo sapiens

<400> SEQUENCE: 18

Met Ala Lys Lys Thr Tyr Asp Leu Leu Phe Lys Leu Leu Leu Ile Gly
1               5                   10                  15

Asp Ser Gly Val Gly Lys Thr Cys Val Leu Phe Arg Phe Ser Asp Asp
            20                  25                  30

Ala Phe Asn Thr Thr Phe Ile Ser Thr Ile Gly Ile Asp Phe Lys Ile
        35                  40                  45

Lys Thr Val Glu Leu Gln Gly Lys Lys Ile Lys Leu Gln Ile Trp Asp
    50                  55                  60

Thr Ala Gly Gln Glu Arg Phe His Thr Ile Thr Thr Ser Tyr Tyr Arg
65                  70                  75                  80

Gly Ala Met Gly Ile Met Leu Val Tyr Asp Ile Thr Asn Gly Lys Ser
                85                  90                  95

Phe Glu Asn Ile Ser Lys Trp Leu Arg Asn Ile Asp Glu His Ala Asn
            100                 105                 110

Glu Asp Val Glu Arg Met Leu Leu Gly Asn Lys Cys Asp Met Asp Asp
        115                 120                 125

Lys Arg Val Val Pro Lys Gly Lys Gly Glu Gln Ile Ala Arg Glu His
    130                 135                 140

Gly Ile Arg Phe Phe Glu Thr Ser Ala Lys Ala Asn Ile Asn Ile Glu
145                 150                 155                 160

Lys Ala Phe Leu Thr Leu Ala Glu Asp Ile Leu Arg Lys Thr Pro Val
                165                 170                 175

Lys Glu Pro Asn Ser Glu Asn Val Asp Ile Ser Ser Gly Gly Gly Val
            180                 185                 190
```

Thr Gly Trp Lys Ser Lys Cys Cys
        195                 200

<210> SEQ ID NO 19
<211> LENGTH: 651
<212> TYPE: DNA
<213> ORGANISM: Homo sapiens

<400> SEQUENCE: 19
atgggcaccc gcgacgacga gtacgactac ctctttaaag ttgtccttat tggagattct      60
ggtgttggaa agagtaatct cctgtctcga tttactcgaa atgagtttaa tctggaaagc     120
aagagcacca ttggagtaga gtttgcaaca agaagcatcc aggttgatgg aaaaacaata     180
aaggcacaga tatgggacac agcagggcaa gagcgatatc gagctataac atcagcatat     240
tatcgtggag ctgtaggtgc cttattggtt tatgacattg ctaaacatct cacatatgaa     300
aatgtagagc gatggctgaa agaactgaga gatcatgctg atagtaacat tgttatcatg     360
cttgtgggca ataagagtga tctacgtcat ctcagggcag ttcctacaga tgaagcaaga     420
gcttttgcag aaaagaatgg tttgtcattc attgaaactt cggccctaga ctctacaaat     480
gtagaagctg cttttcagac aattttaaca gagatttacc gcattgtttc tcagaagcaa     540
atgtcagaca gacgcgaaaa tgacatgtct ccaagcaaca atgtggttcc tattcatgtt     600
ccaccaacca ctgaaaacaa gccaaaggtg cagtgctgtc agaacatcta a              651

<210> SEQ ID NO 20
<211> LENGTH: 216
<212> TYPE: PRT
<213> ORGANISM: Homo sapiens

<400> SEQUENCE: 20

Met Gly Thr Arg Asp Asp Glu Tyr Asp Tyr Leu Phe Lys Val Val Leu
1               5                   10                  15

Ile Gly Asp Ser Gly Val Gly Lys Ser Asn Leu Leu Ser Arg Phe Thr
            20                  25                  30

Arg Asn Glu Phe Asn Leu Glu Ser Lys Ser Thr Ile Gly Val Glu Phe
        35                  40                  45

Ala Thr Arg Ser Ile Gln Val Asp Gly Lys Thr Ile Lys Ala Gln Ile
    50                  55                  60

Trp Asp Thr Ala Gly Gln Glu Arg Tyr Arg Ala Ile Thr Ser Ala Tyr
65                  70                  75                  80

Tyr Arg Gly Ala Val Gly Ala Leu Leu Val Tyr Asp Ile Ala Lys His
                85                  90                  95

Leu Thr Tyr Glu Asn Val Glu Arg Trp Leu Lys Glu Leu Arg Asp His
            100                 105                 110

Ala Asp Ser Asn Ile Val Ile Met Leu Val Gly Asn Lys Ser Asp Leu
        115                 120                 125

Arg His Leu Arg Ala Val Pro Thr Asp Glu Ala Arg Ala Phe Ala Glu
    130                 135                 140

Lys Asn Gly Leu Ser Phe Ile Glu Thr Ser Ala Leu Asp Ser Thr Asn
145                 150                 155                 160

Val Glu Ala Ala Phe Gln Thr Ile Leu Thr Glu Ile Tyr Arg Ile Val
                165                 170                 175

Ser Gln Lys Gln Met Ser Asp Arg Arg Glu Asn Asp Met Ser Pro Ser
            180                 185                 190

Asn Asn Val Val Pro Ile His Val Pro Pro Thr Thr Glu Asn Lys Pro
        195                 200                 205

```
Lys Val Gln Cys Cys Gln Asn Ile
    210                 215
```

<210> SEQ ID NO 21
<211> LENGTH: 642
<212> TYPE: DNA
<213> ORGANISM: Homo sapiens

<400> SEQUENCE: 21

```
atggggaatg gaactgagga agattataac tttgtcttca aggtggtgct gatcggcgaa      60
tcaggtgtgg ggaagaccaa tctactctcc cgattcacgc gcaatgagtt cagccacgac     120
agccgcacca ccatcggggt tgagttctcc acccgcactg tgatgttggg caccgctgct     180
gtcaaggctc agatctggga cacagctggc ctggagcgt accgagccat cacctcgggcg    240
tactatcgtg gtgcagtggg ggccctcctg gtgtttgacc taaccaagca ccagacctat     300
gctgtggtgg agcgatggct gaaggagctc tatgaccatg ctgaagccac gatcgtcgtc     360
atgctcgtgg gtaacaaaag tgacctcagc caggcccggg aagtgcccac tgaggaggcc     420
cgaatgttcg ctgaaaacaa tggactgctc ttcctggaga cctcagccct ggactctacc     480
aatgttgagc tagcctttga gactgtcctg aaagaaatct ttgcgaaggt gtccaagcag     540
agacagaaca gcatccggac caatgccatc actctgggca gtgcccaggc tggacaggag     600
cctggccctg gggagaagag ggcctgttgc atcagcctct ga                        642
```

<210> SEQ ID NO 22
<211> LENGTH: 213
<212> TYPE: PRT
<213> ORGANISM: Homo sapiens

<400> SEQUENCE: 22

```
Met Gly Asn Gly Thr Glu Glu Asp Tyr Asn Phe Val Phe Lys Val Val
1               5                   10                  15

Leu Ile Gly Glu Ser Gly Val Gly Lys Thr Asn Leu Leu Ser Arg Phe
            20                  25                  30

Thr Arg Asn Glu Phe Ser His Asp Ser Arg Thr Thr Ile Gly Val Glu
        35                  40                  45

Phe Ser Thr Arg Thr Val Met Leu Gly Thr Ala Ala Val Lys Ala Gln
    50                  55                  60

Ile Trp Asp Thr Ala Gly Leu Glu Arg Tyr Arg Ala Ile Thr Ser Ala
65                  70                  75                  80

Tyr Tyr Arg Gly Ala Val Gly Ala Leu Leu Val Phe Asp Leu Thr Lys
                85                  90                  95

His Gln Thr Tyr Ala Val Val Glu Arg Trp Leu Lys Glu Leu Tyr Asp
            100                 105                 110

His Ala Glu Ala Thr Ile Val Val Met Leu Val Gly Asn Lys Ser Asp
        115                 120                 125

Leu Ser Gln Ala Arg Glu Val Pro Thr Glu Glu Ala Arg Met Phe Ala
    130                 135                 140

Glu Asn Asn Gly Leu Leu Phe Leu Glu Thr Ser Ala Leu Asp Ser Thr
145                 150                 155                 160

Asn Val Glu Leu Ala Phe Glu Thr Val Leu Lys Glu Ile Phe Ala Lys
                165                 170                 175

Val Ser Lys Gln Arg Gln Asn Ser Ile Arg Thr Asn Ala Ile Thr Leu
            180                 185                 190

Gly Ser Ala Gln Ala Gly Gln Glu Pro Gly Pro Gly Glu Lys Arg Ala
```

-continued

```
                   195                 200                 205

Cys Cys Ile Ser Leu
            210

<210> SEQ ID NO 23
<211> LENGTH: 576
<212> TYPE: DNA
<213> ORGANISM: Homo sapiens

<400> SEQUENCE: 23
atgcagacaa ttaagtgtgt tgttgtgggc gatggtgctg ttggtaaaac atgtctcctg      60
atatcctaca caacaaacaa atttccatcg aatatgtac cgactgtttt tgacaactat     120
gcagtcacag ttatgattgg tggagaacca tatactcttg gacttttga tactgcaggg     180 caagaggatt atgacagatt acgaccgctg agttatccac aaacagatgt atttctagtc     240 tgttttcag tggtctctcc atcttcattt gaaaacgtga agaaaagtg ggtgcctgag      300 ataactcacc actgtccaaa gactcctttc ttgcttgttg ggactcaaat tgatctcaga     360
gatgacccct ctactattga aaacttgcc aagaacaaac agaagcctat cactccagag     420
actgctgaaa agctggcccg tgacctgaag gctgtcaagt atgtggagtg ttctgcactt     480
acacagaaag gcctaaagaa tgtatttgac gaagcaatat tggctgccct ggagcctcca     540
gaaccgaaga agagccgcag tgtgtgctg ctatga                               576

<210> SEQ ID NO 24
<211> LENGTH: 191
<212> TYPE: PRT
<213> ORGANISM: Homo sapiens

<400> SEQUENCE: 24

Met Gln Thr Ile Lys Cys Val Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
        115                 120                 125

Leu Ala Lys Asn Lys Gln Lys Pro Ile Thr Pro Glu Thr Ala Glu Lys
    130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
            180                 185                 190

<210> SEQ ID NO 25
```

<211> LENGTH: 579
<212> TYPE: DNA
<213> ORGANISM: Homo sapiens

<400> SEQUENCE: 25

```
atgcaggcca tcaagtgtgt ggtggtggga gacggagctg taggtaaaac ttgcctactg      60
atcagttaca caaccaatgc atttcctgga gaatatatcc ctactgtctt tgacaattat     120
tctgccaatg ttatggtaga tggaaaaccg gtgaatctgg gcttatggga tacagctgga     180
caagaagatt atgacagatt acgcccccta tcctatccgc aaacagatgt gttcttaatt     240
tgctttttcc cttgtgagtcc tgcatcattt gaaaatgtcc gtgcaaagtg gtatcctgag     300
gtgcggcacc actgtcccaa cactcccatc atcctagtgg gaactaaact tgatcttagg     360
gatgataaag acacgatcga gaaactgaag gagaagaagc tgactcccat cacctatccg     420
cagggtctag ccatggctaa ggagattggt gctgtaaaat acctggagtg ctcggcgctc     480
acacagcgag gcctcaagac agtgtttgac gaagcgatcc gagcagtcct ctgcccgcct     540
cccgtgaaga gaggaagag aaaatgcctg ctgttgtaa                              579
```

<210> SEQ ID NO 26
<211> LENGTH: 192
<212> TYPE: PRT
<213> ORGANISM: Homo sapiens

<400> SEQUENCE: 26

```
Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Gly
                35                  40                  45

Lys Pro Val Asn Leu Gly Leu Trp Asp Thr Ala Gly Gln Glu Asp Tyr
            50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
                100                 105                 110

Val Gly Thr Lys Leu Asp Leu Arg Asp Asp Lys Asp Thr Ile Glu Lys
            115                 120                 125

Leu Lys Glu Lys Lys Leu Thr Pro Ile Thr Tyr Pro Gln Gly Leu Ala
        130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
                180                 185                 190
```

<210> SEQ ID NO 27
<211> LENGTH: 582
<212> TYPE: DNA
<213> ORGANISM: Homo sapiens

<400> SEQUENCE: 27

```
atggctgcca tccggaagaa actggtgatt gttggtgatg gagcctgtgg aaagacatgc      60
```

```
ttgctcatag tcttcagcaa ggaccagttc ccagaggtgt atgtgcccac agtgtttgag      120
aactatgtgg cagatatcga ggtggatgga aagcaggtag agttggcttt gtgggacaca      180
gctgggcagg aagattatga tcgcctgagg cccctctcct acccagatac cgatgttata      240
ctgatgtgtt tttccatcga cagccctgat agtttagaaa acatcccaga aaagtggacc      300
ccagaagtca agcatttctg tcccaacgtg cccatcatcc tggttgggaa taagaaggat      360
cttcggaatg atgagcacac aaggcgggag ctagccaaga tgaagcagga gccggtgaaa      420
cctgaagaag gcagagatat ggcaaacagg attggcgctt ttgggtacat ggagtgttca      480
gcaaagacca aagatggagt gagagaggtt tttgaaatgg ctacgagagc tgctctgcaa      540
gctagacgtg ggaagaaaaa atctgggtgc cttgtcttgt ga                        582

<210> SEQ ID NO 28
<211> LENGTH: 193
<212> TYPE: PRT
<213> ORGANISM: Homo sapiens

<400> SEQUENCE: 28

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
                20                  25                  30

Val Tyr Val Pro Thr Val Phe Glu Asn Tyr Val Ala Asp Ile Glu Val
            35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
                100                 105                 110

Ile Leu Val Gly Asn Lys Lys Asp Leu Arg Asn Asp Glu His Thr Arg
            115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
                180                 185                 190

Leu
```